(12) United States Patent
Houser et al.

(10) Patent No.: US 6,599,302 B2
(45) Date of Patent: *Jul. 29, 2003

(54) AORTIC ANEURYSM TREATMENT SYSTEMS

(75) Inventors: Russell A. Houser, Livermore, CA (US); James G. Whayne, San Jose, CA (US); Sidney D. Fleischman, Menlo Park, CA (US)

(73) Assignee: Converge Medical, Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 18 days.

(21) Appl. No.: 09/329,658

(22) Filed: Jun. 10, 1999

(65) Prior Publication Data

US 2003/0033005 A1 Feb. 13, 2003

Related U.S. Application Data

(60) Provisional application No. 60/088,705, filed on Jun. 10, 1998, and provisional application No. 60/111,948, filed on Dec. 11, 1998.

(51) Int. Cl.[7] .............................. A61B 17/04; A61F 2/06
(52) U.S. Cl. .................... 606/153; 606/155; 606/149; 623/23.64
(58) Field of Search .................... 606/153, 139, 606/155, 149; 623/1, 3, 12, 11, 23.64; 604/8, 264

(56) References Cited

U.S. PATENT DOCUMENTS

| 4,214,587 A | 7/1980 | Sakura, Jr. |
| 4,366,819 A | 1/1983 | Kaster |
| 4,368,736 A | 1/1983 | Kaster |
| 4,562,596 A * | 1/1986 | Kornberg ................. 623/1.32 |
| 4,607,637 A | 8/1986 | Berggren et al. |

(List continued on next page.)

FOREIGN PATENT DOCUMENTS

| EP | 824 901 A2 A3 | 2/1998 |
| EP | 894 475 A1 | 2/1999 |
| WO | WO 96/22745 | 8/1996 |
| WO | WO 97/13463 | 4/1997 |
| WO | WO 97/13471 | 4/1997 |

(List continued on next page.)

OTHER PUBLICATIONS

Yusuf, S. W. et al. (1994). "Transfemoral Endoluminal Repair of Abdominal Aortic Aneurysm with Bifuricated Graft," *Lancet* 344(8923):650–651.

Cragg et al. (1982). "Endovascular Diathermic Vessel Occlusion," *Radiology*. 144: 303–308.

Gorisch et al. (1982). "Heat–Induced Contraction of Blood Vessels," *Lasers in Surgery and Medicine*. 2: 1–13.

Heijmen et al. (1999). "A Novel One–Shot Anastomotic Stapler Prototype for Coronary Bypass Grafting on the Beating Heart: Feasibility in the Pig," *J. Thorac Cardiovasc Surg*. 117: 117–125.

*Primary Examiner*—Gary Jackson
(74) *Attorney, Agent, or Firm*—Carol LaSalle Bozicevic, Field & Francis LLP

(57) ABSTRACT

A system and components for treating aortic aneurysms includes a reinforcing graft and fittings for securing the graft to a host vessel and to branch vessels, for example the iliac and renal arteries. Combinations of fittings and rings or other compression mechanisms secure vessels or grafts frictionally, for end-end or end-side couplings. A variety of tools are disclosed for manipulating retaining rings, everting portions of grafts or vessels in the course of coupling them to fittings, and clamping fittings while positioning the retaining rings.

31 Claims, 37 Drawing Sheets

U.S. PATENT DOCUMENTS

| | | |
|---|---|---|
| 4,624,257 A | 11/1986 | Berggren et al. |
| 4,657,019 A | 4/1987 | Walsh et al. |
| 4,665,906 A | 5/1987 | Jervis |
| 4,787,386 A | 11/1988 | Walsh et al. |
| 4,917,087 A | 4/1990 | Walsh et al. |
| 4,917,090 A | 4/1990 | Berggren et al. |
| 4,917,091 A | 4/1990 | Berggren et al. |
| 4,950,227 A | 8/1990 | Savin et al. .................... 604/8 |
| 5,067,957 A | 11/1991 | Jervis |
| 5,078,736 A | 1/1992 | Behl |
| 5,156,613 A | 10/1992 | Sawyer |
| 5,190,546 A | 3/1993 | Jervis |
| 5,234,447 A | 8/1993 | Kaster et al. |
| 5,391,156 A | 2/1995 | Hildwein et al. |
| 5,405,322 A | 4/1995 | Lennox et al. |
| 5,443,497 A | 8/1995 | Venbrux |
| 5,503,635 A | 4/1996 | Sauer et al. |
| 5,571,167 A | 11/1996 | Maginot |
| 5,591,226 A | 1/1997 | Trerotola et al. |
| 5,597,378 A | 1/1997 | Jervis |
| 5,628,784 A | 5/1997 | Strecker |
| 5,657,429 A | 8/1997 | Wang et al. |
| 5,665,117 A | 9/1997 | Rhodes |
| 5,669,934 A | 9/1997 | Sawyer |
| 5,676,670 A | 10/1997 | Kim |
| 5,690,675 A | 11/1997 | Sawyer et al. |
| 5,695,504 A | 12/1997 | Gifford, III et al. |
| 5,697,968 A | 12/1997 | Rogers et al. |
| 5,702,418 A | 12/1997 | Ravenscroft |
| 5,713,917 A | 2/1998 | Leonhardt et al. |
| 5,720,755 A | 2/1998 | Dakov ........................ 606/139 |
| 5,725,544 A | 3/1998 | Rygaard |
| 5,728,133 A | 3/1998 | Kontos |
| 5,749,375 A | 5/1998 | Maginot |
| 5,749,895 A | 5/1998 | Sawyer et al. |
| 5,755,775 A | 5/1998 | Trerotola et al. |
| 5,755,778 A | 5/1998 | Kleshinski |
| 5,762,458 A | 6/1998 | Wang et al. |
| 5,779,718 A | 7/1998 | Green et al. |
| 5,797,920 A | 8/1998 | Kim |
| 5,797,934 A | 8/1998 | Rygaard |
| 5,810,884 A | 9/1998 | Kim |
| 5,814,005 A | 9/1998 | Barra et al. |
| 5,824,015 A | 10/1998 | Sawyer |
| 5,861,003 A | 1/1999 | Latson et al. |
| 5,868,759 A | 2/1999 | Peyser et al. |
| 5,868,761 A | 2/1999 | Nicholas et al. |
| 5,868,770 A | 2/1999 | Rygaard |
| 5,871,536 A | 2/1999 | Lazarus |
| 5,931,842 A | 8/1999 | Goldsteen et al. |
| 5,934,286 A | 8/1999 | Maginot |
| 5,938,672 A | 8/1999 | Nash |
| 5,938,696 A | 8/1999 | Goicoechea et al. |
| 5,944,019 A | 8/1999 | Knudson et al. |
| 5,944,730 A | 8/1999 | Nobles et al. |
| 5,944,738 A | 8/1999 | Amplatz et al. |
| 5,944,750 A | 8/1999 | Tanner et al. |
| 5,954,735 A | 9/1999 | Rygaard |
| 5,957,940 A | 9/1999 | Tanner et al. |
| 5,964,782 A | 10/1999 | Lafontaine et al. |
| 5,968,053 A | 10/1999 | Revelas |
| 5,968,089 A | 10/1999 | Krajicek |
| 5,968,090 A | 10/1999 | Ratcliff et al. |
| 5,972,017 A | 10/1999 | Berg et al. |
| 5,972,023 A | 10/1999 | Tanner et al. |
| 5,976,178 A | 11/1999 | Goldsteen et al. |
| 5,979,455 A | 11/1999 | Maginot |
| 5,984,955 A | 11/1999 | Wisselink |
| 5,989,276 A | 11/1999 | Houser et al. |
| 5,989,287 A | 11/1999 | Yang et al. |
| 5,993,468 A | 11/1999 | Rygaard |
| 6,001,124 A | 12/1999 | Bachinski |
| 6,004,347 A | 12/1999 | McNamara et al. |
| 6,007,576 A | 12/1999 | McClellan |
| 6,010,529 A | 1/2000 | Herweck et al. |
| 6,017,352 A | 1/2000 | Nash et al. .................. 606/153 |
| 6,019,788 A | 2/2000 | Butters et al. .................. 623/1 |
| 6,030,370 A | 2/2000 | Kupka et al. ............... 604/264 |
| 6,030,392 A | 2/2000 | Dakov ........................ 606/153 |
| 6,030,395 A | 2/2000 | Nash et al. |
| 6,036,702 A | 3/2000 | Bachinski et al. |
| 6,036,703 A | 3/2000 | Evans et al. .................. 606/153 |
| 6,036,705 A | 3/2000 | Nash et al. .................. 606/153 |
| 6,048,362 A | 4/2000 | Berg ......................... 623/1.34 |
| 6,056,762 A | 5/2000 | Nash et al. |
| 6,059,824 A | 5/2000 | Taheri |
| 6,063,114 A | 5/2000 | Nash et al. |
| 6,068,654 A | 5/2000 | Berg et al. |
| 6,071,305 A | 6/2000 | Brown et al. |
| 6,074,416 A | 6/2000 | Berg et al. |
| 6,095,997 A * | 8/2000 | French et al. ................... 604/9 |
| 6,113,612 A | 9/2000 | Swanson et al. |
| 6,117,147 A | 9/2000 | Simpson et al. |
| 6,120,432 A | 9/2000 | Sullivan et al. |
| 6,149,681 A | 11/2000 | Houser et al. |
| 6,293,955 B1 | 9/2001 | Houser et al. |
| 2002/0022891 A1 * | 2/2002 | Chevillon et al. ........ 623/23.64 |

FOREIGN PATENT DOCUMENTS

| | | |
|---|---|---|
| WO | WO 97/16122 | 5/1997 |
| WO | WO 97/27893 | 8/1997 |
| WO | WO 97/27897 | 8/1997 |
| WO | WO 97/27898 | 8/1997 |
| WO | WO 97/31575 | 9/1997 |
| WO | WO 97/40754 | 11/1997 |
| WO | WO 97/43961 | 11/1997 |
| WO | WO 98/03118 | 1/1998 |
| WO | WO 98/06356 | 2/1998 |
| WO | WO 98/07399 | 2/1998 |
| WO | WO 98/08456 | 3/1998 |
| WO | WO 98/19608 | 5/1998 |
| WO | WO 98/19618 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19635 | 5/1998 |
| WO | WO 98/19636 | 5/1998 |
| WO | WO 98/19732 | 5/1998 |
| WO | WO 98/19625 A2 A3 | 5/1998 |
| WO | WO 98/38939 | 9/1998 |
| WO | WO 98/38941 | 9/1998 |
| WO | WO 98/40036 A1 | 9/1998 |
| WO | WO 98/42262 | 10/1998 |
| WO | WO 98/52474 A1 | 11/1998 |
| WO | WO 98/55027 | 12/1998 |
| WO | WO 98/57590 | 12/1998 |
| WO | WO 98/57591 | 12/1998 |
| WO | WO 98/57592 | 12/1998 |
| WO | WO 99/00055 A2 A3 | 1/1999 |
| WO | WO 99/18887 | 4/1999 |
| WO | WO 99/38454 | 8/1999 |
| WO | WO 99/45852 | 9/1999 |
| WO | WO 99/48427 A1 | 9/1999 |
| WO | WO 99/62408 | 12/1999 |
| WO | WO 99/62415 | 12/1999 |
| WO | WO 99/63910 A1 | 12/1999 |
| WO | WO 99/65409 A1 | 12/1999 |
| WO | WO 00/09040 | 2/2000 |
| WO | WO 00/15144 A1 | 3/2000 |
| WO | WO 00/24339 | 5/2000 |
| WO | WO 00/27311 A1 | 5/2000 |
| WO | WO 00/27313 A2 A3 | 5/2000 |
| WO | WO 00/40176 A1 | 7/2000 |
| WO | WO 00/53104 A1 | 9/2000 |
| WO | WO 01/41653 A2 A3 | 6/2001 |

* cited by examiner

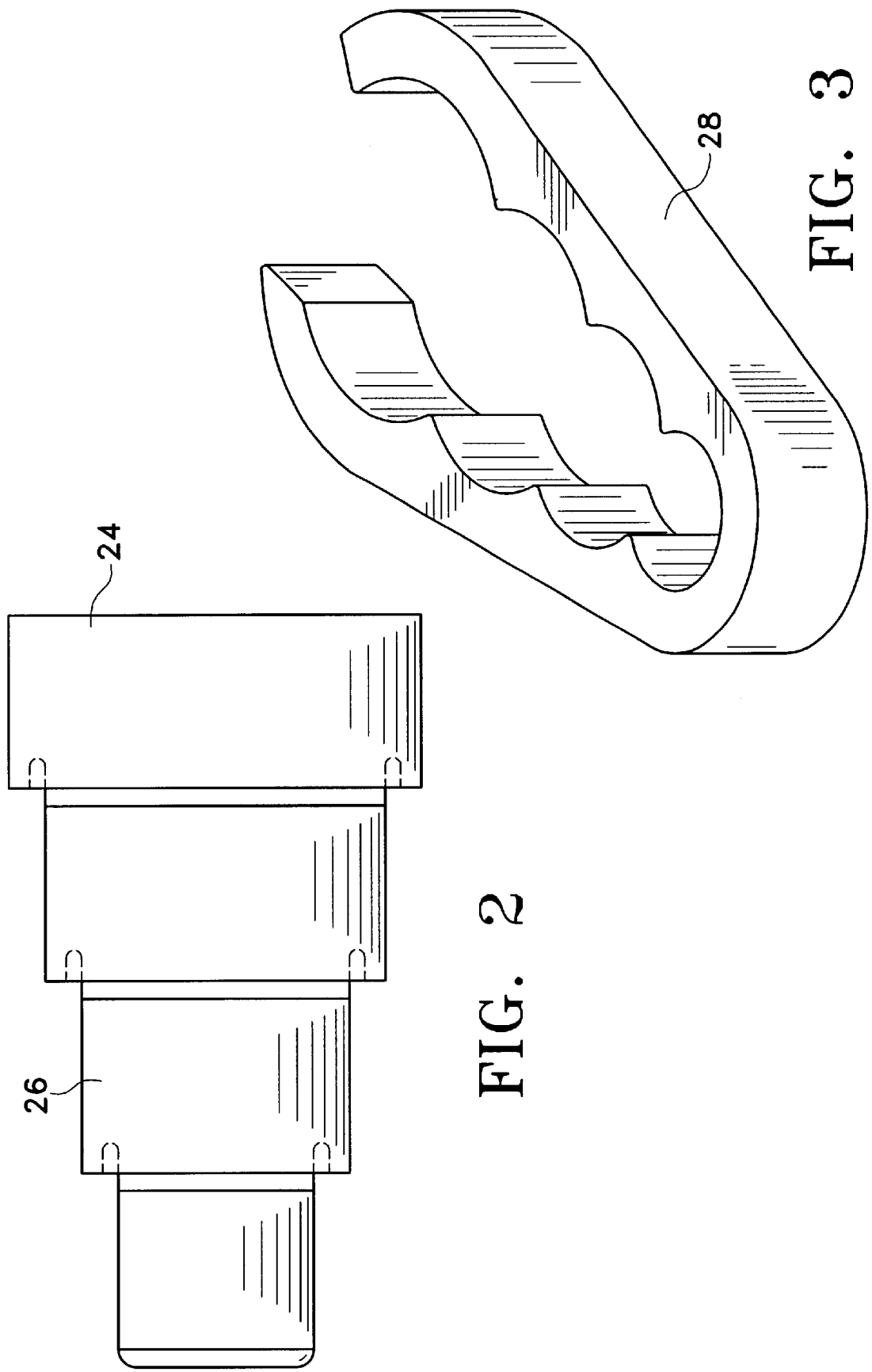

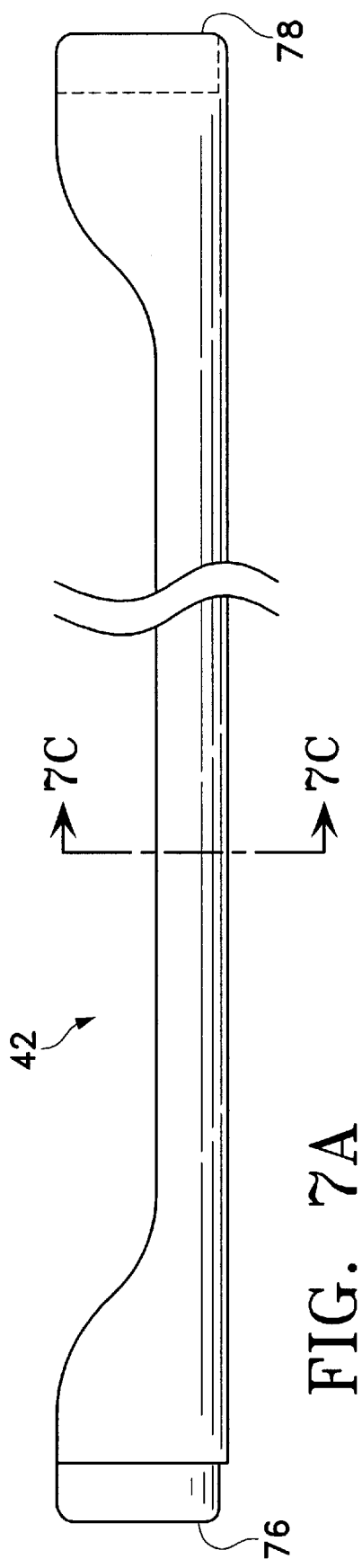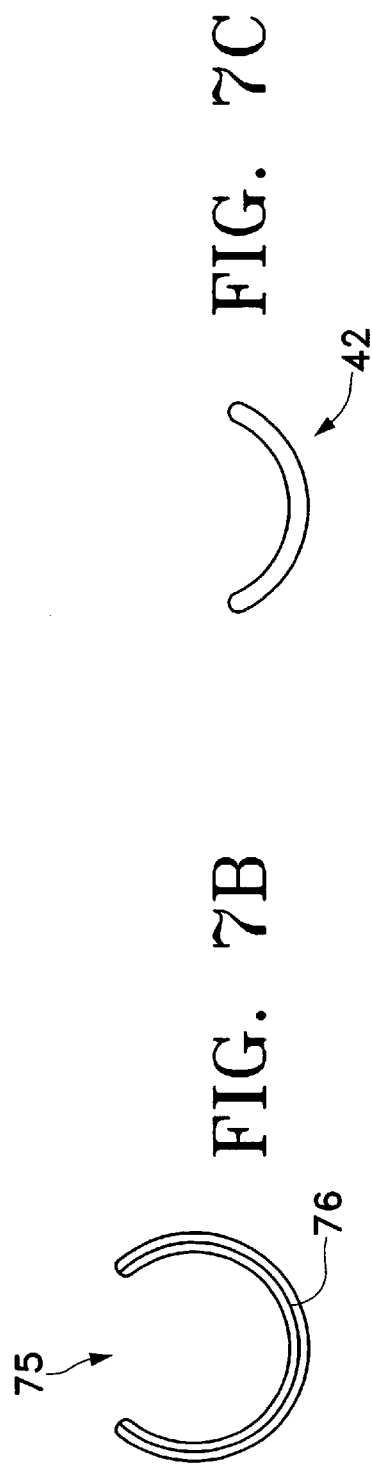

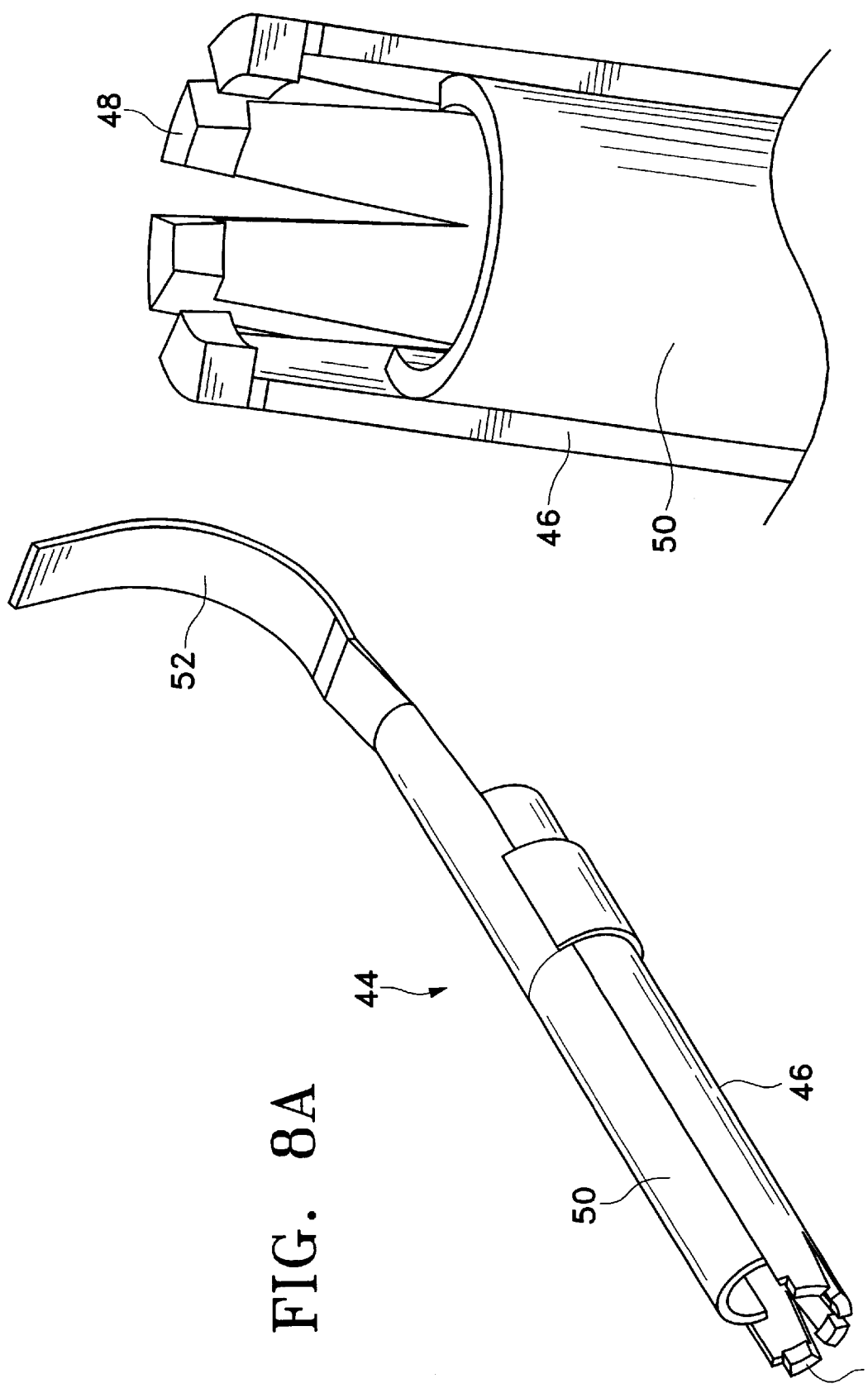

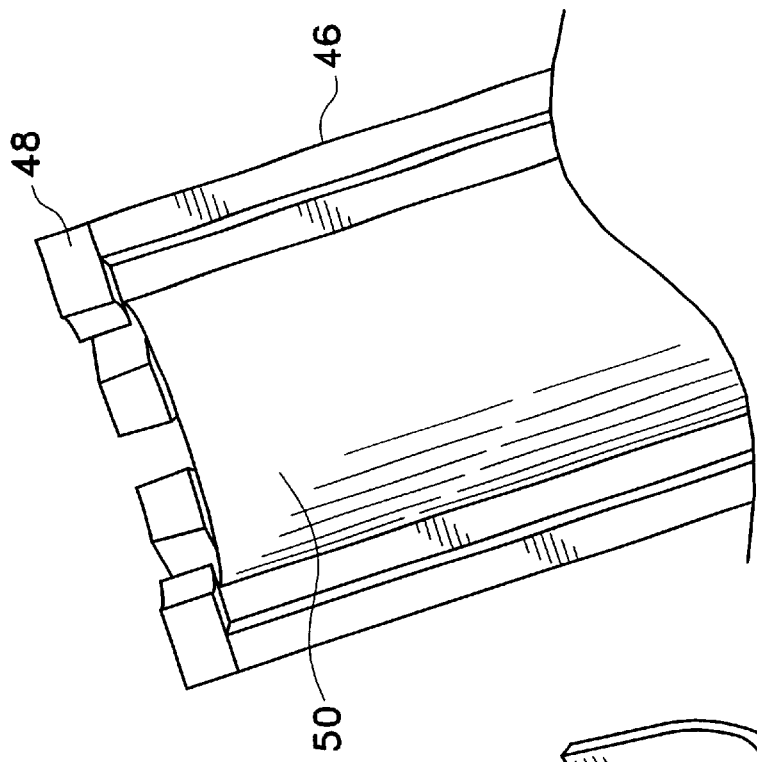
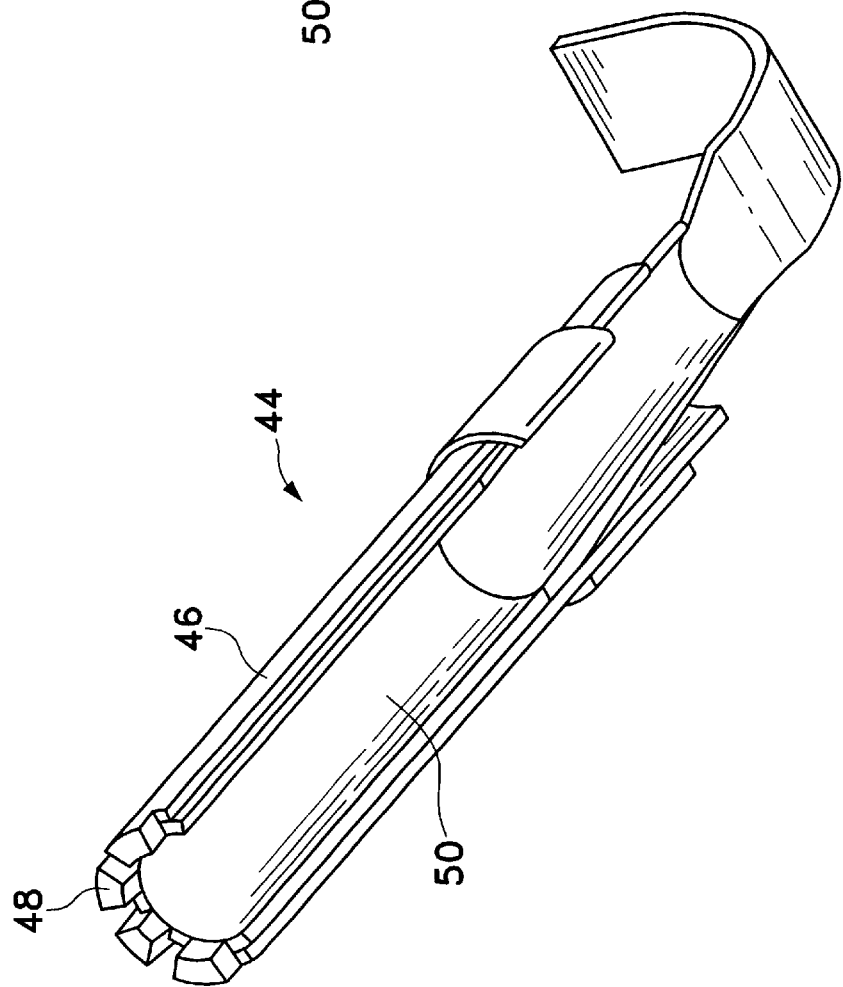
FIG. 8F
FIG. 8E

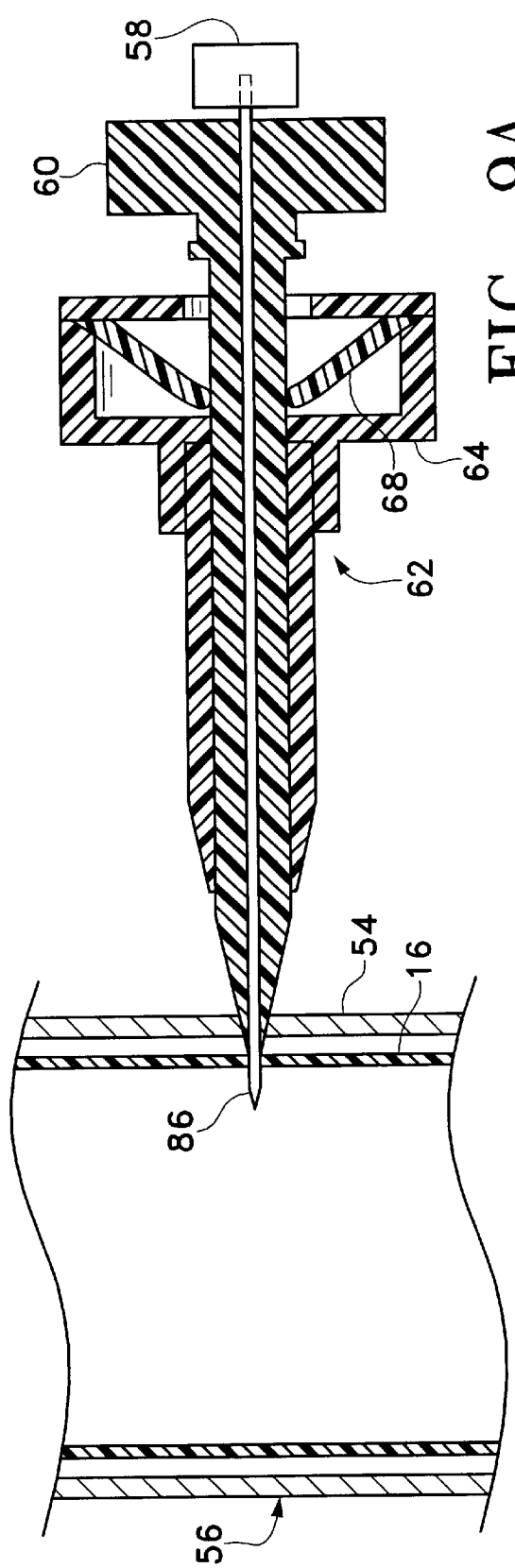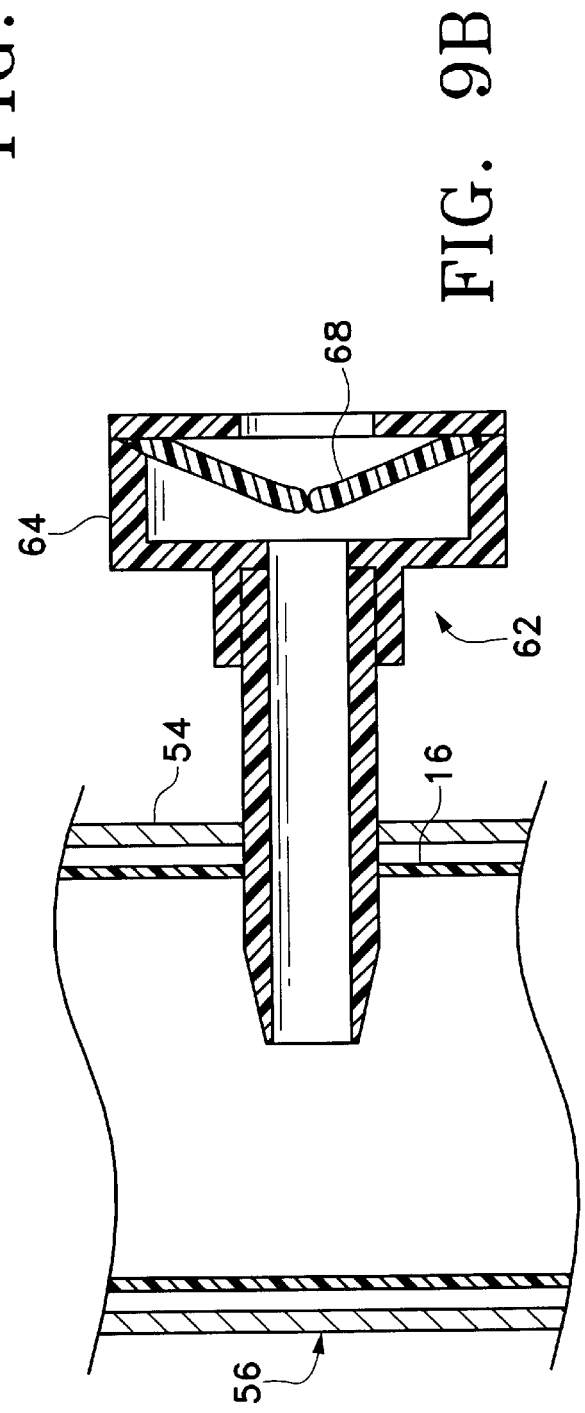
FIG. 9A
FIG. 9B

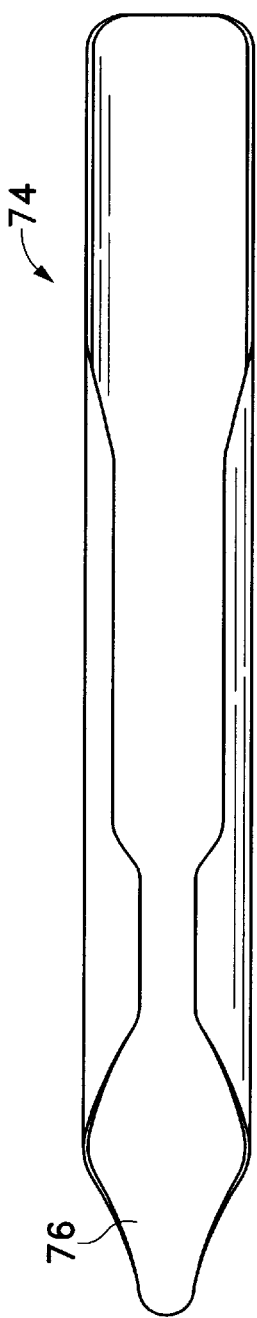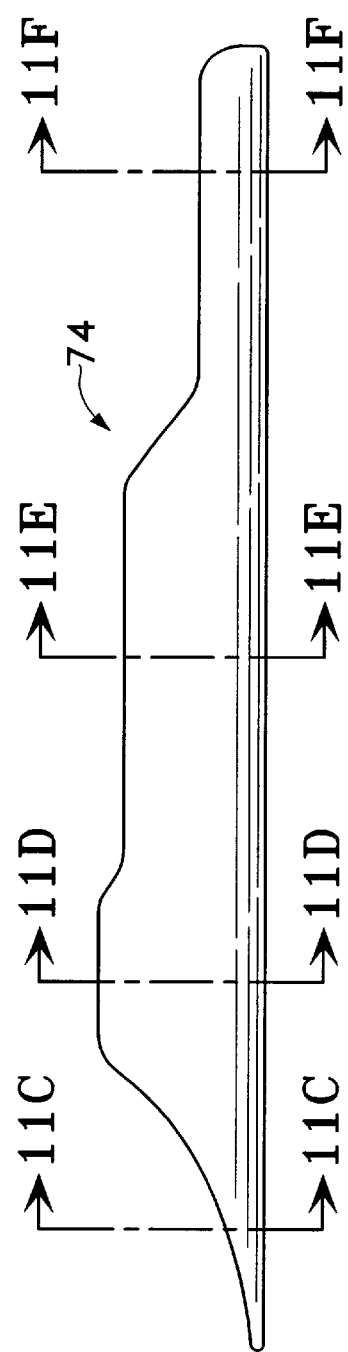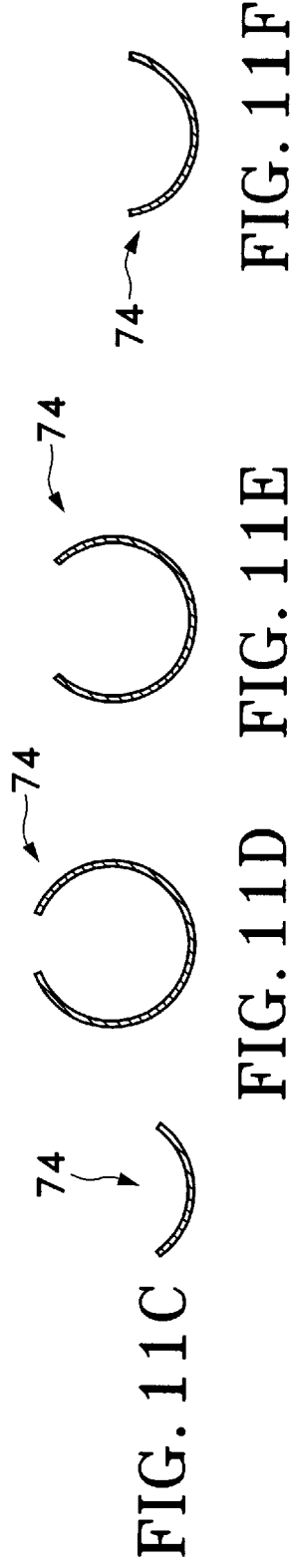
FIG. 11A  FIG. 11B  FIG. 11C  FIG. 11D  FIG. 11E  FIG. 11F

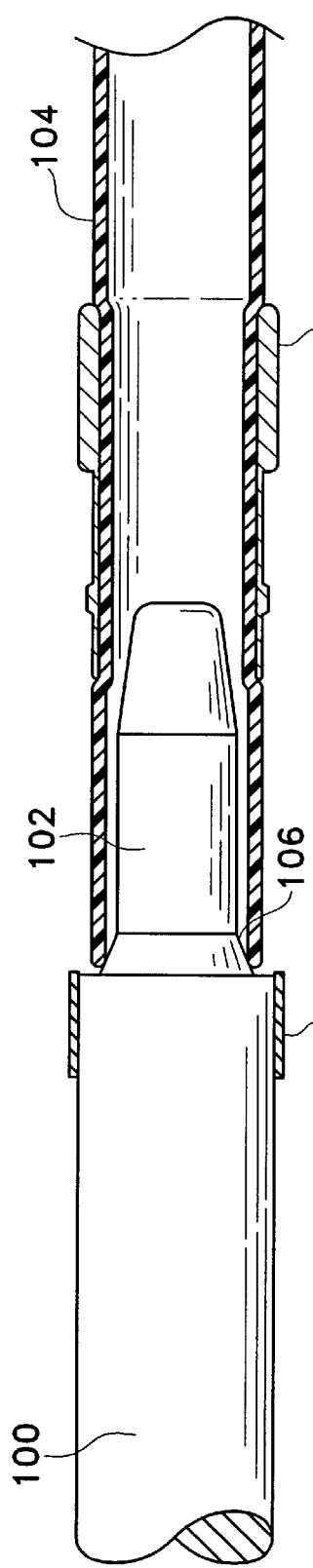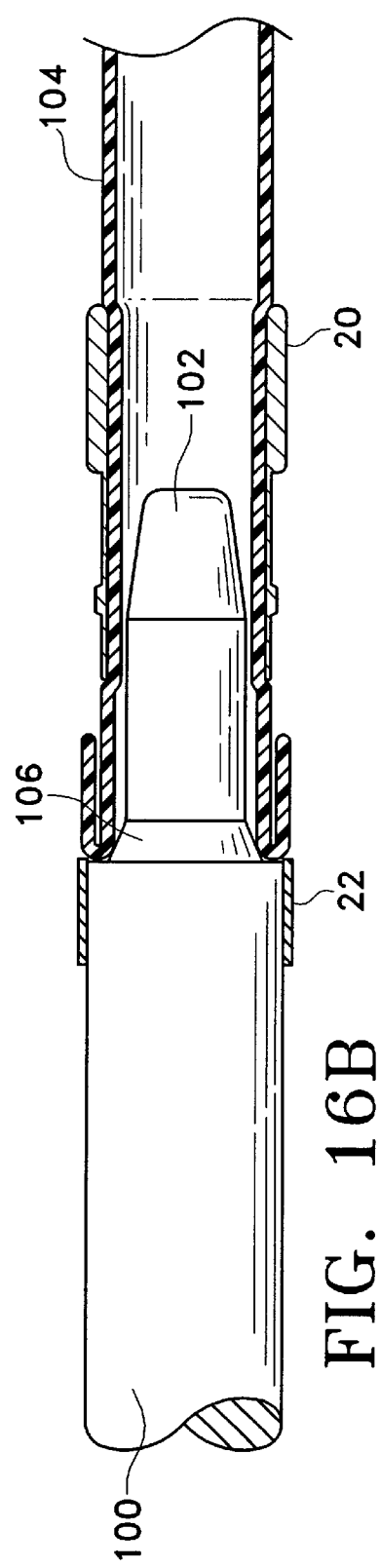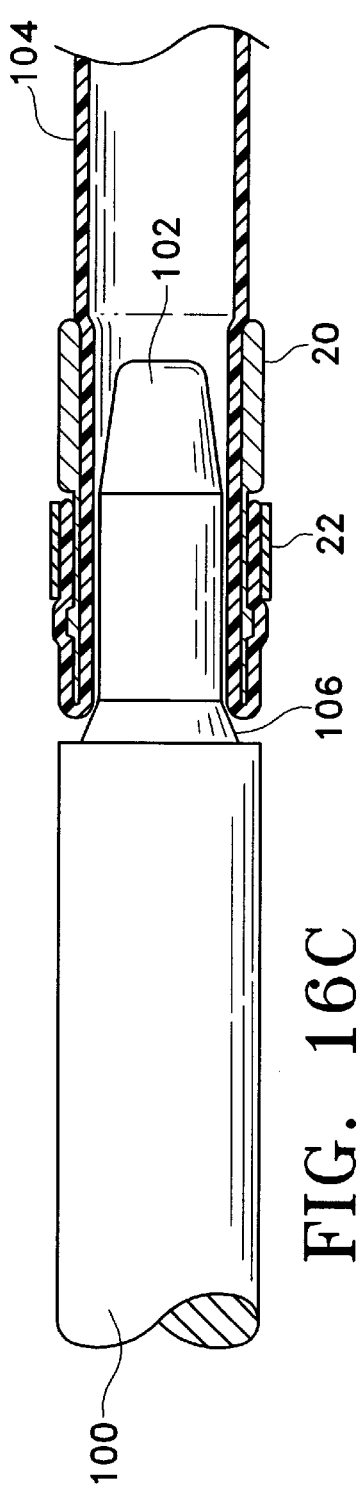

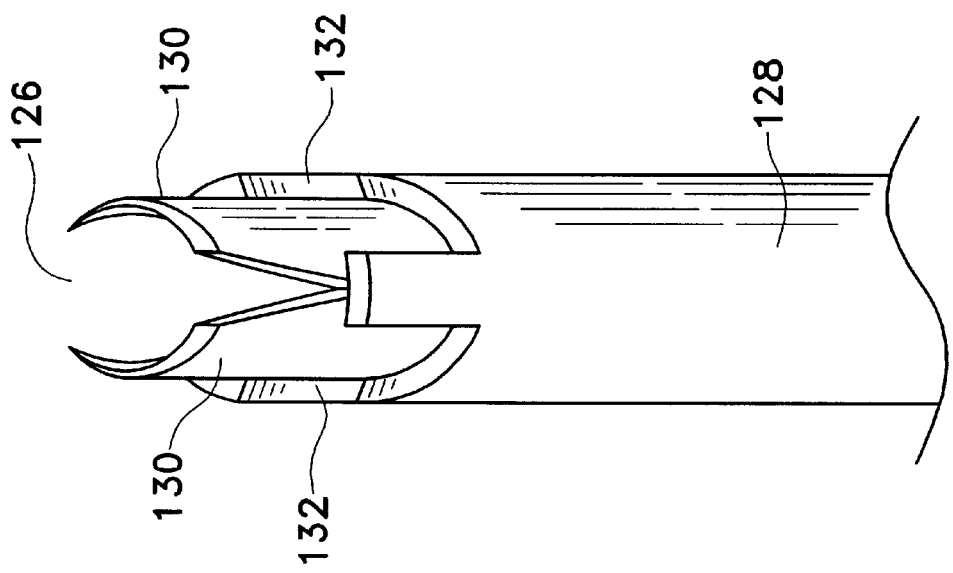
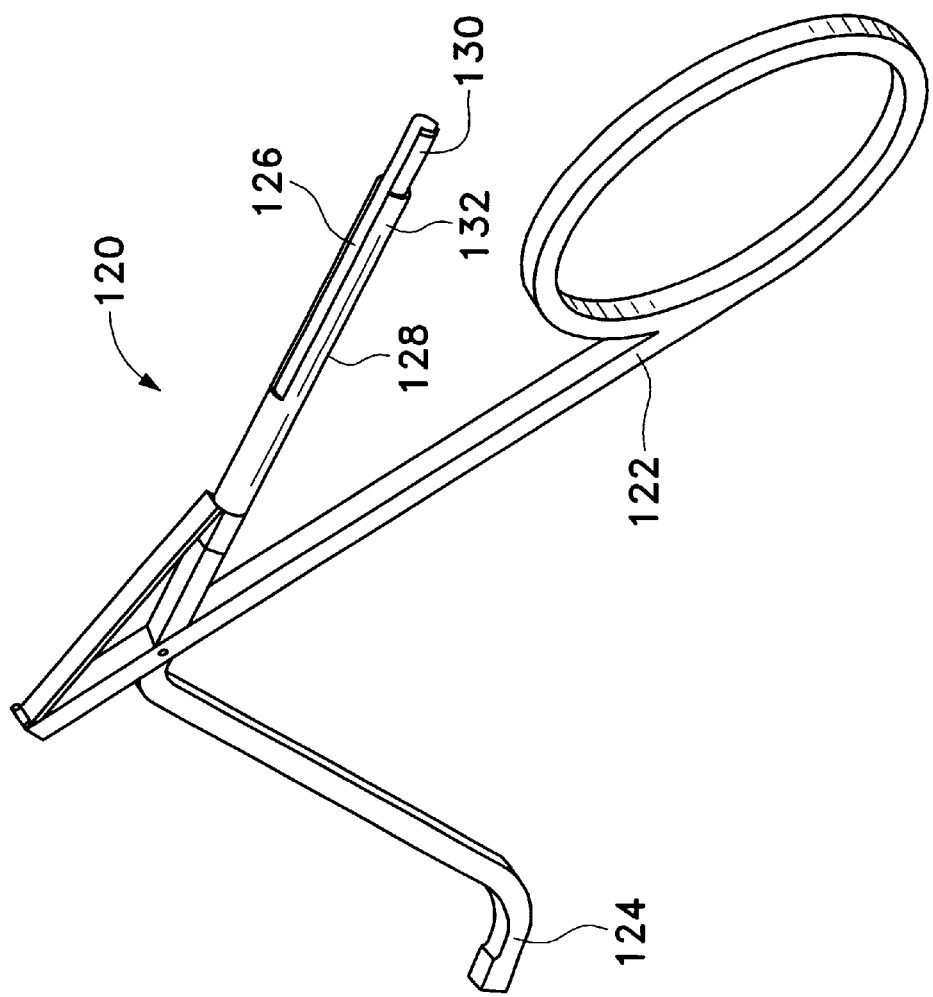
FIG. 19B
FIG. 19A

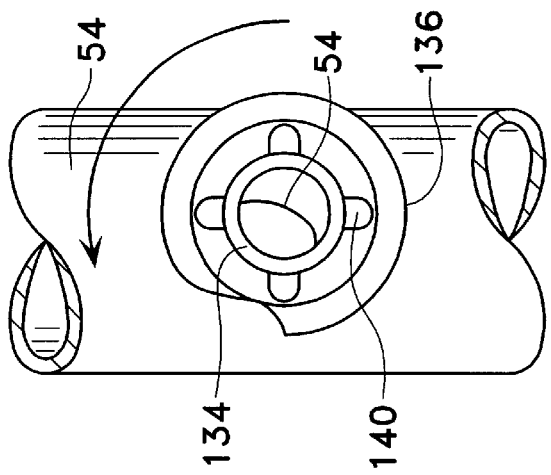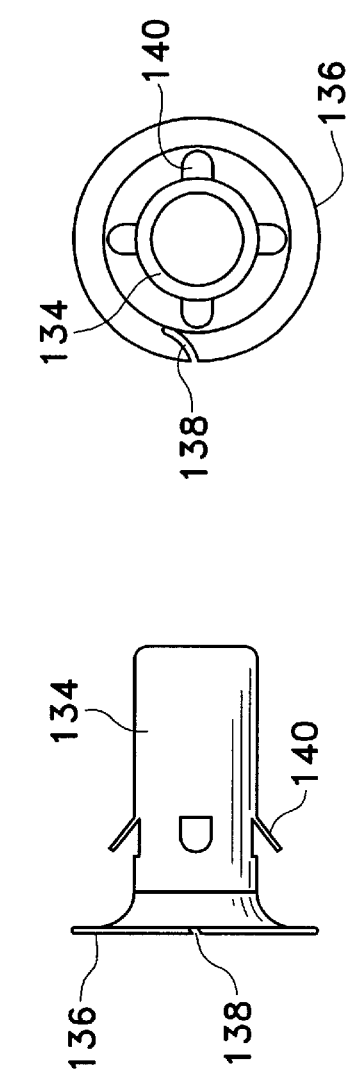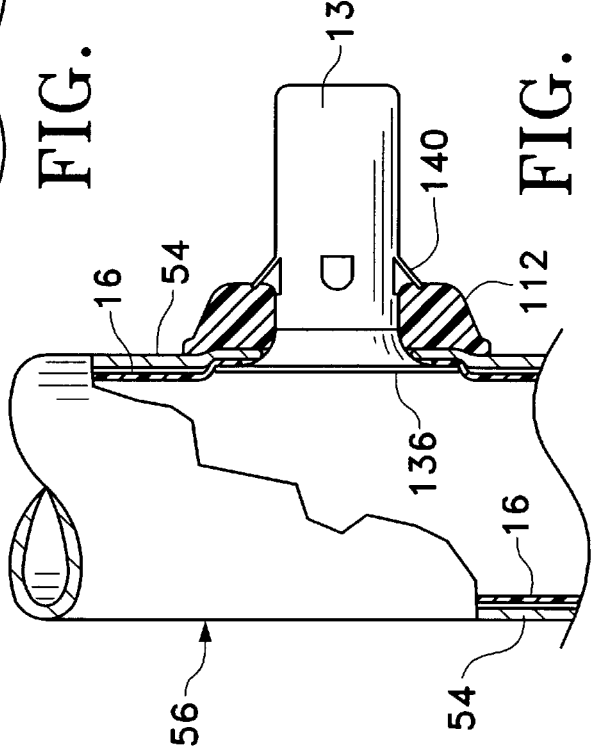

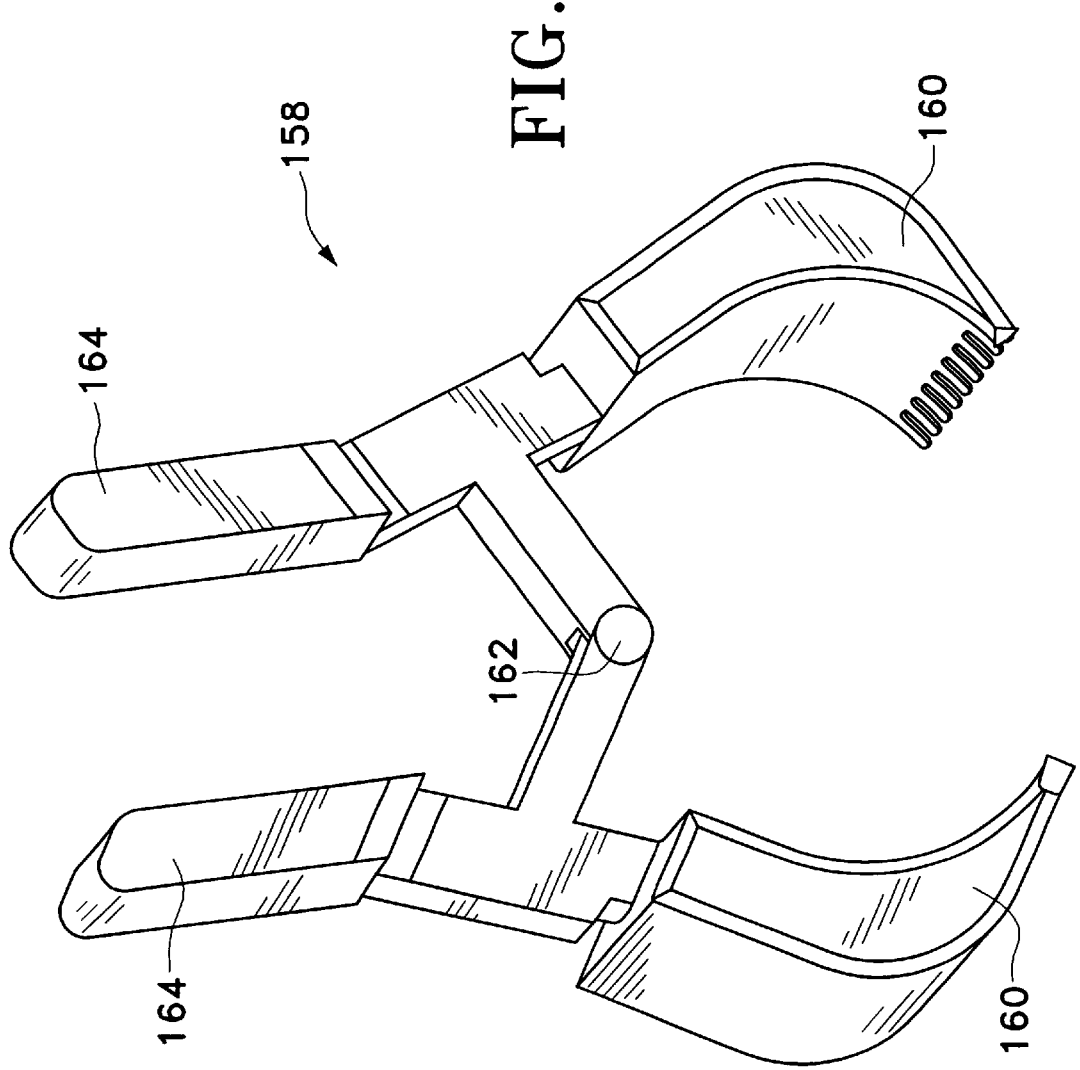

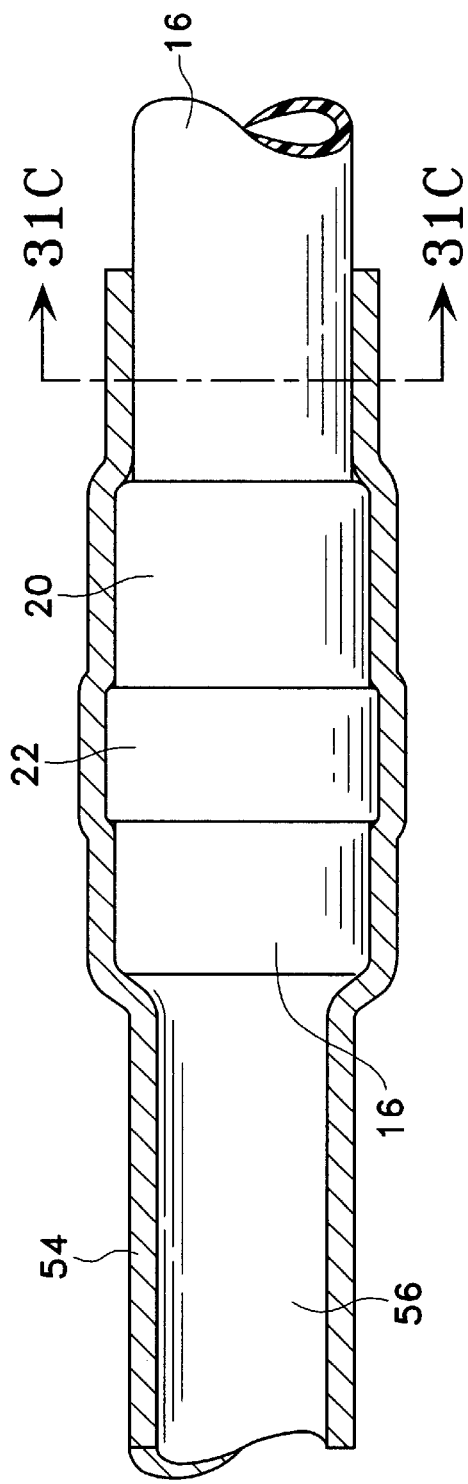
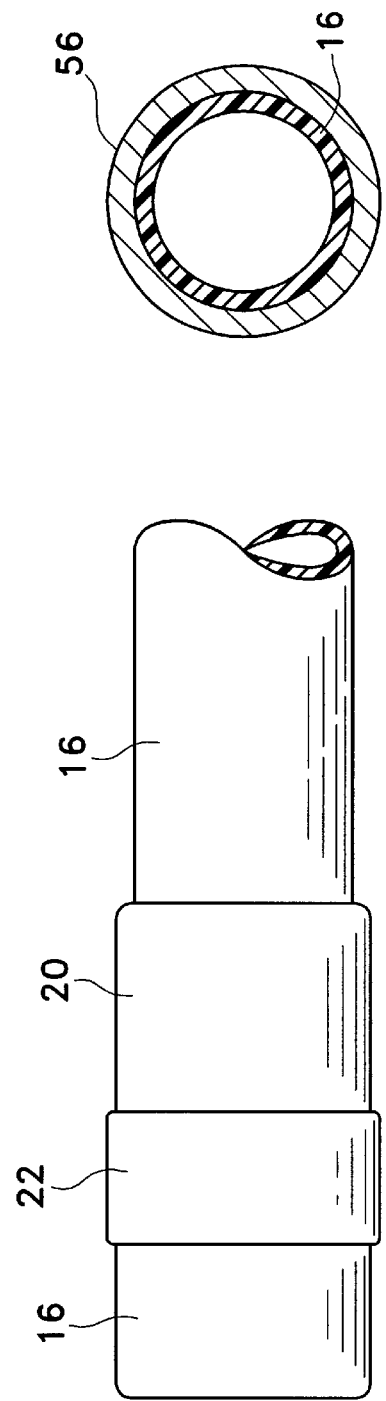
FIG. 31A
FIG. 31B
FIG. 31C

AORTIC ANEURYSM TREATMENT SYSTEMS

This application claims the benefit of U.S. Provisional Patent Application Ser. No. 60/088,705, entitled "Bypass Graft Mechanical Securing Systems", filed Jun. 10, 1998, and U.S. Provisional Patent Application Ser. No. 60/111,948, entitled "Bypass Graft Positioning and Securing Systems", filed Dec. 11, 1998.

BACKGROUND OF THE INVENTION

This invention relates to devices and processes for treating aortic aneurysms (abdominal aortic aneurysms, thoracic aortic aneurysms, and thoracoabdominal aortic aneurysms). More particularly, the invention relates to devices and techniques for securing a graft to reinforce the aorta and reattach branching vessels that would otherwise be occluded. In addition, the invention addresses other treatment modalities involving reattaching branching vessels to the reinforcing graft. These include aortic root replacements for aortic dissections in which the left and right coronary arteries must be reattached to the replacement graft, and extracranial carotid aneurysm repair involving reattaching the internal carotid artery and/or the external carotid artery to a replacement graft. More particularly, this invention applies to all aneurysm treatment regimens involving attaching a reinforcing graft or replacement graft to isolate or remove the aneurysm and reattach branching vessels that would otherwise be occluded or separated. Embodiments of the invention enable rapidly securing grafts to the vasculature without the need to suture the graft to the host vessel wall, or to stop or re-route blood flow through the host vessel to reattach branching vessels.

Current techniques for producing anastomoses during aortic aneurysm procedures involve interrupting blood flow for a prolonged period of time to suture, clip, or staple a graft to the aorta. Interrupting blood flow is associated with substantial morbidity and mortality. Less invasive attempts at treating aortic aneurysms involve percutaneously deploying grafts into the abdominal aorta or thoracic aorta and securing the grafts with hooks or stents. Most of these less invasive approaches occlude blood flow while balloon catheters are used to position and expand the securing components into contact with the vessel. In addition, these approaches do not address branching vessels that can be occluded when grafts extend past the branching vessels to isolate the aneurysm from blood flow.

Attempts to automate formation of sutureless anastomoses have led to mechanical stapling devices. Mechanical stapling devices have been proposed for creating end-end anastomoses between the open ends of transected vessels. Berggren et al. propose an automatic stapling device for use in microsurgery (U.S. Pat. Nos. 4,607,637, 4,624,257, 4,917,090, and 4,917,091). This stapling device has mating sections containing pins that are locked together after the vessel ends are fed through lumens in the sections and everted over the pins. This stapling device maintains intima-to-intima apposition for the severed vessel ends but has a large profile and requires impaling the everted vessel wall with the pins. Sakura describes a mechanical end-end stapling device designed to reattach severed vessels (U.S. Pat. No. 4,214,587). This device has a wire wound into a zig-zag pattern to permit radial motion and contains pins bonded to the wire that are used to penetrate tissue. One vessel end is everted over and secured to the pins of the end-end stapling device, and the other vessel end is advanced over the end-end stapling device and attached with the pins. Sauer et al. proposes another mechanical end-end device that inserts mating pieces into each open end of a severed vessel (U.S. Pat. No. 5,503,635). Once positioned, the mating pieces snap together thereby bonding the vessel ends. These end-end devices are amenable to reattaching severed vessels but are not suitable to producing end-end anastomoses between a graft and an intact vessel, especially when exposure to the vessel is limited.

Mechanical stapling devices have also been proposed for end-side anastomoses. These devices are designed to insert bypass grafts, attached to the mechanical devices, into the host vessel through a large incision and secure the bypass graft to the host vessel. Kaster describes vascular stapling apparatus for producing end-side anastomoses (U.S. Pat. Nos. 4,366,819, 4,368,736, and 5,234,447). Kaster's end-side apparatus is inserted through a large incision in the host vessel wall. The apparatus has an inner flange that is placed against the interior of the vessel wall, and a locking ring that is affixed to the fitting and contains spikes that penetrate into the vessel thereby securing the apparatus to the vessel wall. The bypass graft is itself secured to the apparatus in the everted or non-everted position through the use of spikes incorporated in the apparatus design.

U.S. Surgical has developed automatic clip appliers that replace suture stitches with clips (U.S. Pat. Nos. 5,868,761, 5,868,759, and 5,779,718). These clipping devices have been demonstrated to reduce the time required when producing the anastomosis but still involve making a large incision through the host vessel wall. As a result, blood flow through the host vessel must be interrupted while creating the anastomoses.

Gifford et al. provides end-side stapling devices (U.S. Pat. No. 5,695,504) that secure harvested vessels to host vessel walls maintaining intima to intima apposition. This stapling device is also inserted through a large incision in the host vessel wall and uses staples incorporated in the device to penetrate into tissue and secure the bypass graft to the host vessel.

Walsh et al. proposes a similar end-side stapling device (U.S. Pat. Nos. 4,657,019, 4,787,386, and 4,917,087). This end-side device has a ring with tissue piercing pins. The bypass graft is everted over the ring; then, the pins penetrate the bypass graft thereby securing the bypass graft to the ring. The ring is inserted through a large incision created in the host vessel wall and the tissue piercing pins are used to puncture the host vessel wall. A clip is then used to prevent dislodgment of the ring relative to the host vessel.

The previously described end-side stapling devices require insertion through a large incision, which dictates that blood flow through the host vessel must be interrupted during the process. Even so, these and other clipping and stapling end-side anastomotic devices require significant time to create the anastomosis. Interruption of blood flow for a prolonged period of time increases the morbidity and mortality of grafting procedures, especially during aortic aneurysm repair.

A need thus exists for fittings, grafts, and delivery systems capable of quickly producing an anastomosis between a graft and a host vessel or reattaching branching vessels with minimal interruption of blood flow. These anastomoses must withstand the pressure exerted by the pumping heart and ensure blood does not leak from the anastomoses into the thoracic cavity, abdominal cavity, or other region exterior to the vessel wall. In addition, these anastomoses must prevent dislodgment even when the graft is subject to external forces or motion of the aorta.

SUMMARY OF THE INVENTION

The invention provides systems and components for improved treatment for aneurysms that extend to bifurcations and/or envelop branching vessels, especially aortic aneurysms. The systems enable a physician to quickly and accurately position and secure a reinforcing graft. In addition, the invention provides processes to reattach branching vessels to a reinforcing graft positioned within and secured to a host vessel while minimizing the interruption of blood flow to the branching vessel during the procedure.

The invention provides extension grafts that are configured to lengthen a branching vessel or other host vessel which may be too short to reach the desired anastomosis site. The extension grafts also provide a mechanism to expedite reattaching the branching vessel to the reinforcing graft or reestablish blood flow to a branching vessel without the need to cut the branching vessel. The invention includes reinforcing grafts that incorporate branches containing end-end fittings inserted into and secured to branching vessels without cutting the branching vessels.

End-end fittings are provided to secure reinforcing grafts or extension grafts to host vessels. Once positioned within the host vessel, the end-end fittings are secured to the host vessel by compressing the host vessel against the end-end fitting using retaining rings, strands of suture, or stitches placed around the host vessel at the end-end fitting interface.

The invention provides end-side fittings capable of securing branching vessels or extension grafts to the side of a reinforcing graft and/or host vessel. The end-side fitting embodiments can be configured to produce anastomoses between branching vessels and host vessels such that only the endothelial layer of the branching vessel is exposed to blood flow. In addition, end-side fitting embodiments are provided that do not require a delivery system to insert the end-side fitting through the reinforcing graft wall and/or host vessel wall.

The delivery systems of the invention enable inserting an end-side fitting,and branching vessel combination or an extension graft through a host vessel wall, and in many cases also a reinforcing graft, without interrupting blood flow through the host vessel. In addition, the delivery systems of the invention enable inserting a reinforcing graft through a host vessel wall. One delivery system embodiment is a combination of a tear-away sheath, dilator, guidewire, and needle designed to be inserted into the host vessel at the desired anastomosis site. The fitting and branching vessel combination is inserted through the tear-away sheath into the interior of the host vessel. After reattaching the branching vessel, the hub and valve of the tear-away sheath are split and the sheath is then separated and removed from around the branching vessel. A plunger is used to insert the branching vessel and fitting combination through the sheath and past the host vessel wall and graft wall. The plunger also protects the branching vessel during insertion, especially when advancing past the hemostatic valve.

An alternative delivery system involves advancing a fitting directly through a puncture in the host vessel wall and graft without stopping or re-routing blood flow. The fitting is partially inserted through an incision and rotated past the host vessel wall and graft, into the interior of the host vessel. Optionally, a guidewire can serve as a passage to rotate and advance the fitting past the host vessel wall and graft, and into the interior of the host vessel. Once inside the host vessel, the fitting is secured, thereby attaching the branching vessel to the host vessel.

Further features and advantages of the inventions will be elaborated in the detailed description and accompanying drawings.

BRIEF DESCRIPTION OF THE DRAWINGS

FIG. 2 shows a pin used to axially advance a retaining ring against an end-end fitting.

FIG. 3 shows a holder used to support the end-end fitting while advancing the retaining ring using the pin shown in FIG. 2.

FIGS. 7A to 7C are side, end, and cross-sectional views of a plunger.

FIGS. 8A to 8F show an alternative insertion device for advancing and retracting the fitting through vasculature.

FIGS. 9A to 9C show a delivery system provided in accordance with the invention.

FIGS. 11A to 11F show an alternative sheath embodiment of the delivery system.

FIGS. 16A to 16C show an everting tool.

FIGS. 19A and 19B show a compression tool designed to atraumatically advance a compression ring over an end-side fitting.

FIGS. 20A to 20E show an end-side fitting deliverable past a host vessel wall without the need for a sheath.

FIGS. 28A and 28B show a clamp and for temporarily closing incisions through a vessel wall.

FIGS. 31A to 31C show an end-end fitting for securing tubular structures to fittings.

DETAILED DESCRIPTION OF THE INVENTION

Figure 1A:
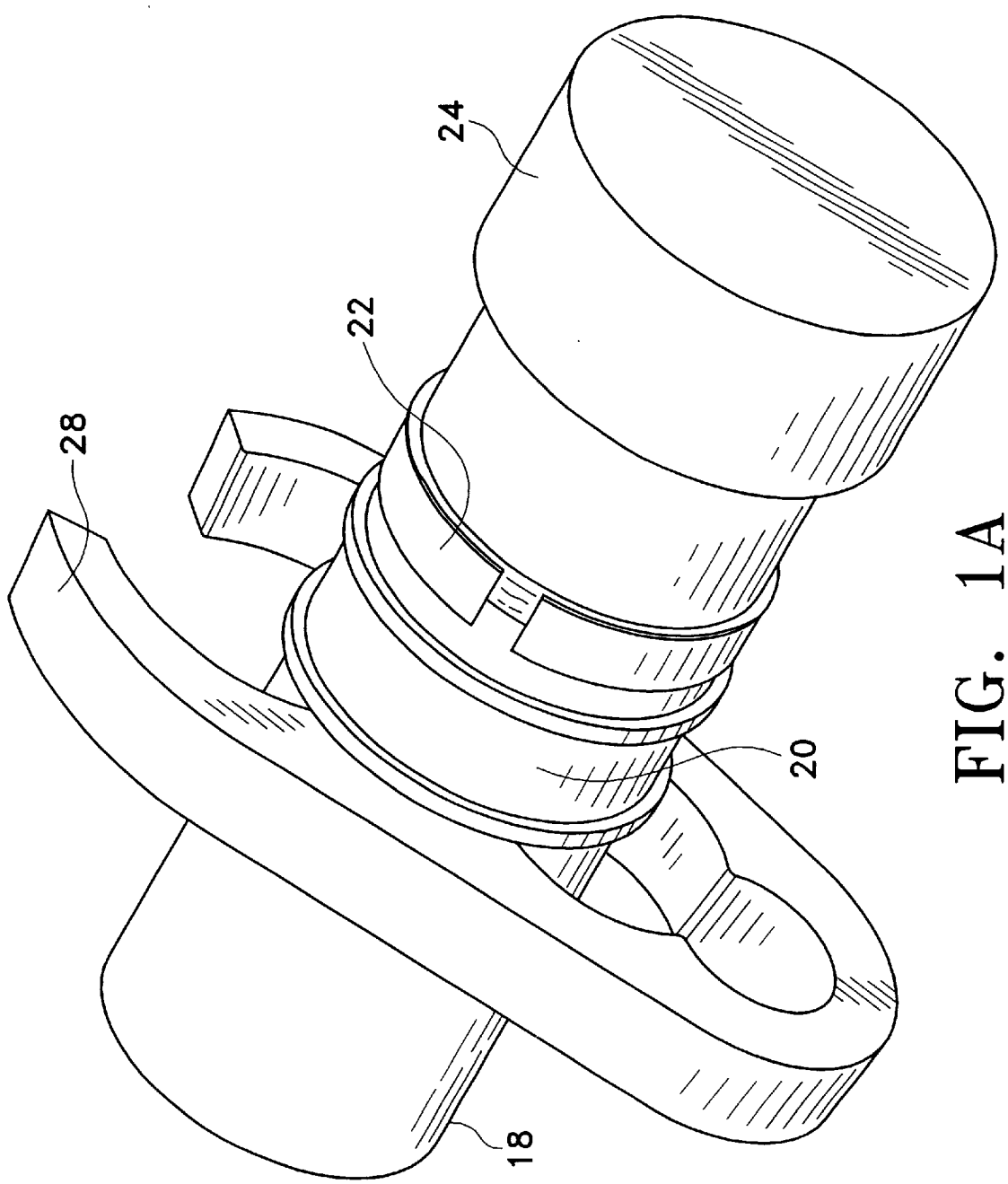
FIG. 1A to 1C show the securing of a tubular structure to an end-end fitting with a retaining ring by using the pin and holder shown in FIGS. 2 and 3, respectively.

The embodiments of the present invention are intended to rapidly produce anastomoses between reinforcing grafts (or replacement grafts) and host vessels to treat vascular abnormalities such as aneurysms, fistulas, or other surgical indications requiring a reinforcing graft. The embodiments of the invention also secure branching vessels to a reinforcing graft during surgical procedures in which the branching vessels would otherwise be occluded from blood flow (e.g. reattaching the renal arteries, mesenteric artery, celiac artery, and intercostal arteries during abdominal aortic aneurysm repair). The systems of the invention specifically address the problems of managing of abdominal aortic aneurysms, thoracic aortic aneurysms, and thoracoabdominal aortic aneurysms by mitigating risks of current surgical and percutaneous treatment modalities. In addition, the systems are useful in aortic root replacement procedures, extracranial carotid aneurysm repair, and other aneurysm treatments in which a reinforcing graft (or replacement graft) is secured to the host vessel and/or branching vessels are reattached to the host vessel.

The reinforcing grafts, replacement grafts, or extension grafts may be manufactured by extruding, injection molding, weaving, braiding, or dipping polymers such as polytetrafluoroethylene (PTFE), expanded PTFE, urethane, polyamide, polyimide, nylon, silicone, polyethylene, collagen, polyester (e.g., DACRON, manufactured by E.I. du Pont de Nemours and Company, Wilmington, DE), composites of these representative materials, or other suitable graft material. These materials may be fabricated using one or a combination of the stated manufacturing processes. The graft may be coated, deposited, or impregnated with materials, such as parylene, heparin solutions, hydrophilic solutions, or other substances designed to reduce thrombus formation. Reinforcing or replacement grafts may alternatively be a harvested vessel such as the saphenous vein.

Fittings

The fittings in accordance with the invention are designed to attach reinforcing grafts (or replacement grafts) to host vessels, attach extension grafts to host vessels, or reattach branching vessels to reinforcing grafts or host vessels. The fittings are constructed from a metal (e.g. titanium), alloy (e.g. stainless steel or nickel titanium), thermoplastic, thermoset plastic, silicone or combination of the aforementioned materials into a composite structure; other materials may alternatively be used. The fittings may be coated with materials such as parylene or other hydrophilic substrates that are biologically inert and reduce the surface friction. Alternatively, the fittings may be coated with heparin or thrombolytic substances designed to prevent thrombosis around the attachment point to the host vessel. The fittings consist of one or more components designed to secure a reinforcing graft to a host vessel, secure an extension graft to a reinforcing graft, attach an extension graft to a host vessel, or attach the ends of branching vessels to a reinforcing graft. Unless otherwise indicated, reference numeral 18 generically describes a graft, whether it be a reinforcing graft, an extension graft, or otherwise, while reference numeral 16 describes the wall of such a graft 18.

The fittings may be laminated between layers of graft material during fabrication of a synthetic graft, or may be secured to the reinforcing graft, the branching vessel, or the extension graft using a compression mechanism. FIG. 1C shows a reinforcing graft or an extension graft 18 having one end secured to an end-end fitting 20 by compressing the graft material between at least two components (e.g. the end-end fitting 20 and a retaining ring). These components may lock together as a result of the interference fit between the components with the graft material compressed between the components or may incorporate a separate locking mechanism.

Figure 1B:
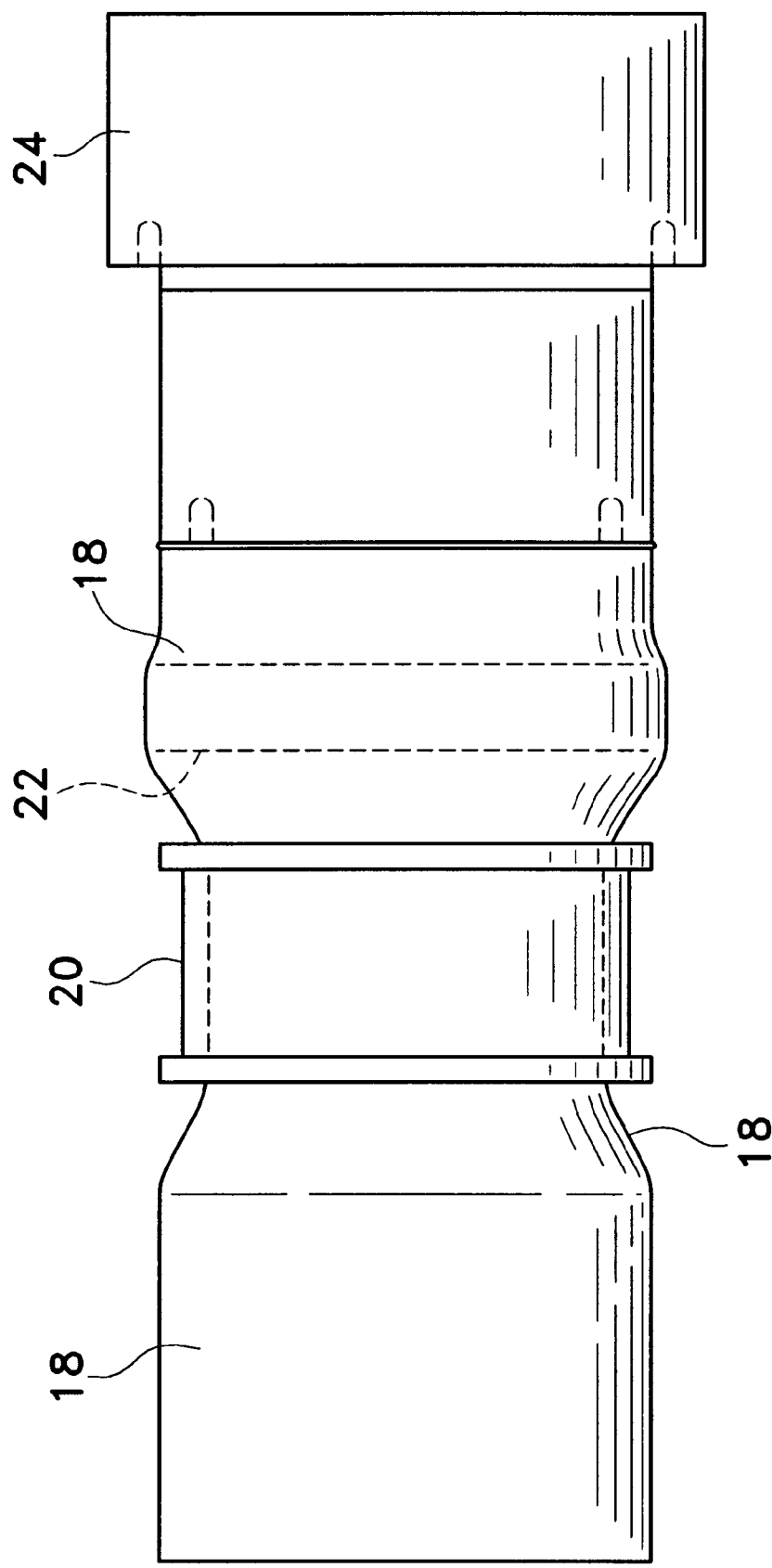
Figure 1C:
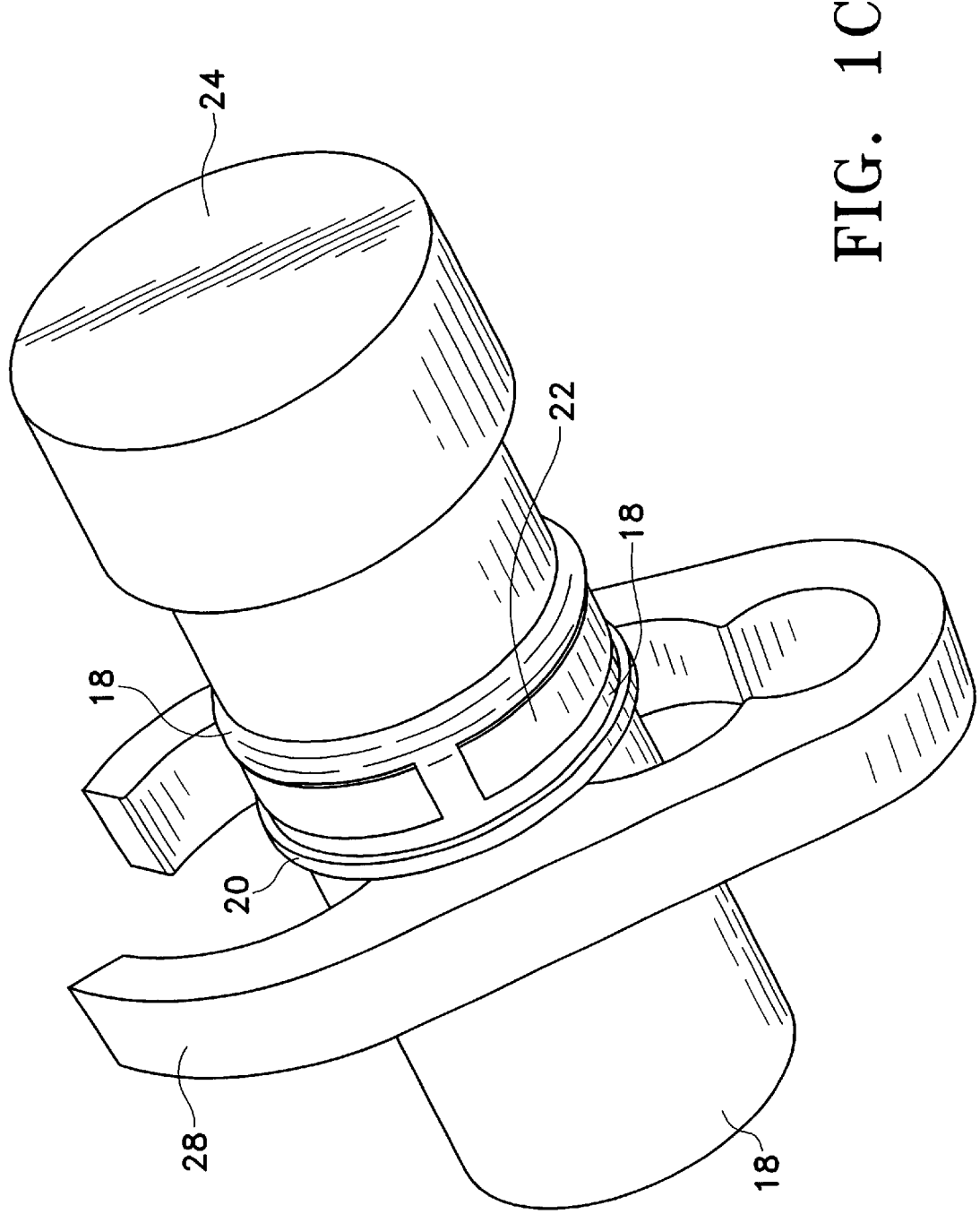

FIGS. 1A to 1C show the process of compressing a graft 18 or other tubular structure between an end-end fitting 20 and a retaining ring 22. As seen in FIG. 1B, graft 18 is inserted through the inner surface of end-end fitting 20 and is advanced over the outer surface of retaining ring 22. This enables everting the graft 18 over fitting 20. The graft also can be advanced over the outer surface of the end-end fitting and through the inner surface of the retaining ring (not shown). Alternatively, the graft may be advanced over the outer surface of the end-end fitting and the retaining ring may be advanced over the side of the end-end fitting (not shown). A pin 24, shown in FIG. 2, is advanced through the interior of the tubular structure from the end the retaining ring is to be advanced toward the end-end fitting. The pin accommodates various diameter rings. The ridges 26 of the pin are used to push the ring over the fitting and graft interface. An inner channel may be incorporated into pin 24. The inner channel allows the edge of the fitting and reinforcing graft combination to slide past the ridges so the ring can be placed a further distance onto the fitting and tubular structure interface. A holder 28, shown in FIG. 3, is placed over graft 18 abutting the fitting. The holder also accommodates various diameter grafts and fittings. Pin 24 is axially movable relative to holder 28 to permit advancing retaining ring 22 toward the end-end fitting 20. Retaining ring 22 shown in FIGS. 1A to 1C extends to less than a complete circle to permit expansion over the end-end fitting as the retaining ring is advanced. As seen in FIG. 1C, the graft 18 is everted as retaining ring 22 is advanced, using pin 24 and holder 28, over fitting 20. The end-end fitting includes a notch in which the retaining ring fits to prevent axial dislodgment of the retaining ring once positioned. Holder 28 and pin 24 may also be used to compress two fitting components that lock axially and do not need to overlap. This does not require everting the reinforcing graft over the end-end fitting.

Using a ring or other compression mechanism to attach the fitting (end-end or end-side) facilitates securing the fitting anywhere along the graft or branching vessel. The primary benefit of being able to selectively secure fitting 20 to the reinforcing graft, the branching vessel, or the extension graft is the ability to specify the desired length of the graft or vessel and attach the end-end fitting to that established parameter. This gives flexibility to determine the extent of the aneurysm before tailoring the reinforcing graft to support the affected vasculature, assess whether the branching vessel and fitting combination will sufficiently reach the host vessel, or evaluate the length of extension graft needed to extend from the end of the branching vessel to the host vessel. In addition, this enables using biological grafts obtained by harvesting vessels instead of synthetic graft materials.

An alternative method to tailor the length of the reinforcing graft or the extension graft, depending on physiologic differences, is to include end-end fittings at spaced intervals (e.g., 1 inch) along the graft. These spaced end-end fittings provide the operator with the flexibility of shortening the graft to any length while still incorporating end-end fittings to facilitate securing the graft to the host vessel. In addition, these end-end fittings provide radial support along the graft to maintain graft patency and facilitate puncturing the graft wall when accessing the interior of the reinforcing graft with the delivery system for inserting the branching vessel and end-side combination or an extension graft. Finally, the spaced end-end fittings provide structures that the operator may secure to the host vessel using retaining rings or sutures, as will be described below, to better secure the graft to the host vessel throughout the length of the graft.

Instead of incorporating end-end fittings at spaced intervals along the reinforcing graft, the reinforcing graft may incorporate support members that accomplish the same goals as the numerous end-end fittings. The support members may be laminated between layers of graft material. The synthetic bypass graft encompassing support members may be fabricated by extruding, spraying, injection molding, or dipping a primary layer of graft material over a removable mandrel; positioning, winding or braiding the support members on the primary layer; and extruding, spraying, injection molding, or dipping a secondary layer over the graft material/support member combination. The support members may be fabricated from a metal, alloy (e.g. stainless steel or nickel titanium), or polymer (e.g. nylon or polyester). Preferably, the support members have a shape memory. The support members may be manufactured with a wire material oriented in a serpentine pattern or a mesh defining a sufficiently large space between wires. This configuration helps support the reinforcing graft and defines a space to puncture the reinforcing graft wall and access the interior of the reinforcing graft with the delivery system of the invention. The spacing of the wires, the diameter of the wires, and the annealing of the support members may be tailored to produce a spring characteristic that matches that of a compression mechanism used to compress the host vessel wall against the end-end fittings (which in this case is the support members), also fabricated from a memory elastic material.

Figure 4:
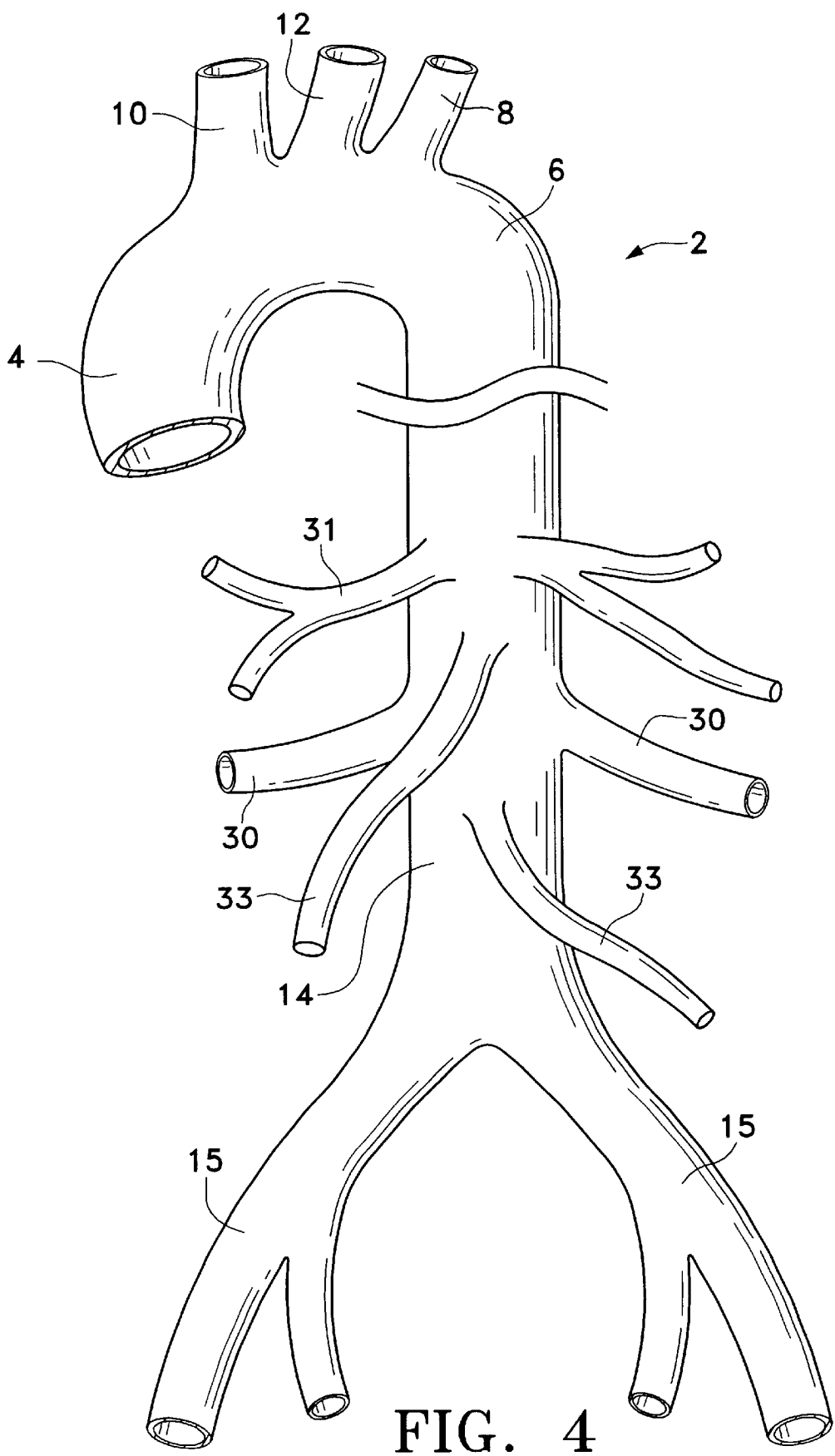
FIG. 4 shows the anatomy of the aorta and branching vessels.

FIG. 4 shows the anatomy of an aorta 2. The aortic root, not shown, runs into the thoracic aorta 4. The thoracic aorta runs around the aortic arch 6, bifurcates into the left subclavian artery 8, the brachiocephalic trunk 10, and the left common carotid artery 12, and extends into the abdominal aorta 14. The abdominal aorta bifurcates into the common iliac arteries 15. Vessel bifurcations are frequently enveloped by aortic aneurysms. As such, reinforcing or replacement grafts used to treat aortic aneurysms frequently support the affected bifurcations. For example, numerous reinforcing grafts used to treat abdominal aortic aneurysms include bifurcating legs that extend into the iliac arteries 15.

Branching vessels that extend away from the abdominal aorta include renal arteries 30, celiac arteries 31, suprarenal artery 32, mesenteric arteries 33, phrenic arteries 34, and testicular arteries 35. Abdominal aortic aneurysms are frequently classified by their location relative to the renal arteries. Infrarenal aneurysms are generally located below the renal arteries; juxtarenal aneurysms approach the renal arteries; pararenal aneurysms include the renal arteries; and suprarenal aneurysms extend above the renal arteries. Thoracoabdominal aneurysms are classified as type I, II, III or IV, depending on their location relative to descending thoracic aorta and the abdominal aorta; most thoracoabdominal aneurysms envelop the renal arteries of the abdominal aorta.

The thoracic aorta 4 extends from the abdominal aorta 14 to the aortic root and defines bifurcations to the left subclavian artery 8, the brachiocephalic trunk 10, and the left common carotid artery 12. Branching vessels that extend from the thoracic aorta include the aortic esophageal arteries, intercostal arteries, and bronchial arteries (all not shown). The left main artery and right coronary artery (not shown) branch off the aortic root.

Reinforcing Grafts

Reinforcing grafts may be fabricated from a sheet of graft material rolled into a tube with the sides bonded together, or a tube of graft material that defines a central lumen and contains at least two ends. For abdominal aortic aneurysms that require a bifurcated graft, the reinforcing graft has three ends configured to match the bifurcation from the abdominal aorta to the left and right iliac arteries. For thoracic aortic aneurysms that require a bifurcated graft, the reinforcing graft has a geometry designed to match the curvature of the thoracic aorta with bifurcations capable of extending into the subclavian artery, left common carotid artery, and brachiocephalic trunk. Other applications involving saccular or fusiform aneurysms located at vessel bifurcations also require bifurcated reinforcing grafts. Reinforcing grafts are designed to be inserted into a host vessel and extend along the interior surface of the host vessel. Once positioned and secured, the reinforcing graft isolates the host vessel wall and anything attached to the host vessel wall between the end-end fittings of the reinforcing graft from blood flow.

Figure 5:
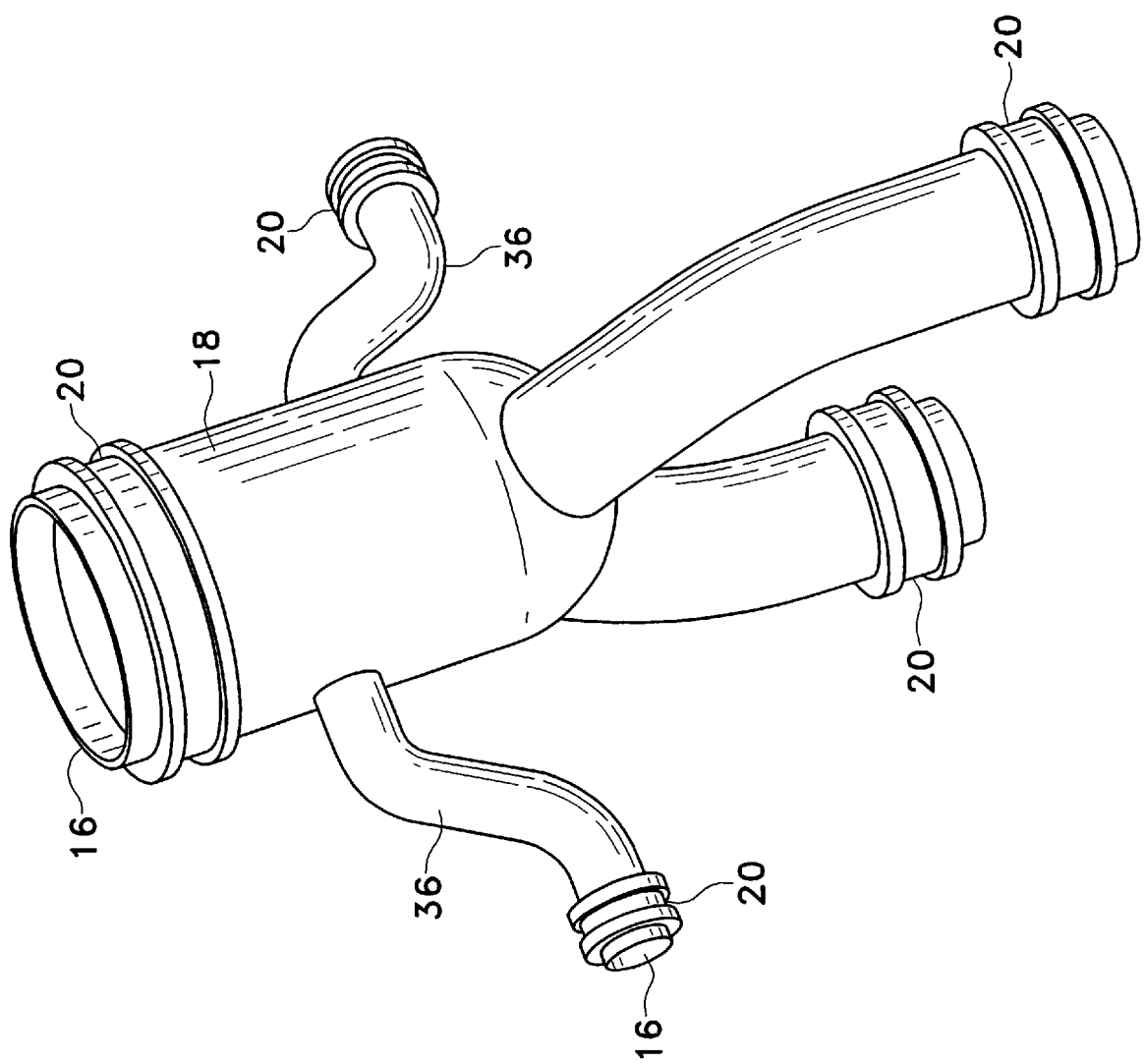
FIG. 5 shows a reinforcing graft having integrated extension grafts.

The reinforcing graft 18, as shown in FIG. 5, may additionally include branches 36. Each branch 36 incorporates an end-end fitting 20 attached at the end of the branch. The end-end fittings may be laminated between layers of graft material or may be compressed between fitting components as described above. The branches facilitate attaching branching vessels to the reinforcing graft without the need for end-side fittings or extension grafts, described herein. One method of securing branches 36 to the branching vessels is to insert the branches into the lumens of the branching vessels while positioning the reinforcing graft. Insertion devices described herein are used to position the branches. In addition, the positions of the orifices of the branches do not need to exactly match the orifices of the branching vessels. Instead, the branches may run between the reinforcing graft and the host vessel wall for a length before they extend into the lumen of the branching vessels. This accommodates the varying anatomy between patients. Once positioned, end-end fittings 20 of branches 36 are secured to the branching vessels by producing end-end anastomoses.

The reinforcing graft may be directly inserted through an incision in the host vessel wall or through a delivery system described below. Alternatively, the reinforcing graft may be inserted percutaneously using a catheter-based delivery system. The catheter-based delivery system incorporates modifications to the delivery system described below, which include longer access and guiding devices to account for remote, percutaneous vessel access, as opposed to direct vessel access.

An insertion device 38 (FIG. 6) is used to position the ends of the reinforcing graft (and branches, if present) at the desired host vessel location. The insertion device exerts force against end-end fittings 20, already attached to the ends of the reinforcing grafts 18, to advance and retract the end-end fittings of the reinforcing graft within the vasculature. Insertion device 38 has two sections 39 that rotate about a pivot 40 to accommodate various reinforcing graft geometries and enable inserting the bifurcations of the reinforcing graft into the iliacs.

Another insertion device is a plunger shown in FIGS. 7A–7C. Plunger 42 is suited for inserting grafts attached to fittings through a delivery system and positioning the end-end fittings of the reinforcing graft, extension grafts, or branches at the desired host vessel location. For bifurcated reinforcing grafts and grafts containing branches, the insertion device individually positions the legs of the reinforcing graft or branches in the appropriate host vessel. The ends of the reinforcing graft, extension graft, and branches contain end-end fittings such that, once positioned, the end-end fitting may be secured to the host vessel by producing end-end anastomoses described below.

Figure 8D:
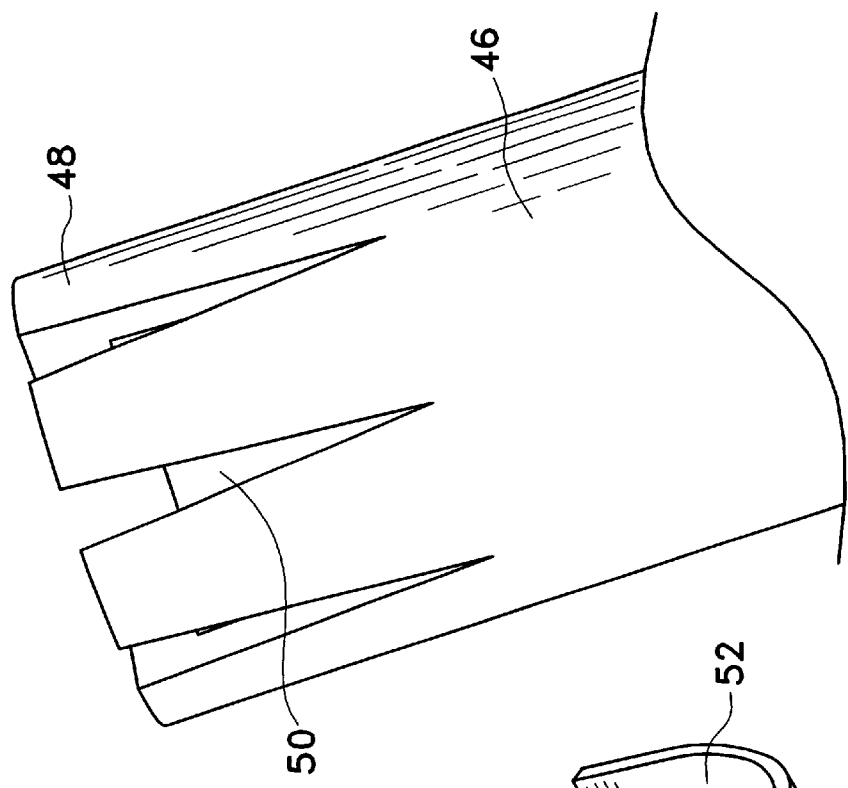
Figure 8C:
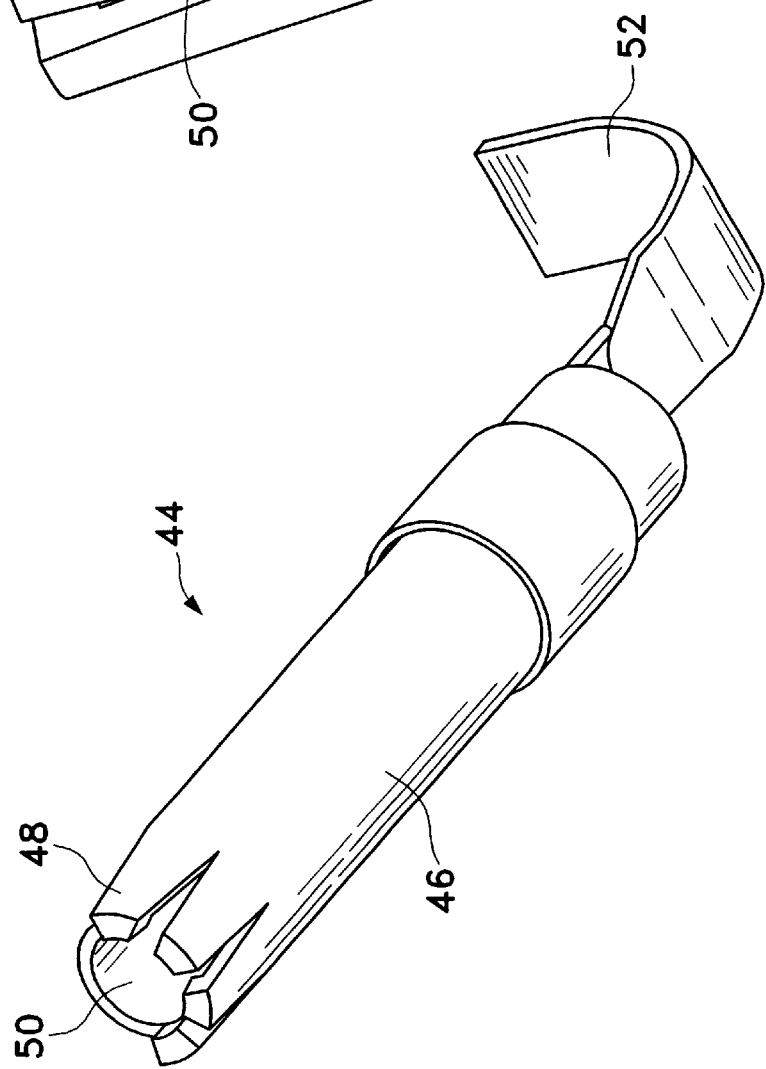

FIGS. 8A to 8F show alternative insertion devices for positioning end-end fittings within the host vessel. FIGS. 8A and 8B show an insertion device 44 with a slide 46 rotated into a closed position. The insertion device is closed after placing the reinforcing graft and the end-end fitting within a lumen defined by closed slide 46 and between grasping members 48 and pushing member 50. The pushing member 50 is attached to a handle 52 for remote handling of insertion device 44. Slide 46 is also axially movable relative to pushing member 50. FIGS. 8A and 8B show slide 46 separated from the pushing member and FIGS. 8C and 8D show the slide 46 and pushing member 50 in a closed configuration. The slide and pushing member are closed to grab the end-end fitting to provide improved manipulations. This insertion device is capable of advancing, torquing, and retracting the end-end fitting through the vasculature. Insertion device 44 is adapted to grab the entire width of the end-end fitting or just the distal end of the end-end fitting. Once the end-end fitting is positioned, slide 46 is rotated to an open configuration as shown in FIGS. 8E and 8F to permit removing from the side of the reinforcing graft, branch, or extension graft. Alternatively, the slide device is not rotatable relative to the pushing member. However, the slide still is axially manipulated to grab the end-end fitting for manipulations through the vasculature. This embodiment does not require placing the insertion device around the periphery of the reinforcing graft, branches, or extension graft and permits grabbing a small section of the end-end fitting.

Extension Grafts

Extension grafts are designed to lengthen a branching vessel that is not long enough to reach the desired anastomosis site of the host vessel (whether or not reinforced with a graft). The extension graft contains an end-end fitting at one end capable of producing an end-end anastomosis to the branching vessel. The extension graft has, at its opposite end, either an end-side fitting or an end-end fitting, depending on the application. An end-side fitting permits attaching the extension graft to an opening, created with the delivery system, in the reinforcing graft wall and/or host vessel wall to re-establish blood flow to the branching vessel. An end-end fitting enables attaching the extension graft to the end of another extension graft or a branch incorporated in the reinforcing graft.

The extension graft may be inserted into the host vessel prior to attaching the branching vessel, thereby maintaining blood flow to the branching vessel while securing the extension graft to the host vessel. Then, the branching vessel may be tied off, cut, quickly advanced over the free end of the extension graft, and secured to the end-end fitting, as will be described below. This minimizes the ischemia time associated with interrupting blood flow while reattaching the branching vessel. Alternatively, the free end of the extension graft may be inserted into the intact branching vessel using the delivery system, as described below. Once inserted into the branching vessel, the end-end fitting may be secured to the branching vessel using retaining rings or suture. The extension graft routes blood flow from the interior of the reinforcing graft or host vessel and into the branching vessel.

Delivery Systems

The delivery system embodiments of the invention for positioning the branching vessels are designed to quickly access the interior of the deployed reinforcing graft through a small puncture in a wall 54 of a host vessel 56 and the reinforcing graft wall 16. As such, the delivery systems are designed to prevent excess blood loss when accessing the interior of the reinforcing graft and deploying the branching vessel and fitting combination, thereby eliminating the need to stop or re-route blood flowing through the host vessel. This approach also improves the leak resistance around the fitting due to elastic compression of the vessel wall and the reinforcing graft wall around the fitting. Additionally, the delivery system enables deploying an extension graft through host vessel wall 54 and reinforcing graft wall 16.

Figure 9C:
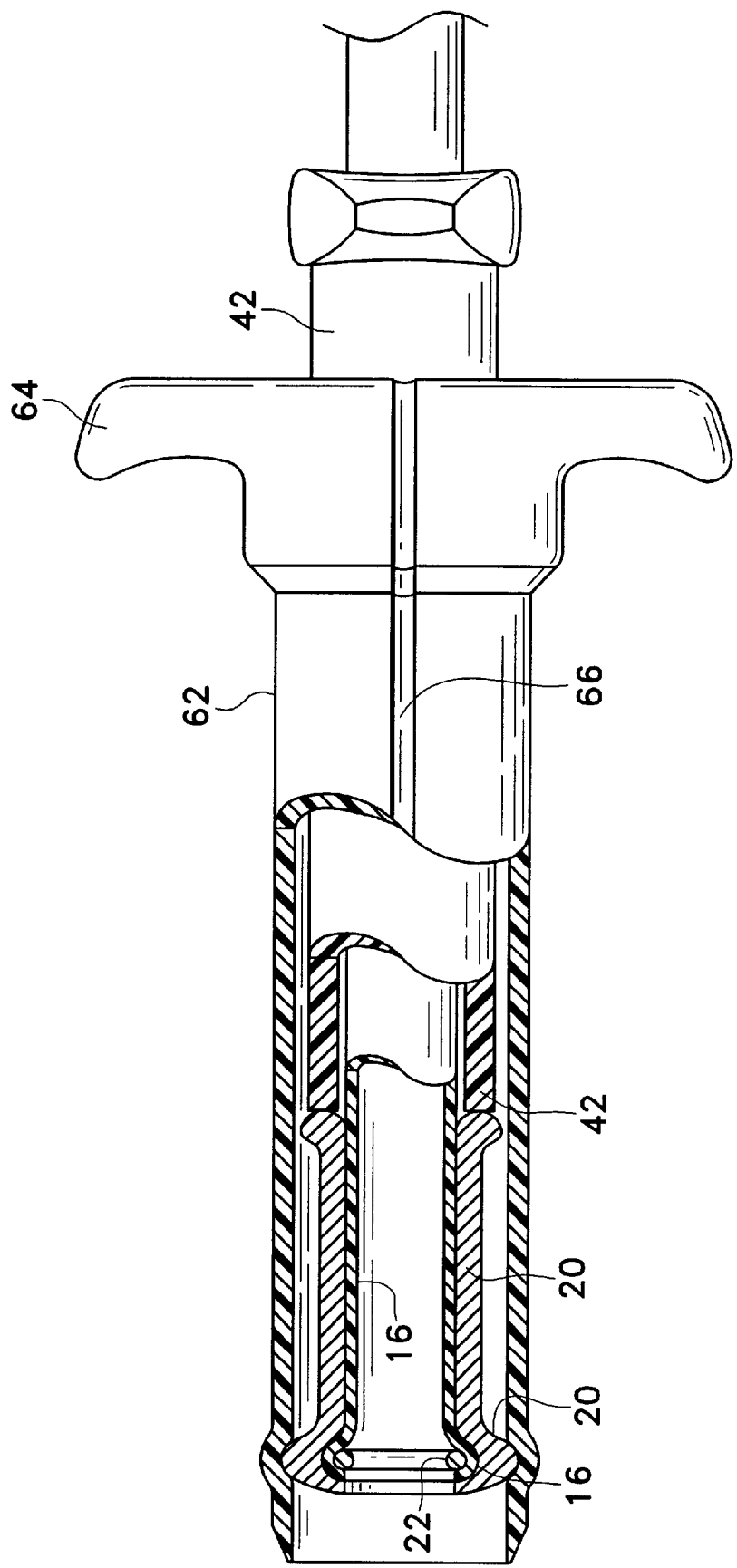

The delivery system must permit removal from around the branching vessel or the extension graft after securing the transected end of the branching vessel or the extension graft to the host vessel. FIGS. 9A to 9C show representative steps to position a branching vessel and fitting combination through a host vessel wall and a reinforcing graft wall. These steps also demonstrate the process for deploying an extension graft through the host vessel wall and the reinforcing graft wall.

A puncture device 58 (e.g. needle) is preloaded through a dilator 60 that has been preloaded through a sheath 62. The needle, dilator, and sheath combination is then positioned at the target anastomosis site. As shown in FIG. 9A, the needle is used to puncture host vessel wall 54 and the reinforcing graft wall 16, and is advanced into the interior of the reinforcing graft. The needle may be designed with a tapered or stepped distal end 86 to restrict movement of the needle 58 beyond the end of the dilator and prevent perforating the opposite side of the host vessel or unwanted anatomy. A guidewire (not shown) may be advanced through the needle to provide a path over which the dilator and sheath may be advanced. When using a guidewire, the needle may be retracted to prevent unwanted perforations or abrasions to the host vessel or adjacent anatomy. The needle does not necessarily need to be preloaded through the dilator, permitting the use of a larger diameter guidewire that better matches the inner diameter of the dilator. The dilator is then advanced over the needle or guidewire, past the host vessel wall, past the reinforcing graft wall, and into the interior of the reinforcing graft. Subsequently, the needle (if not already retracted to insert the guidewire) may be removed or retracted inside the dilator. The dilator is tapered to provide a smooth transition when advancing the dilator through the host vessel wall and reinforcing graft wall. The host vessel wall and reinforcing graft wall inherently form seals around the dilator preventing excess blood leakage from the host vessel.

Sheath 62 has a radius or tapered distal end forming a smooth transition from the dilator to the body of the sheath around the dilator. Once the dilator is positioned within the interior of the reinforcing graft, the sheath is advanced over the dilator and into the interior of the reinforcing graft. At this point, the dilator may be removed. This technique of inserting a sheath into a vessel over a dilator and needle is commonly used by physicians when performing the Seldinger technique during catheterization procedures or inserting intravenous catheters into veins for withdrawal of blood or introduction of medicines. The sheath and dilator may be constructed from polyethylene or other polymer that may be extruded or molded into a tube. The sheath and dilator may incorporate a braided layer laminated between two polymer layers to resist kinking and improve the column strength and torque response. A taper and radius may be formed in the distal end of the dilator and sheath by thermally forming the raw tubing into the desired shape. In addition, the sheath may incorporate a softer distal tip fabricated by thermally bonding a short section of lower durometer tubing to the sheath or tapering the thickness of the sheath tubing.

The hubs on the sheath and dilator may be fabricated from polycarbonate, polyethylene, thermoplastic (such as PEEK, manufactured by Victrex PLC, United Kingdom), urethane or other material that may be injection molded, adhesively bonded, ultrasonically welded, or thermally bonded to the tube. A hub 64 of the sheath contains at least one and preferably two grooves, slits, or series of perforations 66 along the hub to enable the operator to split the hub when removing the sheath from around the branching vessel. The hub of the sheath houses a hemostatic valve 68 constructed of silicone, urethane, or other material having a low durometer and a large percent elongation characteristic. The valve may be coated with a lubricant such as silicone to facilitate insertion of the fitting and branching vessel combination or extension graft through the sheath. The hemostatic valve prevents excess blood loss through the sheath when positioned inside the vessel. The valve also incorporates at least one groove, slit, or series of perforations to permit separation when tearing the sheath from around the bypass graft. A side port (not shown) may be included to aspirate and flush the sheath. The hub may alternatively be a separate piece from the tear-away sheath such that it may be independently removed from around the branching vessel. This hub would include a luer fitting to enable securing onto a mating piece of the tear-away sheath, or other mechanism to permit removably attaching the hub to the tear-away sheath. This hub may incorporate at least one groove, slit, or series of perforations to enable splitting the hub to form an opening to remove the hub from around the bypass graft. Alternatively, the hub may include a slot, which during use is closed to prevent fluid from leaking, but can be aligned to form an opening for removal from around the bypass graft.

The ability to split is essential to removing the sheath from around a branching vessel when the sheath is unable to slide past the opposite end of the branching vessel. As shown in FIG. 9C, the sheath 62 may also be fabricated with at least one groove 66, slit, or series of perforations formed along the tube and hub to provide a guide to tear-away the sheath along at least one side, after securing the branching vessel to the host vessel wall and reinforcing graft wall. Alternatively, the sheath may include a section of tubing material already split into at least two sections such that the sheath tubing tends to continue to split into two pieces as the two sections are pulled apart. When incorporating supporting material into a tear-away sheath to improve column strength, this material should ensure the sheath may be split along the grooves, slits, or perforations formed in the sheath. This supporting material may be fabricated into two braided sections, or other support member sections oriented on opposite sides of the sheath such that the grooves reside along the spaces between the braided sections. Alternatively, the supporting material may be strands of wire (stainless steel, nylon, etc.) laminated between layers of sheath material and oriented axially along the longitudinal axis of the sheath.

The length of the sheath should be limited to that required to access the interior of the reinforcing graft while ensuring short sections of exposed branching vessels or extension grafts may be inserted past the distal end of the sheath, especially when the branching vessel has been secured at the opposite end. To make the sheath suitable for less invasive access, a long side arm extension to the sheath may be incorporated to support the sheath during manipulations. The side arm should define two separable sections that permit splitting and remotely tear the sheath into two sections to remove from around the branching vessel.

Figure 10:
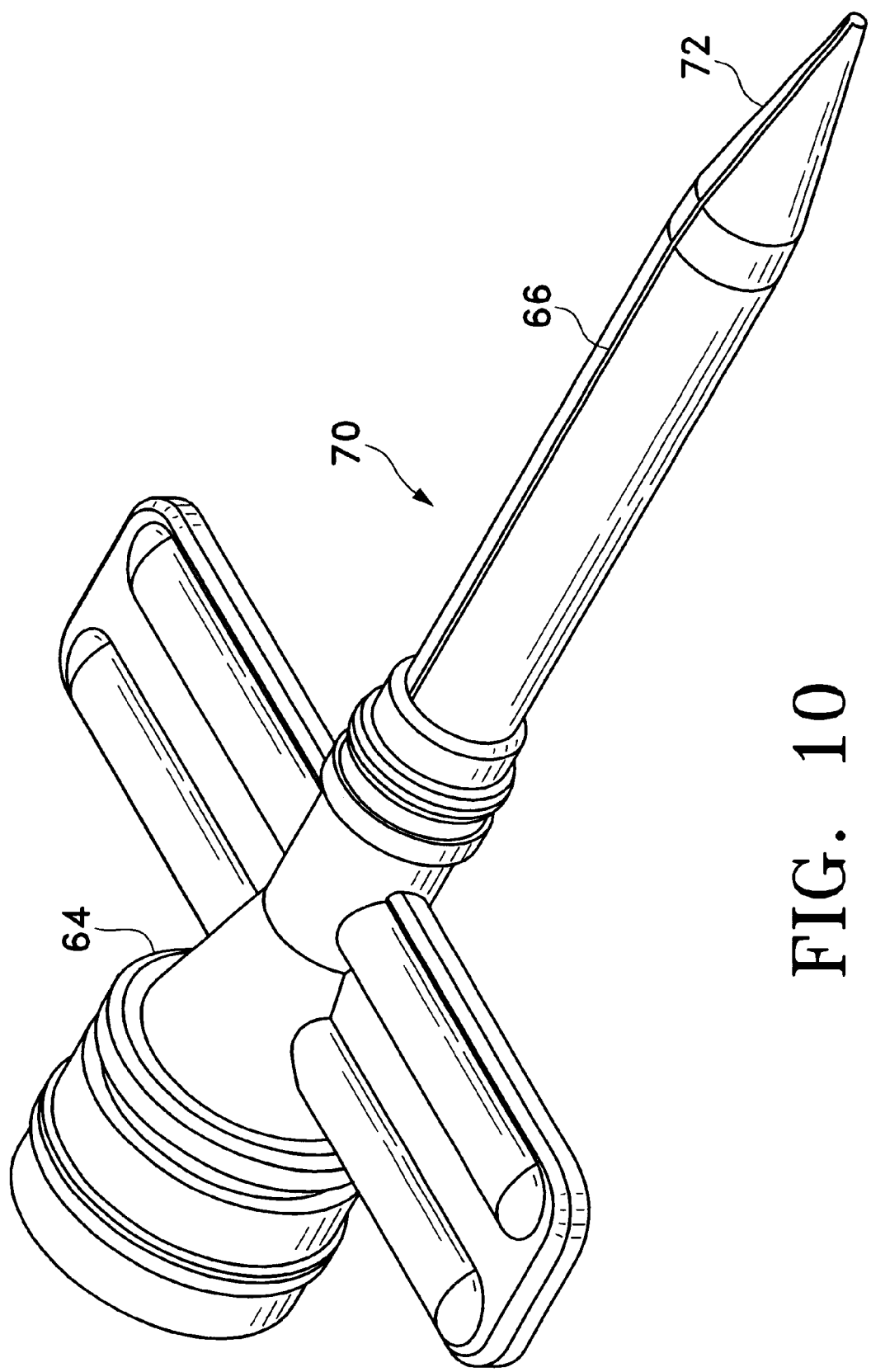
FIG. 10 shows a dilating sheath.

FIG. 10 shows an adaptation of a delivery system that combines the tear-away sheath and the dilating member into one component. The dilating sheath 70 contains at least one groove, slit, or series of perforations 66 that enables splitting the dilating sheath for removal from around the branching vessel or extension graft. The dilating sheath also contains a tapered distal end 72 that is designed to follow a needle or guidewire through a puncture in vessel wall and/or the reinforcing graft wall, and expand the puncture to facilitate inserting the main section of the dilating sheath. The dilating sheath has a central lumen (not shown) adapted to pass the bypass graft and fitting combination. A plunger is used to advance the branching vessel and fitting combination past the tapered end 72 of the dilating sheath and into the interior of the reinforcing graft. As discussed for the tear-away sheath, the dilating sheath contains a hub 64 and hemostatic valve that permit splitting along groove, slit, or series of perforations 66.

Tapered end 72 must prevent collapsing while inserting through and opening the puncture site, and enable expanding so the bypass graft and fitting combination may be advanced into the host vessel lumen. The tapered end may be fabricated by cutting the end of the sheath tubing into three or more sections such that each section tapers distally, forming the sections such that they create a single tapered distal end (the sections may overlap partially), and covering the tapered distal end with a material having a low durometer and a large percent elongation (e.g. silicone and urethane). The sections are formed such that they exert radial force to prevent collapsing while the dilating sheath is advanced through the puncture site. The covering provides a fluid tight coating around the tapered end that elongates as the sections are spread apart; this enables expanding the diameter of the tapered end while the bypass graft and fitting combination are inserted through the tapered end. An alternative fabrication process eliminates the need for the covering by bonding the overlapping sections with a temporary low strength adhesive. The low strength adhesive holds the position of the tapered end sections and produces a fluid tight interface between the sections but permits the sections to separate as the plunger advances the bypass graft and fitting combination through the positioned dilating sheath.

An adaptation to the delivery system addresses conditions where the reinforcing graft or extension graft is inserted through a large incision through the host vessel wall or through the end of a transected host vessel. A modified "hockey stick" sheath 74, (FIGS. 11A to 11F), has a tapered distal end 76 and a partially enclosed body. This hockey stick sheath is advanced through the incision or the open host vessel end, and expands the vessel wall. This way the reinforcing graft, extension graft, or branching vessel and fitting combination may be advanced through the hockey stick sheath lumen and into the host vessel without catching on the vessel wall. This is especially important when the fitting has an outer diameter larger than the inner diameter of the host vessel such that the host vessel must be expanded to insert the fitting. The hockey stick sheath may incorporate an extension perpendicular to the longitudinal axis that provides a handle to manipulate the hockey stick sheath. In addition, the hockey stick sheath may incorporate at least one spring-loaded jaw to grab the host vessel wall after access has been obtained and permit manipulating the expanded host vessel by using the hockey stick sheath. This is especially useful when accessing the end of a transected vessel, which requires significant manipulations while positioning the extension graft into the lumen of the host vessel.

Plunger 42 is designed to insert the branching vessel and fitting as an attached unit, therefore it includes a lumen to protect the branching vessel while inserting the fitting into the interior of the reinforcing graft. The plunger is also used to advance the extension graft through the sheath and into the interior of the reinforcing graft or the host vessel lumen. A plunger is essential when inserting branching vessels or extension grafts that do not have adequate column strength to be pushed through the hemostatic valve of the sheath. After using the plunger to advance the branching vessel and fitting combination into the interior of the reinforcing graft, the plunger is contained between ends of the attached branching vessel and must be removed. The plunger 42 shown in FIGS. 7A to 7C includes an axial slot 74 through the entire length of the plunger. The slot enables pulling the plunger from the side of the branching vessel when removing the plunger and permits pressing the plunger over the side of the branching vessel when placing the plunger over the branching vessel. One end 76 of this plunger has a short length stepped down to form a smaller outer diameter that fits inside the inner diameter of the fitting and provides a stable anchor to insert and manipulate the fitting during delivery of the bypass graft and fitting combination into the vessel. The other end 78 of plunger 42 has the inner diameter reamed out and notched for a short length to fit over the outer diameter of the branching vessel and fitting combination during manipulations. The notched region may alternatively extend a sufficient length such that the plunger covers the exterior of the fitting to protect the fitting during insertion through the sheath. This feature is especially important when inserting end-side fittings that require constraining the petals (discussed below) in a reduced diameter profile for advancing through the sheath. This feature also helps constrain foldable or compressible fittings into a reduced diameter for insertion through a sheath having a smaller inner diameter than the expanded outer diameter of the fittings. Since this plunger maintains its integrity upon removal from the branching vessel, it may be used to deploy multiple branching vessel and fitting combinations.

End-End Anastomoses

End-end fittings 20 may be incorporated in the reinforcing graft and the extension graft to facilitate securing the graft to a host vessel. The end-end fittings are configured to be inserted into the lumen of the host vessel and to contact the host vessel interior surface throughout its cross-section. A groove may be fabricated on the fitting outer surface to prevent axial movement of the retaining ring after positioning the retaining ring over the host vessel to fitting interface. The retaining rings are designed to produce an interference fit between the reinforcing graft or the extension graft and the host vessel to hold the graft in place and prevent leaking at the attachment point.

Figure 12B:
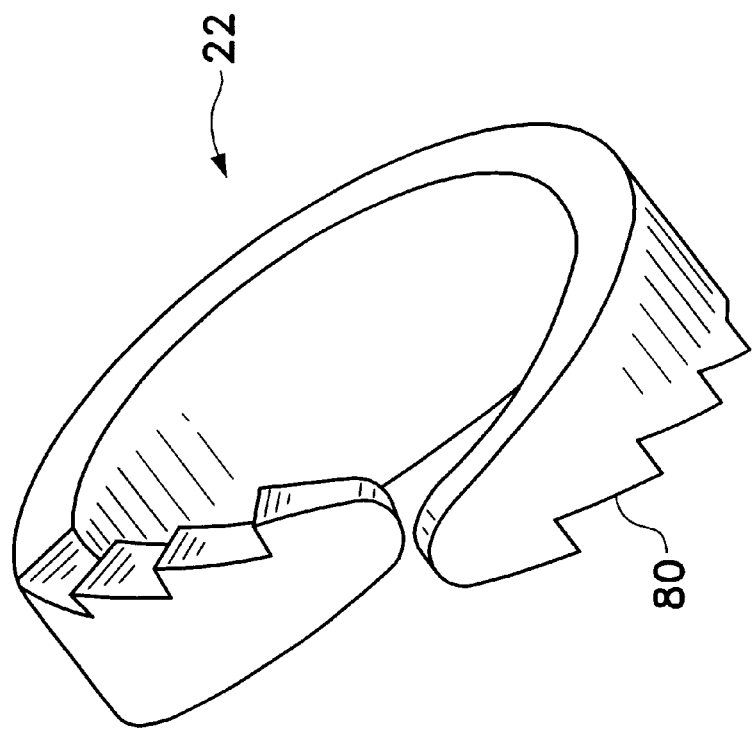
FIGS. 12A and 12B show retaining rings used to bond tubular structures to fittings and host vessels in accordance with the invention.
Figure 12A:
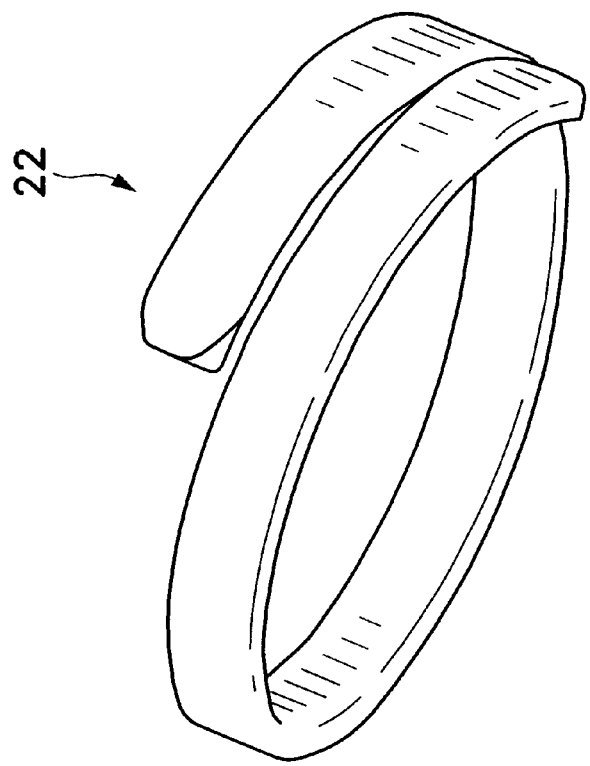

FIGS. 12A and 12B show embodiments for retaining ring 22 used to secure the end-end fitting 20 of the reinforcing graft or the extension graft to the host vessel. The retaining ring may have a rectangular, circular, semicircular, or elliptical cross-section. The retaining ring may include eyelets to facilitate its positioning around the host vessel to fitting interface. These eyelets may also be used to suture the retaining ring closed for additional support. Retaining ring 22 may be fabricated from a metal, alloy, thermoplastic material, thermoset, or composite. However, the retaining ring must permit approximately 30% enlargement in diameter without becoming permanently deformed. Thus, after placement, the retaining ring will compress the host vessel against the fitting and form a secure seal. As a result, the preferred material for the retaining ring is a memory elastic alloy such as nickel titanium exhibiting a stress-induced martensite characteristic or a semiaustenitic spring stainless steel such as 17-7PH (sold by Armco, Inc., Pittsburgh, Pa.).

The retaining ring 22 in FIG. 12A is a preshaped member wound beyond a single turn. One representative fabrication process for the preshaped retaining ring involves forming the raw material into a desired geometry and exposing the material to sufficient heat to anneal the material into this predetermined shape. This process applies to metals, alloys (e.g. nickel titanium), polymers, or composites of the aforementioned materials. The preshaped retaining ring configuration is expanded by inserting the expansion tool into the middle of the retaining ring and opening the expansion tool to enlarge the retaining ring diameter. Once the retaining ring is positioned, the force causing the retaining ring to enlarge is removed, causing the retaining ring to return towards its preformed shape. This compresses the host vessel against the fitting.

The retaining rings do not necessarily need to incorporate elastic memory characteristics. For example, retaining ring 22 in FIG. 12A may be manufactured from a deformable material and crimped over the tubular structure to fitting interface or the host vessel wall to fitting interface for securing purposes. FIG. 12B shows another retaining ring 22 that does not incorporate elastic memory characteristics. This retaining ring is opened for positioning around the bypass graft to fitting interface or the host vessel to fitting interface. When closed, teeth 80 engage and lock the retaining ring in the closed position. Closing the retaining ring further causes the diameter to decrease and exerts additional compressive force.

Figure 13:
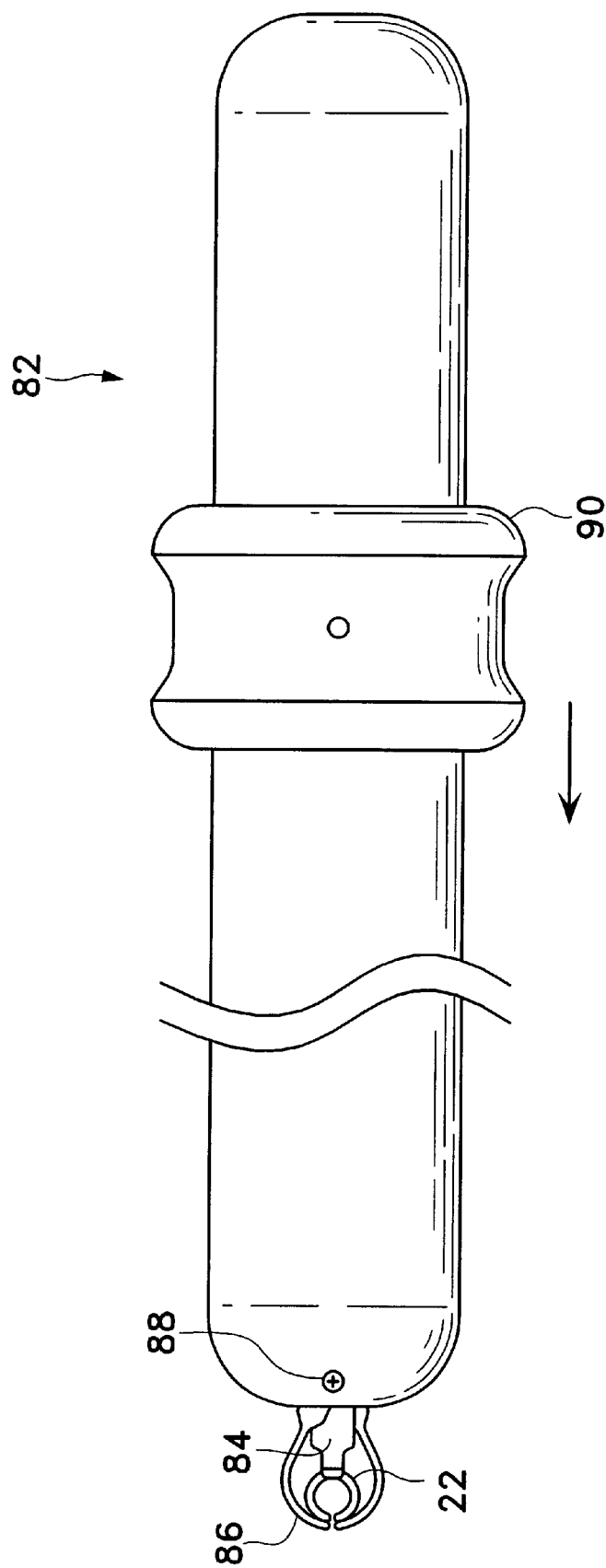
FIG. 13 shows an expanding tool used to expand and position a retaining ring.

A representative expansion tool 82 is shown in FIG. 13. This tool is designed to expand the retaining ring by pulling its ends relative to an anchor point. A stylet 84 holds the retaining ring in place and produces the anchor point. Legs 86 of the expansion tool have notches positioned at the edges of the retaining ring. The legs rotate about a pivot pin 88 fixed to the handle. When the knob 90 is advanced relative to the handle, the legs are configured to move radially outward thereby opening the diameter of the retaining ring. Once positioned around the host vessel to fitting interface, tension on the knob is released, allowing the retaining ring to compress the host vessel against the fitting.

Figure 14A:
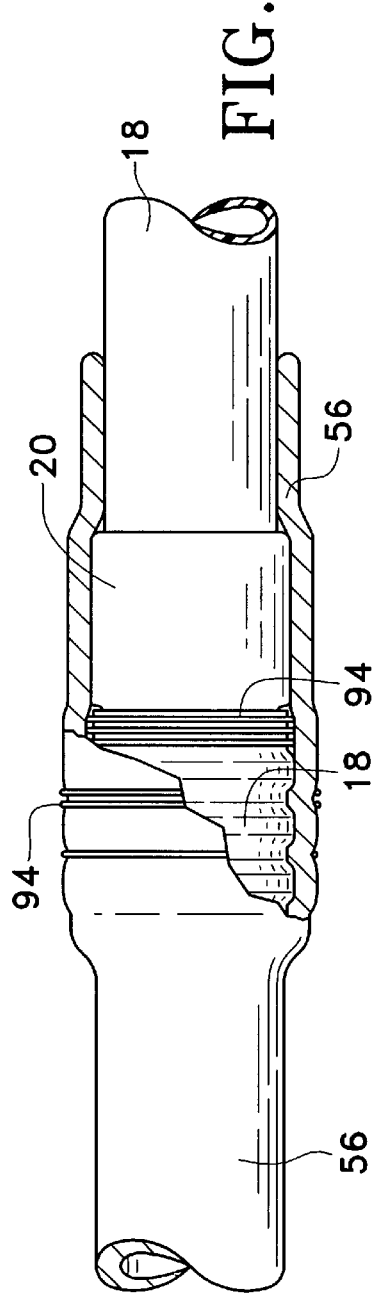
FIGS. 14A to 14C show an end-end fitting for securing tubular structures such as vessels and grafts to fittings using sutures.
Figure 14B:
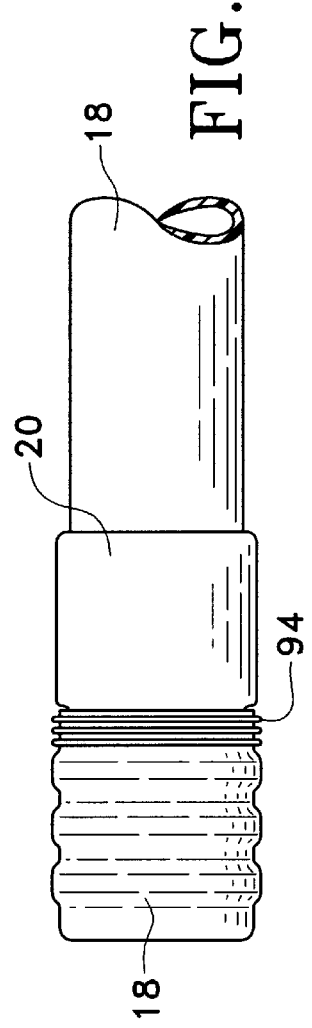
Figure 14C:
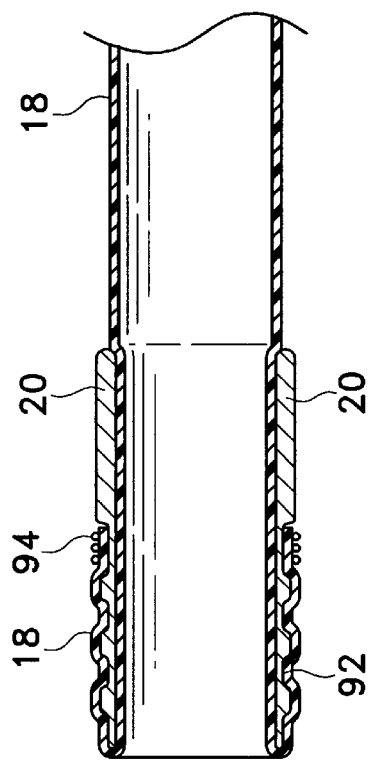

FIGS. 14A to 14C show methods of suturing a host vessel to an end-end fitting. The end-end fitting 20 has notches 92 designed to provide an indentation to secure a host vessel using the retaining ring as described above, or suture 94 as described below.

Once the reinforcing graft is advanced into the lumen of the host vessel 56, one or more strands of suture 94 are tied around the host vessel and located in the notches of the end-end fitting 20 thereby producing a fluid tight seal. Alternatively, stitches may be created at fixed intervals around the host vessel wall to end-end fitting interface. The suture is fed through the host vessel wall from the external surface of the host vessel 56, pushed around the end-end fitting 20 or through the end-end fitting when the fitting is fabricated from a compliant material, pulled back through the host vessel wall on the opposite end of the fitting, and tied into a knot. Needles attached to the strands of suture 94 permit puncturing the vessel wall (and fitting for compliant fitting materials) and advancing the suture for forming the stitches. These methods permit suturing the reinforcing or extension graft 18 to a host vessel 56 while blood is flowing through the host vessel.

End-Side Anastomoses

Figure 15:
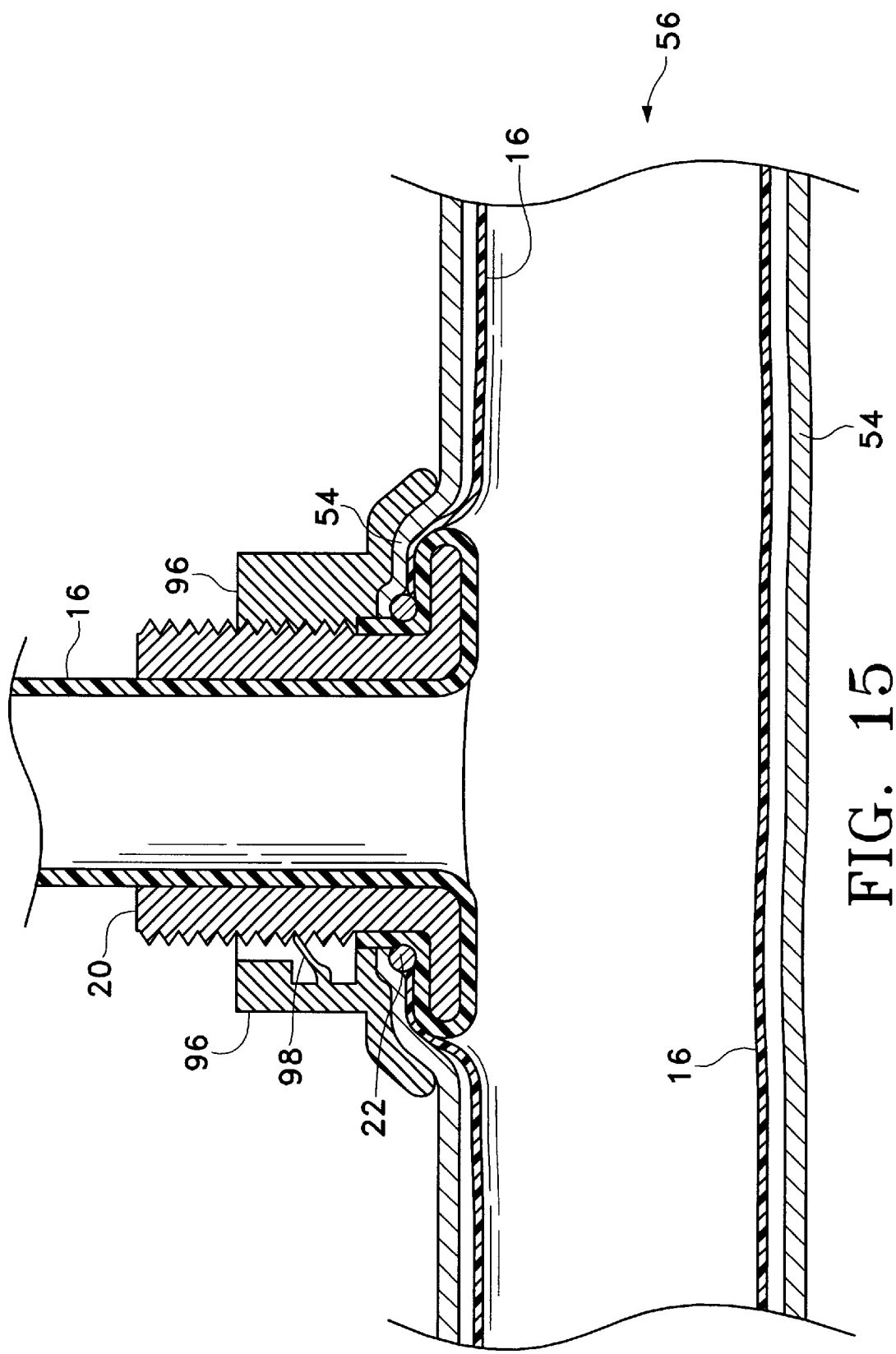
FIG. 15 shows an end-side fitting using a latching mechanism to secure a tubular structure to a host vessel wall.

An embodiment for producing an end-side anastomosis between a branching vessel or extension graft and a reinforcing graft is shown in FIG. 15. After the branching vessel and fitting combination or extension graft is inserted partially through the host vessel wall 54 and the reinforcing graft wall 16, a self-locking compression ring 96 is advanced over teeth incorporated in fitting 20. A ratcheting mechanism 98 prevents the self-locking component from dislodging from the fitting. The distal end of compression ring 96 is designed to match the flared end of fitting 20. Therefore, as compression ring 96 is further advanced relative to fitting 20, host vessel wall 54 and reinforcing graft wall 16 become compressed between the compression ring 96 and the flared end of the fitting producing a fluid tight, secure bond. This embodiment is capable of bonding the host vessel wall and the reinforcing graft wall to the branching vessel and fitting combination or the extension graft.

For applications where the operator wants to evert the end of a tubular structure (e.g. branching vessel) over the fitting prior to deploying and securing the fitting to the host vessel wall, an everting tool 100 is used to wrap the tubular structure around the end of the fitting. One everting tool embodiment shown in FIGS. 16A to 16C may be inserted into the distal end of the tubular structure 104. The distal end 102 of the everting tool is designed to fit through the lumen of the tubular structure 104 and the inner diameter of the fitting 20. Proximal to the everting tool distal end is a tapered or curved region 106 which causes the tubular structure 104 to wrap around the distal end of the fitting as the tubular structure and fitting are advanced over the everting tool. A retaining ring 22 is housed around the everting tool and is advanced over the tubular structure and fitting to secure the tubular structure to the fitting.

Figures 17A, 17B:
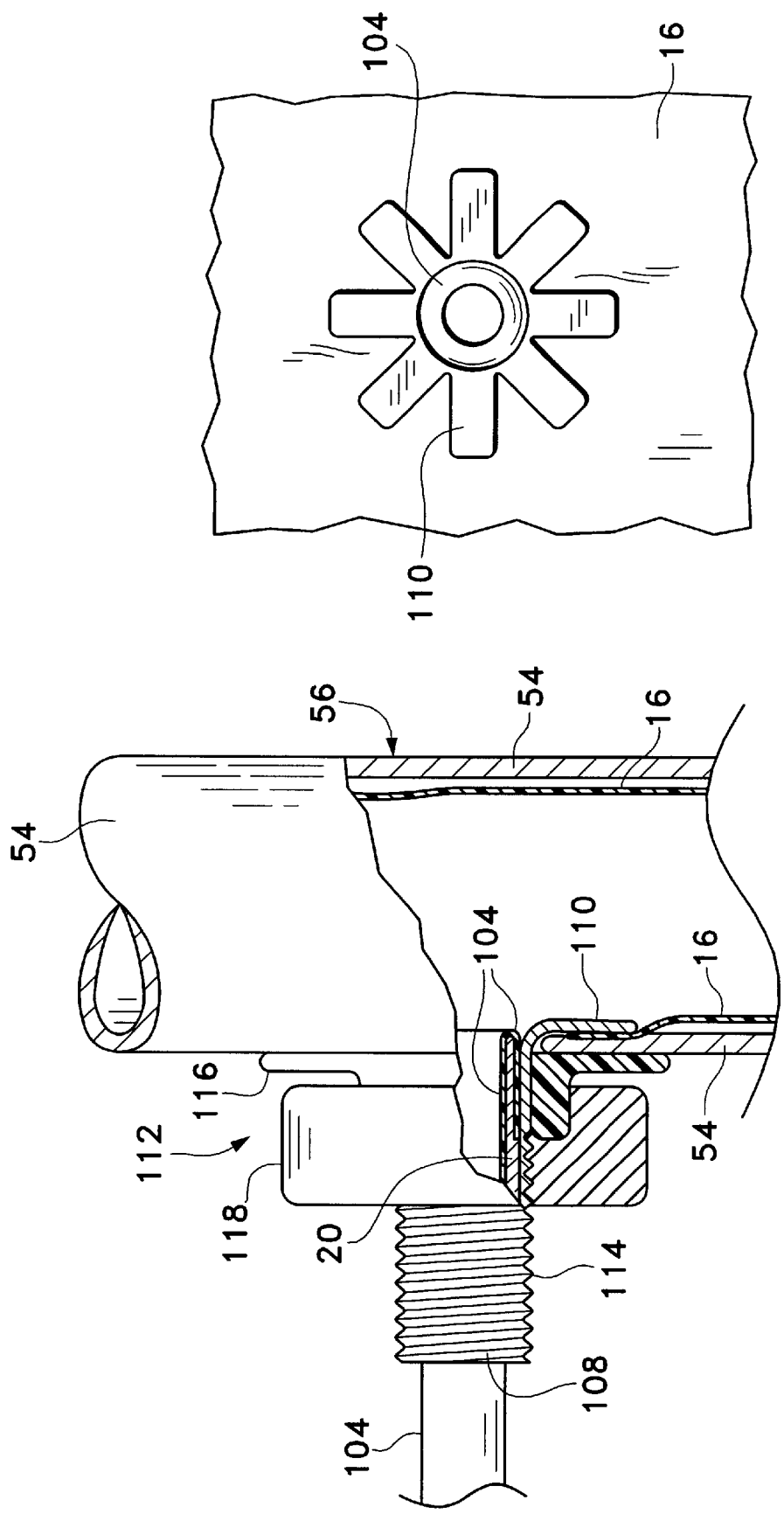
FIGS. 17A and 17B show an end-side fitting designed to compress the host vessel wall between two fitting components.

An alternative embodiment for performing an end-side anastomosis is shown in FIGS. 17A and 17B. This embodiment includes a fitting 20 with a tubular structure (e.g. branching vessel) 104 everted over the distal end of the fitting. A retaining housing 108 may be used as a compression mechanism to secure the branching vessel or extension graft to the fitting 20 for configurations when the retaining housing is expanded or advanced over the fitting to compress the branching vessel or extension graft against the fitting in an everted orientation. One retaining housing permits radial expansion during placement over the branching vessel and fitting, yet has a preshaped memory to compress around the branching vessel and fitting thereby securing the branching vessel to the fitting. This retaining housing 108 has petals 10 at its distal end that compress into a low profile during delivery through a sheath and expand radially once deployed inside the host vessel wall and reinforcing graft wall.

The number of petals incorporated in the retaining housing design depends on the size of the branching vessel. In this illustrated embodiment, eight petals are used. The petals 110 may be oriented at fixed intervals or at varying angles; the petals may also have a fixed length or varying lengths depending on the requirements for insertion and engagement against the host vessel wall.

After advancing the tubular structure (e.g. branching vessel or extension graft) and fitting through a sheath and past the host vessel wall and the reinforcing graft wall, the fitting is advanced beyond the end of the sheath by which it is no longer constrained. The fitting then expands towards its resting configuration.

Next, the tubular structure and fitting combination is gently retracted to engage the reinforcing graft wall with the petals. For mechanical securing, a compression ring 112 is advanced over the fitting, thereby compressing the host vessel wall and the reinforcing graft wall against the petals of the retaining housing. To optimize the contact from the petals to the host vessel wall and the reinforcing graft wall, the angle between the petals and the proximal portion of the fitting of may be less than ninety degrees. Alternatively, the petals may be curved towards the proximal portion of the fitting. In addition, a stop may be incorporated in the fitting to prevent over-compressing the reinforcing graft wall and the host vessel wall against the petals using the compression ring. Such features better ensure that the distal ends of the petals maintain intimate contact to the host vessel wall and the reinforcing graft wall when the compression ring is secured to the fitting.

As shown in FIG. 17A, the retaining housing 108 may incorporate a locking mechanism 114 with which to secure the compression ring 112. For example, compression ring 112 can incorporate a screw mechanism that matches threads in the retaining housing. To reliably screw a compression ring onto a retaining housing, this threaded retaining housing 108 has a fixed diameter and is not expandable. The threads are oriented only along the sections of the retaining housing configured to engage the compression ring. The compression ring is alternatively locked in place using a ratchet mechanism, adhesives, sutures, or other attachment means to secure the compression ring in place. The compression ring 112 for this embodiment incorporates two components: (1) a distal, flexible o-ring or disk 116 designed to produce a fluid tight seal and prevent damaging the vessel wall by excess compression, and (2) a proximal, more rigid locking ring 118 used to maintain the position of the o-ring or disk relative to the host vessel wall 54 and the reinforcing graft wall 16. The locking ring 118 is designed to match the threads incorporated in the retaining housing 108.

Figure 18B:
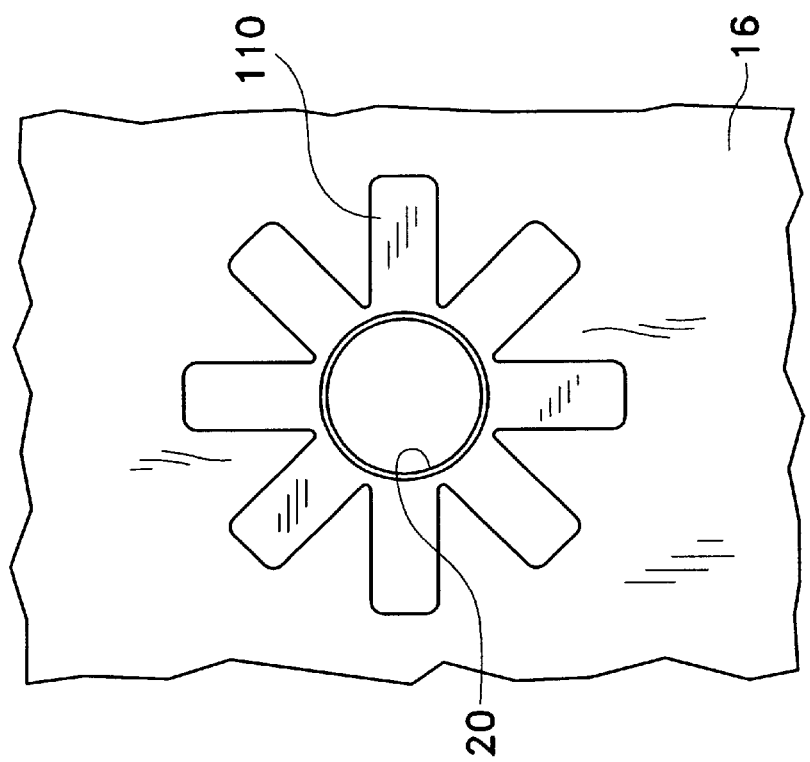
FIGS. 18A and 18B show an alternative end-side fitting secured to a host vessel wall.
Figure 18A:
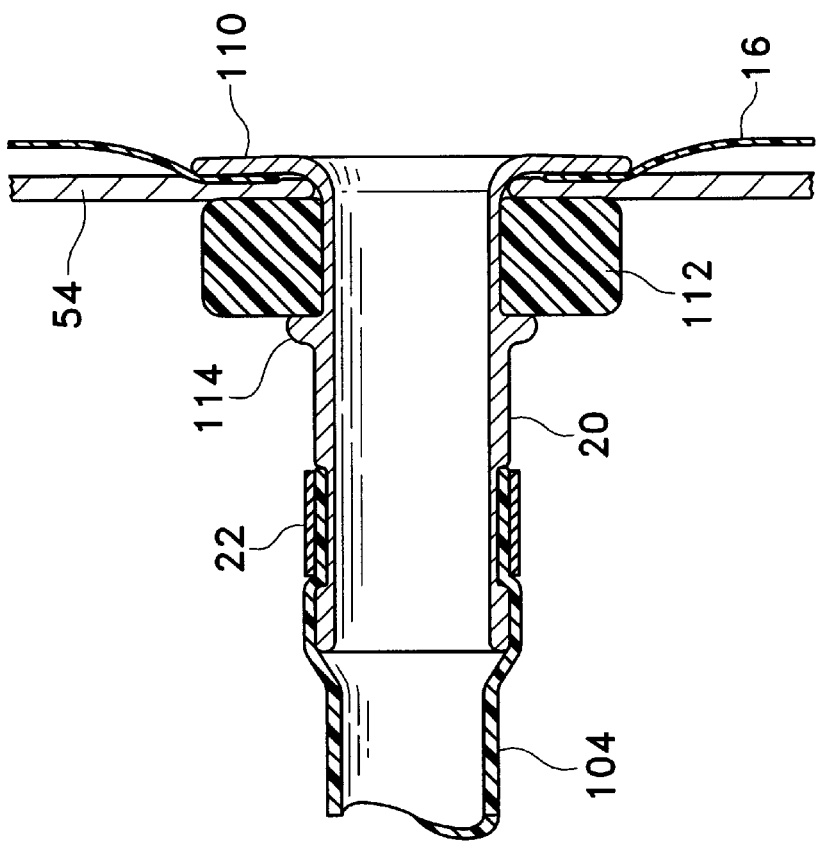

FIGS. 18A and 18B show another fitting 20 used to produce an end-side anastomosis. In this embodiment, the fitting incorporates petals 110 that collapse into a low profile during delivery through a sheath and extend radially outward once deployed into the interior of the reinforcing graft. In this embodiment, the branching vessel or the extension graft 104 is advanced over the outside of the fitting and is compressed against the fitting using a retaining ring 22.

For extension grafts, the fitting may alternatively be laminated between layers of graft material. A compression ring 112 is still advanced over the fitting after deploying the fitting into the interior of the reinforcing graft, and is used to compress the host vessel wall and the reinforcing graft wall against the deployed petals of the fitting. This secures the fitting to the host vessel wall and the reinforcing graft wall. As previously discussed, the fitting incorporates a locking mechanism 114 to prevent axial motion of compression ring 112.

All fittings that incorporate petals and compression rings used to produce end-side anastomoses may be configured to produce a selected angle between the fitting axis and the interior of the reinforcing graft. In addition, the proximal end of the fitting may incorporate slots extending radially around a portion of the fitting and at specified intervals along the fitting. The slots institute flexibility in the fitting to permit slight movement of the fitting while maintaining radial stiffness so to prevent kinking of the extension graft or the branching vessel.

Figure 19D:
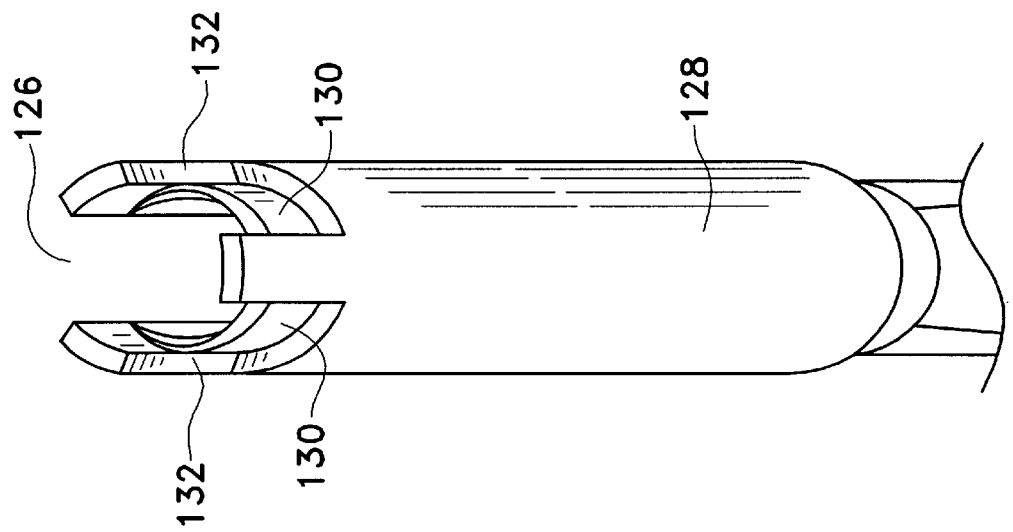
FIGS. 19C and 19D show the compression tool in the activated position.
Figure 19C:
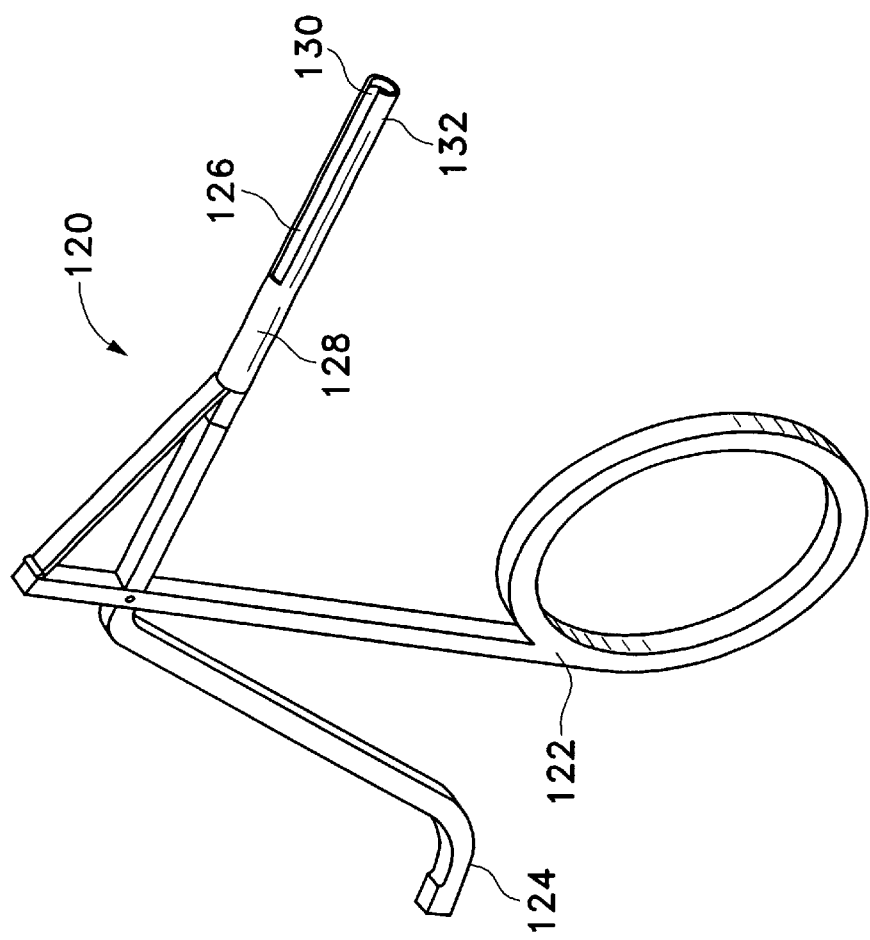

FIGS. 19A to 19D show a compression tool 120 designed to advance a compression ring (not shown) over an end-side fitting (not shown) without dislodging the fitting and without damaging the fitting, the tubular structure, the reinforcing graft wall, or the host vessel during the securing process. FIGS. 19A and 19B show the compression tool in the relaxed position. The compression tool has a front handle piece 122 and a rear handle piece 124 spread apart in the relaxed position. The handle pieces are squeezed together (activated) to advance the compression ring over the end-side fitting as shown in FIGS. 19C and 19D. The compression tool may be spring loaded to return to the relaxed position when the force causing the handle pieces to squeeze together is removed. The compression tool has a slot 126 through the distal section adapted to fit over the side of the tubular structure and fitting. This eliminates the need to preload the tubular structure through the compression tool prior to the procedure, and facilitates removing the compression tool after securing the tubular structure.

As shown in FIG. 19B, the compression tool incorporates a slide 128 adapted to move along grasping legs 130. The grasping legs are anchored to the rear handle piece 124, and the slide is advanced by squeezing the front handle piece towards the rear handle piece. The slide and the grasping legs are configured to define slot 126 through the distal section of the compression tool. The grasping legs are flared outwardly as they extend distally to fit around the proximal end of the fitting in the relaxed state. The legs 130 close around the fitting (shown in FIG. 19D) as the slide 128 is advanced thereover. Slide extensions 132 are either incorporated in the distal end of the slide design or are bonded to the slide, depending on the manufacturing process and whether the slide extensions are fabricated from the same material as the slide. The slide extensions 132 exert a radial spring force to close the grasping legs 130 around the fitting and push the compression ring over the end-side fitting.

The compression ring is first placed over the grasping legs 130 and against the slide extensions 132 prior to advancing the compression ring over the fitting. Then, the compression tool 120 is positioned so the grasping legs 130 extend over the proximal end of the end-side fitting. The front handle piece 122 is squeezed toward the rear handle piece 124 causing the slide 128 to advance over the grasping legs 130. Simultaneously, the grasping legs close around the fitting, temporarily securing the compression tool to the fitting. The compression ring is then advanced over the fitting.

This compression tool 120 also provides an anchor (not shown) for grabbing the proximal end of the fitting and advancing the compression ring. This facilitates compressing the host vessel wall and the reinforcing graft wall against the petals of the fitting.

FIGS. 20A to 20E show a fitting 134 for producing an end-side anastomosis that compresses the vessel wall between two fitting components. In this embodiment, the fitting 134 incorporates a flared distal region 136 having a slot 138 that defines two edges. The slotted distal end of the fitting is inserted through a puncture of the vessel wall 54 and the reinforcing graft wall 16 by positioning the edge of the slotted fit ting at the puncture site, angling the distal flared region 136 so the edge may be further advanced through the host vessel wall and the reinforcing graft wall, and rotating the fitting 134. Upon further rotation of the fitting, the entire flared region 136 is advanced into the interior of the reinforcing graft as shown in FIG. 20D. Next, a compression ring 112 is positioned over the fitting and past a locking mechanism 140 (e.g. tabs), thereby compressing the host vessel wall 54 and the reinforcing graft wall 16 between the flared distal end 136 and the compression ring 112 as shown in FIG. 20E.

Figure 21B:
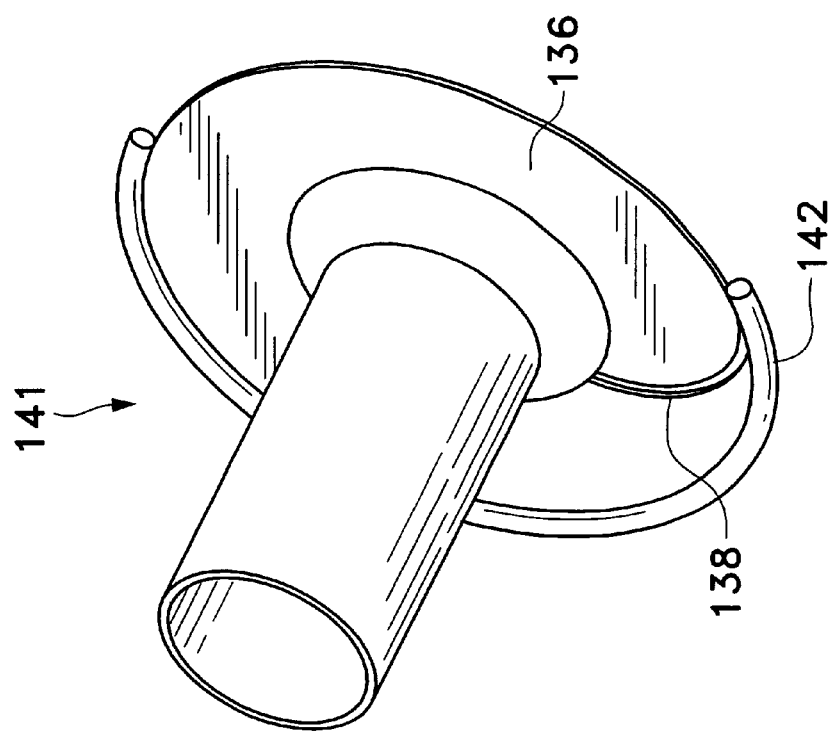
FIGS. 21A and 21B show further alternative end-side fittings.
Figure 21A:
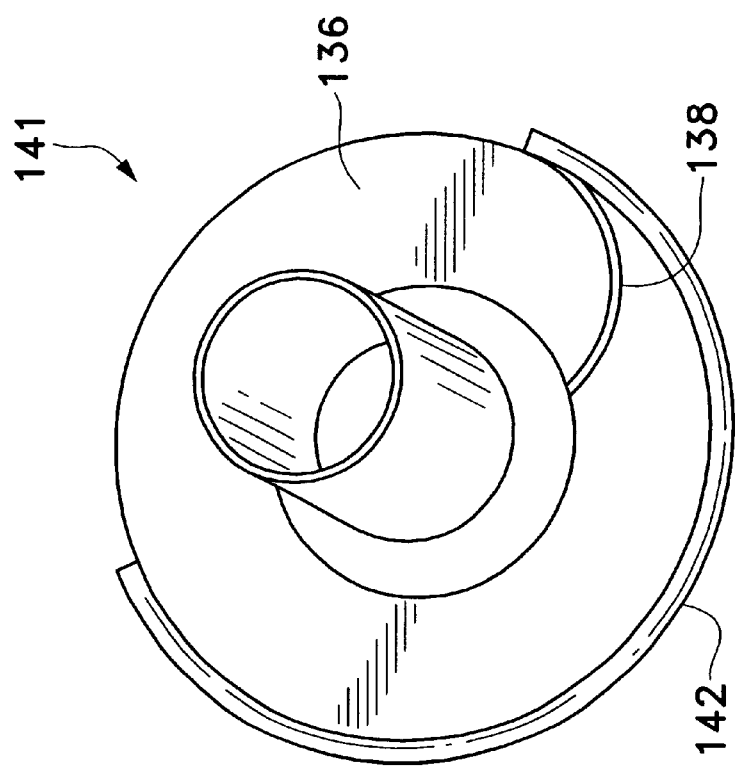

An alternative screw-in fitting 141 is shown in FIGS. 21A and 21B. In this configuration, a guidewire is inserted through the lumen of a needle. The needle is used to puncture the host vessel wall and the reinforcing graft wall and enter the interior of the reinforcing graft. The needle is then removed from around the guidewire. An insertion tubing 142 containing a central lumen follows the periphery of flared end and is adapted to pass a guidewire. The guidewire is fed through insertion tubing 142 to facilitate screwing the fitting past the host vessel wall and the reinforcing graft wall. The insertion tubing of the fitting extends approximately 40% to 80% around the flared end 136 circumference. Alternatively, the insertion tubing may be configured in sections extending around the circumference of the flared end so the physician may determine how far around the flared end the guidewire must extend to rotate the flared end past the host vessel wall and the reinforcing graft wall.

A slot 138 through distal flared end 136 is adapted to accept the thickness of the host vessel wall and the reinforcing graft wall and enables screwing the fitting through the host vessel wall and the reinforcing graft wall. As the screw-in fitting is advanced over the guidewire and rotated, the fitting simultaneously expands the puncture through host vessel wall and the reinforcing graft wall and inserts more of the distal flared end 136 into the interior of the reinforcing graft. The guidewire is then removed and the fitting is secured using a compression ring either as described above, by applying adhesives to the bond, by suturing the fitting, or by other bonding processes.

Additional Fitting Features

Figure 22:
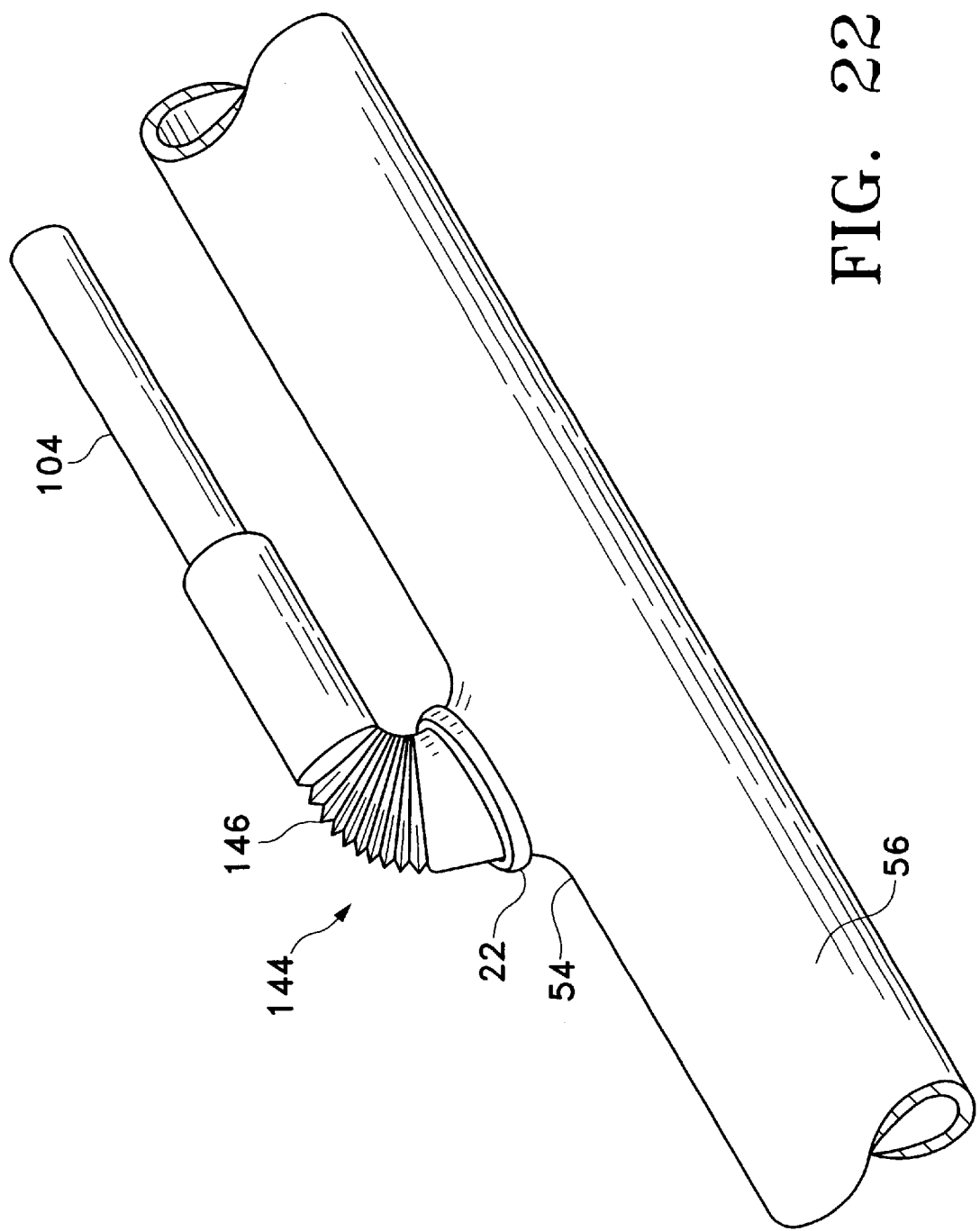
FIG. 22 shows a bypass graft and fitting combination attached to a host vessel wall and incorporating a strain relief around the fitting.

Additional features may be included in any of the fitting configurations described above. FIG. 22 shows a fitting 144 similar to the disclosed configurations having a strain relief 146 just proximal to the anastomosis. This strain relief provides additional support to the tubular structure (e.g. branching vessels) while preventing kinking. In addition, the strain relief reduces the profile of the fitting, making it less traumatic during use. The strain relief may be substituted for by making the proximal end of the end-side fitting flexible. Radial slots may be fabricated in the proximal end of the fitting to maintain radial stiffness but increase axial flexibility to function as a strain relief capable of preventing kinking of the tubular structure relative to the host vessel wall.

Another important feature is the incorporation of holes, notches, and slots in the fitting, fabricated by laser drilling, EDM, milling, or other manufacturing process. The fitting may alternatively be covered with a porous material, such as collagen, fibrinogen, gelatin, and urethane, to define a surface characterized by holes, notches, and slots. The incorporation of holes, notches and slots in the fitting provide a surface to encourage neointimal cell growth. This is especially important for fitting surfaces exposed to blood flow.

Aortic Aneurysm Treatment

Figure 6:
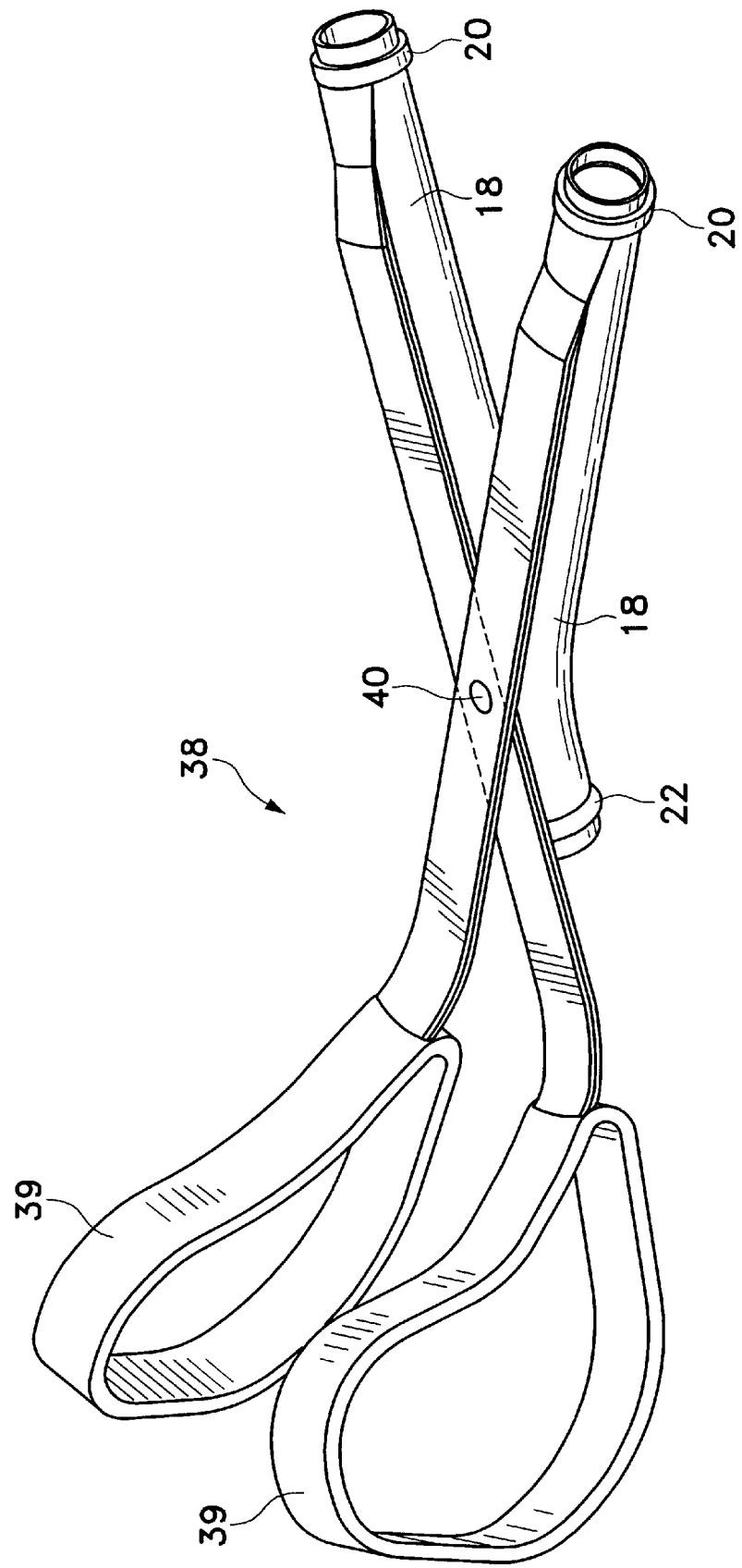
FIG. 6 shows an insertion device for advancing the ends of a bifurcating graft into branching vessels.
Figure 23:
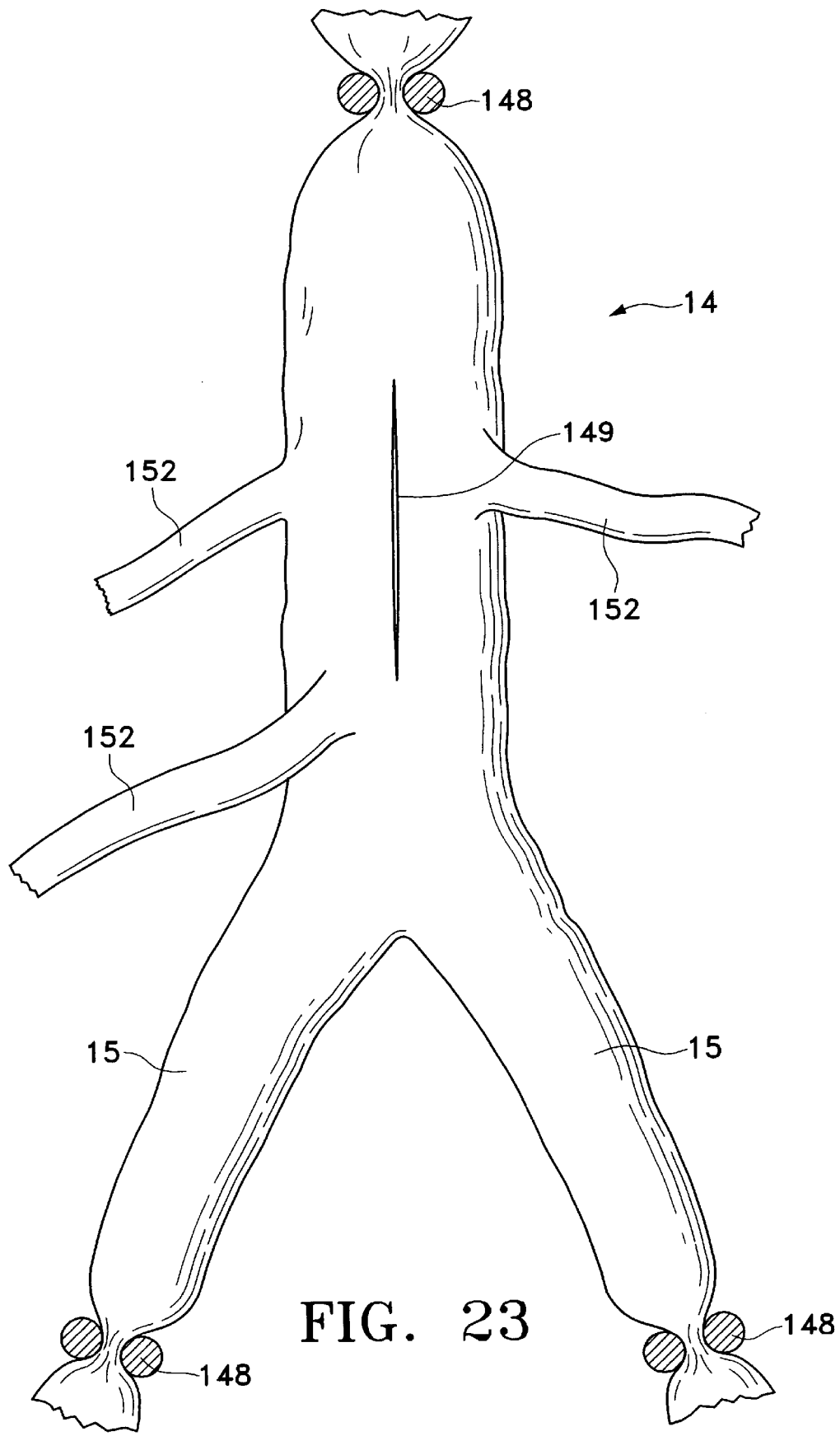
FIG. 23 is a view of the abdominal aorta showing representative branching vessels with the iliac arteries and the abdominal aorta clamped.
Figure 24:
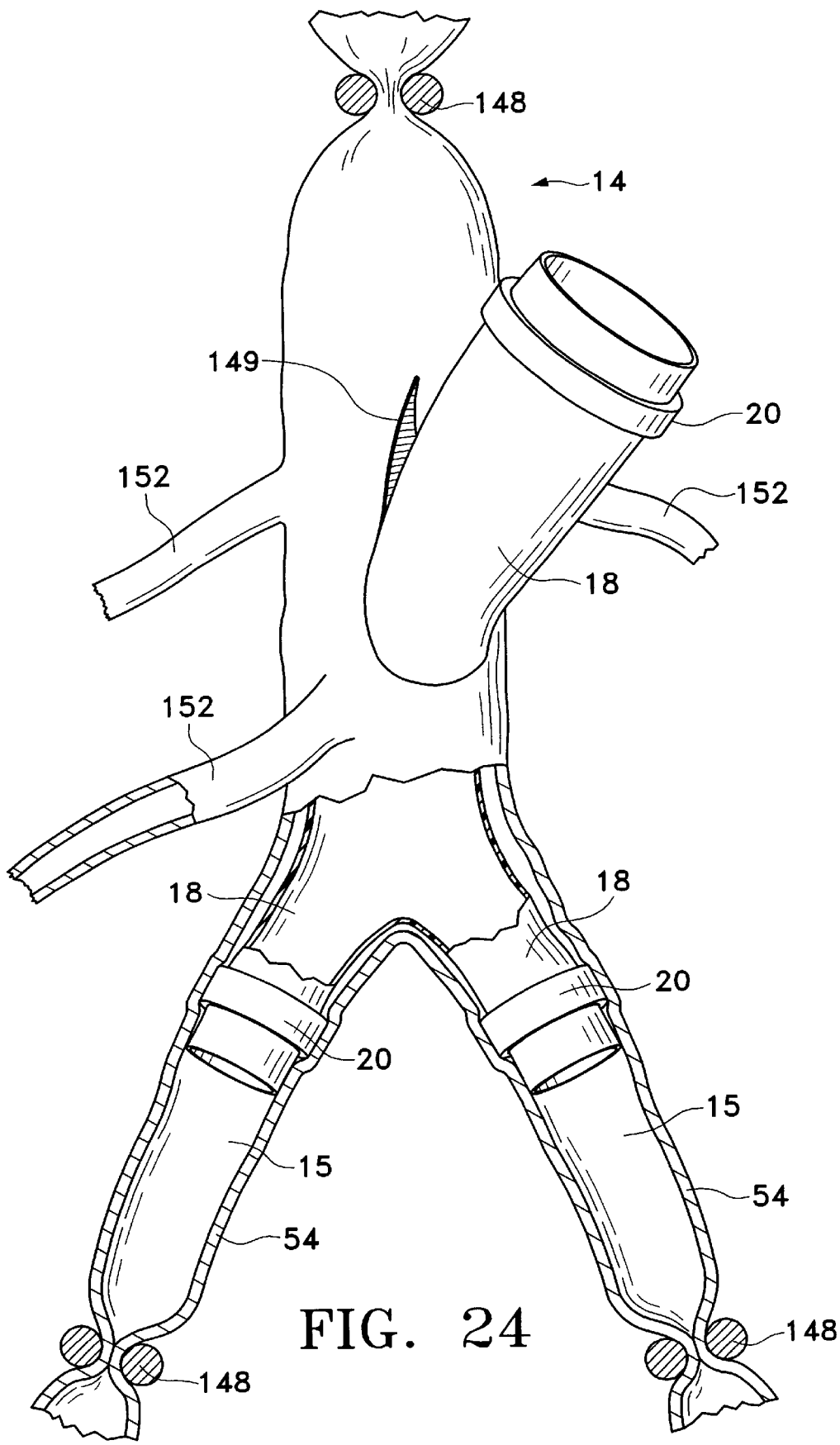
FIG. 24 is a partially sectioned view of the abdominal aorta with a reinforcing graft partially inserted into the vessel through an incision.
Figure 25:
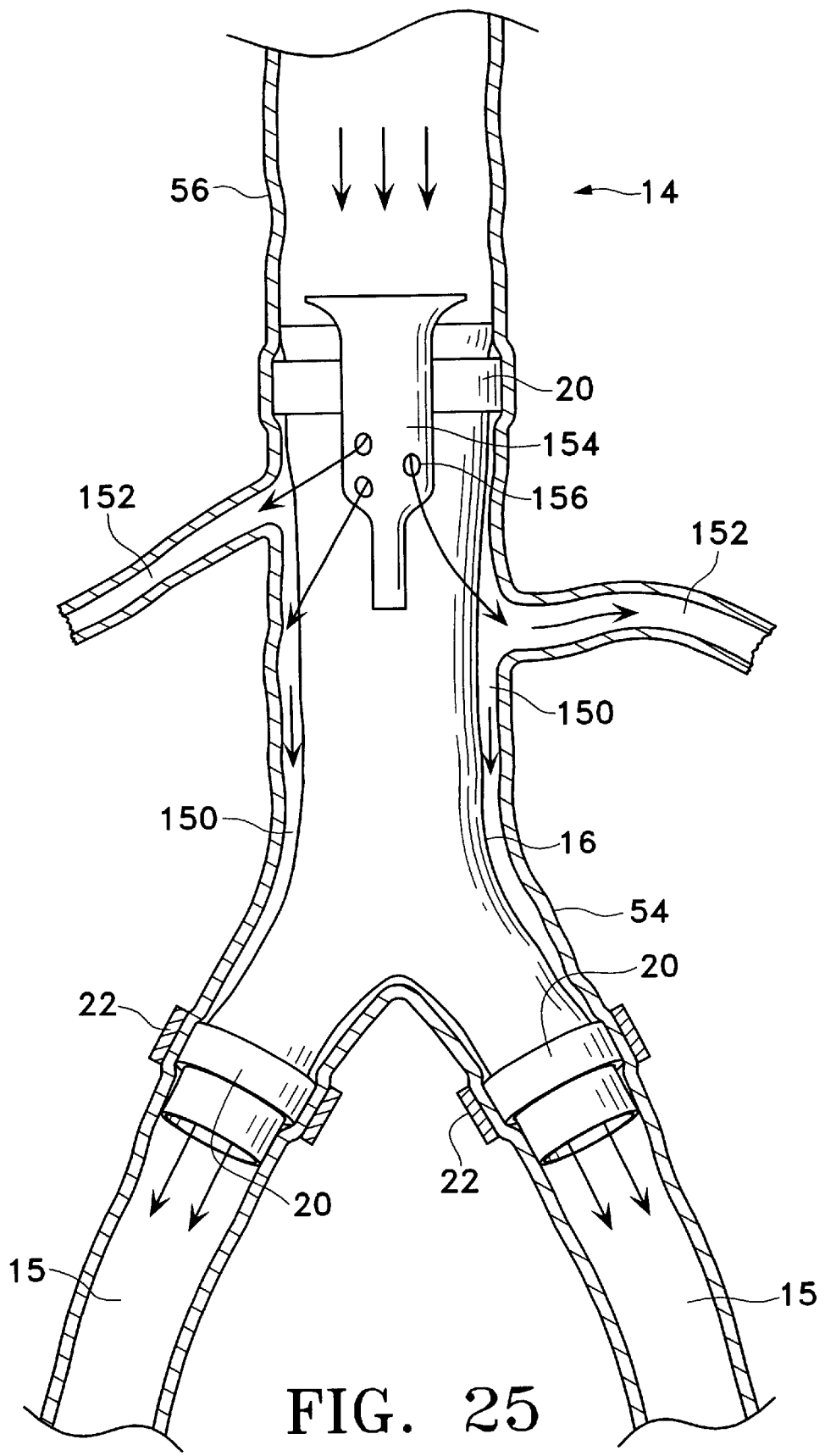
FIG. 25 shows a reinforcing graft inserted into the abdominal aorta and a vent enabling blood flow to branching vessels external to the reinforcing graft.
Figure 26A:
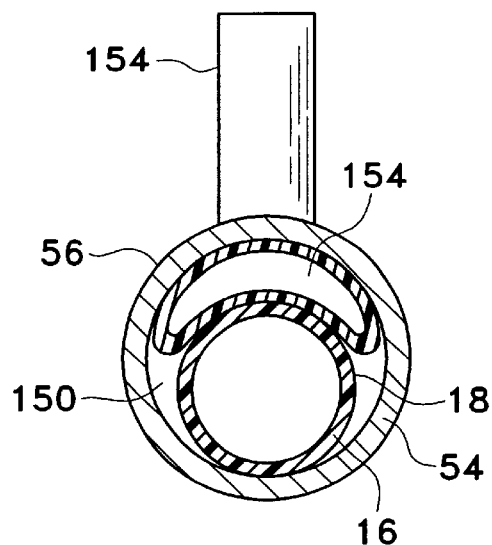
FIGS. 26A and 26B are end and side-sectional views of the vent positioned adjacent an end-end fitting of a reinforcing graft to permit blood flow external to the reinforcing graft.
Figure 26B:
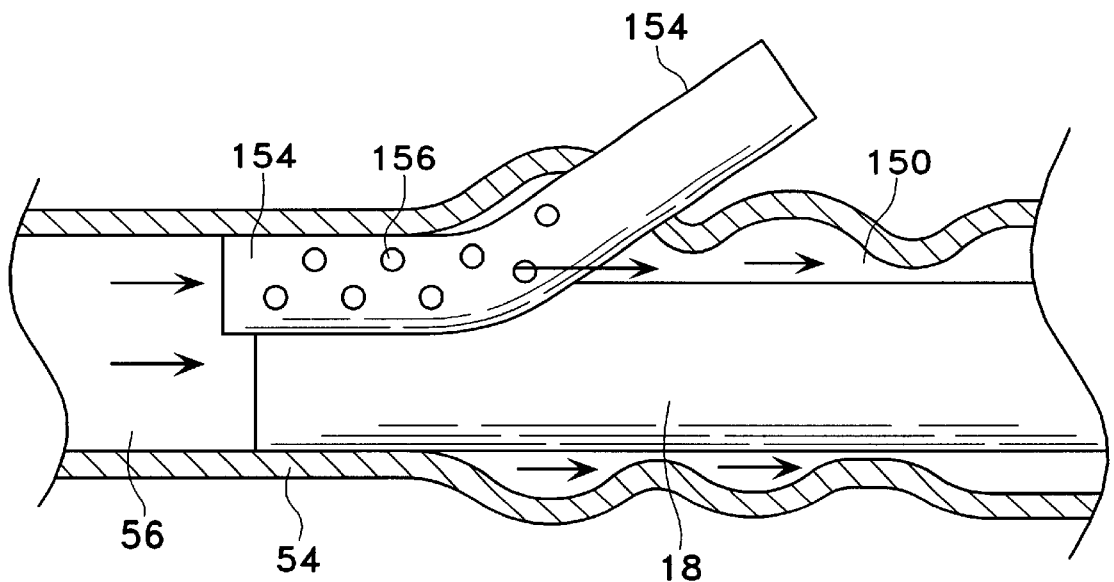
Figure 27:
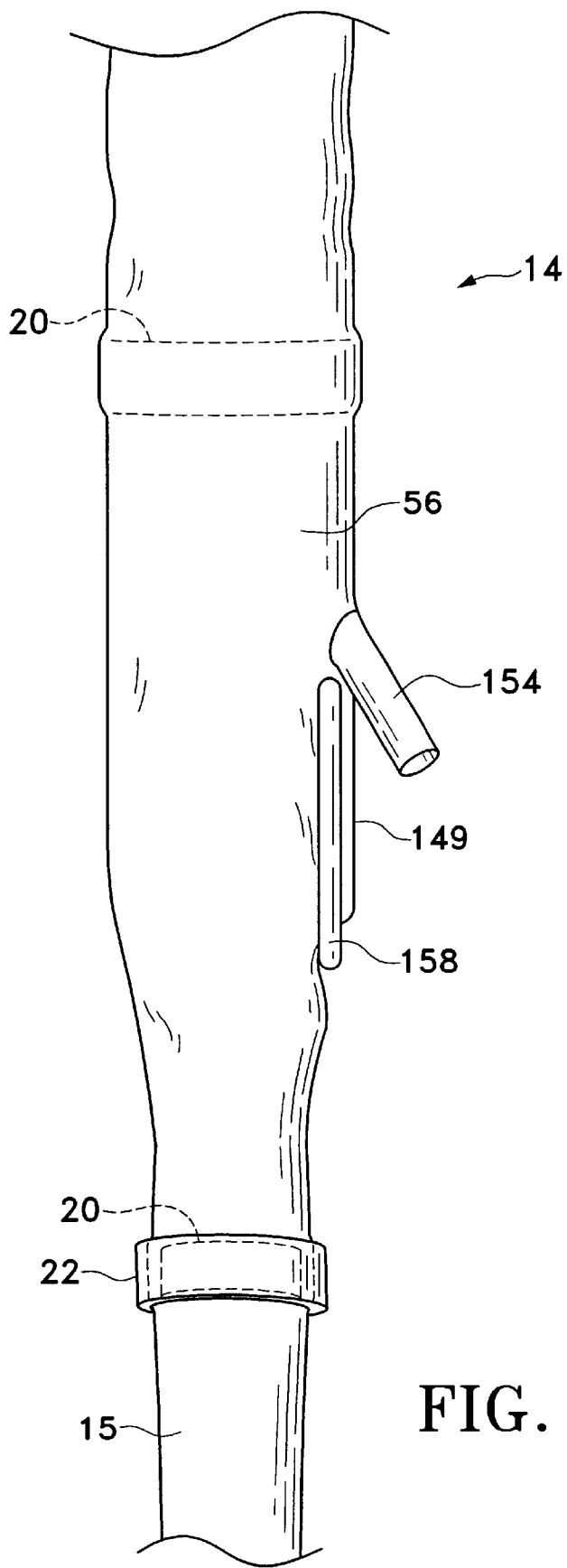
FIG. 27 is a side view of the abdominal aorta with the legs of the bifurcation secured to the iliac arteries and an incision through the vessel wall clamped.
Figure 28B:
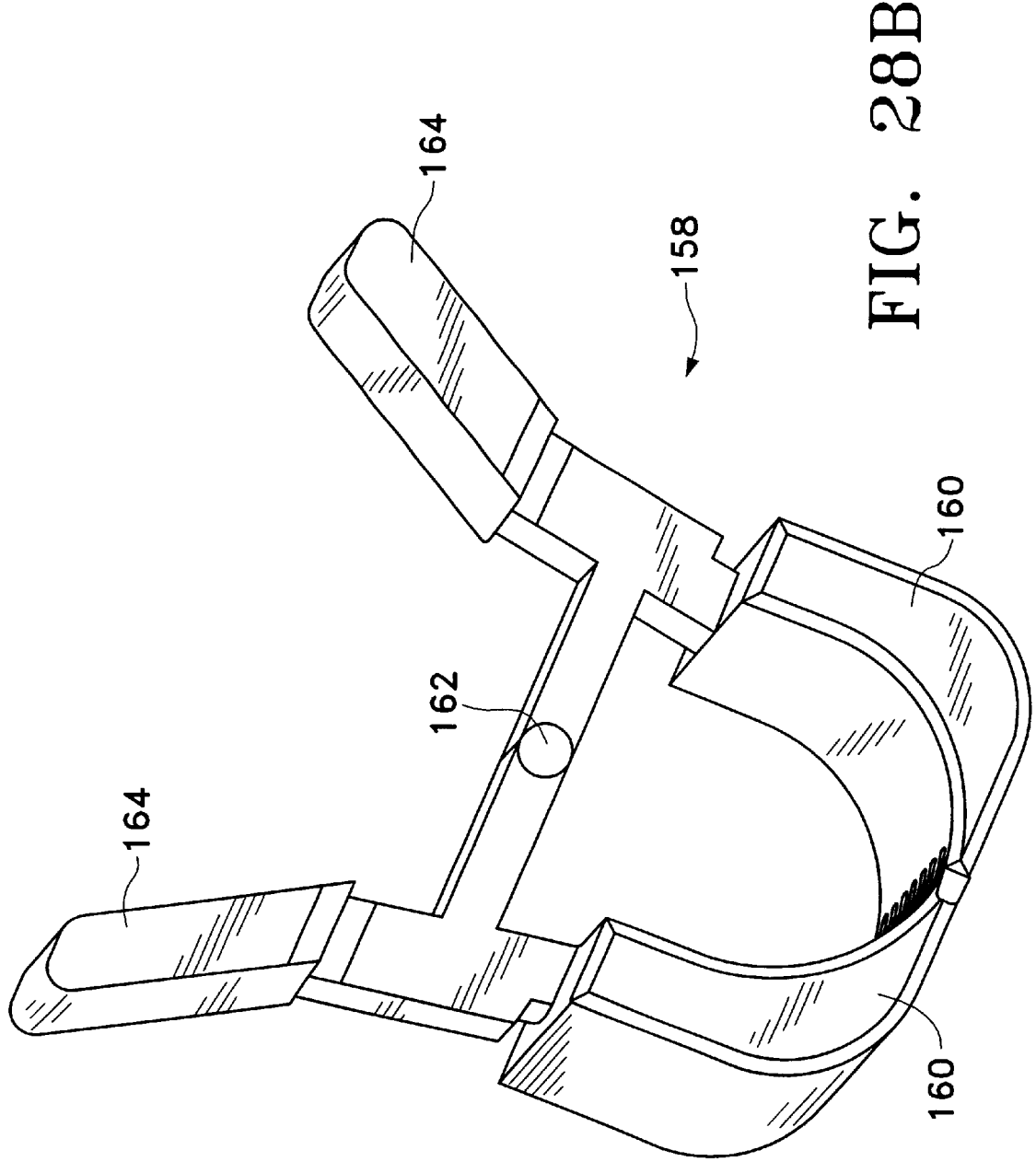
Figure 29:
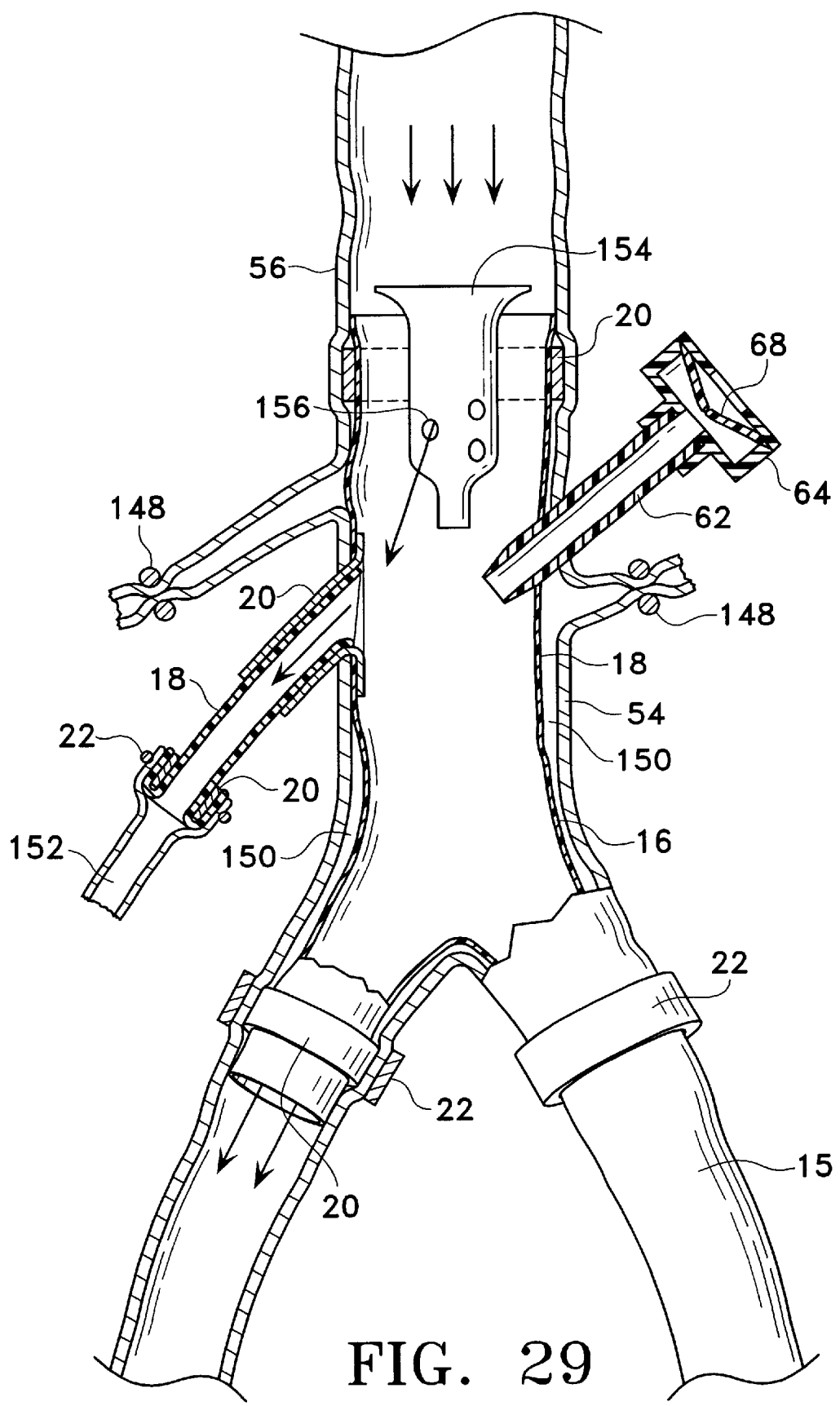
FIG. 29 is a partially sectioned view of a branching vessel secured to a reinforcing graft, also showing a delivery system accessing the interior of the reinforcing graft for deploying a branching vessel and fitting combination or an extension graft.

A process for securing a reinforcing graft to the aorta and reattaching branching vessels directly applies to treatment of abdominal aortic aneurysms, thoracic aortic aneurysms, and thoracoabdominal aortic aneurysms. In addition, this process addresses aortic root replacements and subsequent reattaching of the left main artery and right coronary artery to the replacement graft. However, the process for securing a reinforcing graft and reattaching the branching vessels will be described specifically for the treatment of abdominal aortic aneurysms:

1. Clamp the abdominal aorta 14 proximal and distal to the aneurysm using vessel clamps 148. If the aneurysm extends to the bifurcations, clamp the iliac arteries 15 instead of the distal region of the abdominal aorta, as shown in FIG. 23.
2. Cut an incision 149 through abdominal aorta 14 long enough to insert a reinforcing graft 18.
3. Insert the reinforcing graft through the incision and position the end-end fittings 20 of the reinforcing graft such that the reinforcing graft envelops the aneurysm, as shown in FIG. 24. An insertion tool 38 such as that shown in FIG. 6 is used to position the end-end fittings 20 at the desired host vessel locations.
4. Secure the distal end-end fittings 20 of the reinforcing graft to the abdominal aorta using a compression mechanism 22 (e.g. retaining ring), as shown in FIG. 25. Bifurcating reinforcing grafts contain two distal end-end fittings 20 that are to be secured using compression mechanisms 22 (e.g. retaining rings) to the common iliac arteries 15.
5. Remove vessel clamps 148 to re-establish blood flow through the reinforcing graft 18 to the peripheral vasculature and through the space 150 between the external surface of the reinforcing graft 18 and the abdominal aorta vessel wall 54, as shown in FIG. 25. Blood flowing through the space 150 perfuses the intact branching vessels 152.
6. Insert a vent 154 between the end-end fitting 20 of the proximal end of the reinforcing graft 18 and the abdominal aorta 14, as shown in FIGS. 25, 26A, and 26B. The vent includes an opening at the distal end and holes 156 along the side that enable blood flow to pass into the space 150 between the reinforcing graft and the abdominal aorta vessel wall. A temporary compression mechanism that resembles a retaining ring may be used to hold the proximal end-end fitting and the vent in place.
7. Clamp the incision 149 closed such that vent 154 is held in place, as shown in FIG. 27. An incision clamp 158 such as that shown in FIGS. 28A and 28B may be used to temporarily close the incision. The incision clamp has mating legs 160 that rotate relative to a pivot 162 that is spring loaded so the resting configuration of the incision clamp is closed. Two handles 164 are squeezed to rotate the legs and open the incision clamp for positioning along the sides of the incision. Once positioned, the handles are released thereby closing the incision. For subsequent removal, the handles are once again squeezed, opening the legs.
8. Near each branching vessel 152, puncture the abdominal aorta vessel wall and the reinforcing graft wall using the delivery system, as shown in FIG. 29. To better puncture the reinforcing graft wall, the puncture device of the delivery system may be oriented at an acute angle relative to the axis of the reinforcing graft and advanced along the lumen of the reinforcing graft. This prevents the reinforcing graft from radially collapsing which may cause the puncture device to perforate through the opposite side of the reinforcing graft wall and the abdominal aorta vessel wall. Alternatively, a mechanical supporting device may be inserted through the femoral artery (or other peripheral vessel) and into the abdominal aorta, and be positioned to exert radial force against the reinforcing graft wall at the puncture site (not shown). Such a mechanical expansion device is described in pending U.S. patent application Ser. No. 08/911,838, entitled "Mechanical Stent and Graft Delivery System" to Houser et al., filed Aug. 15, 1997, and incorporated in its entirety herein by reference. This mechanical expansion device may be used to support the reinforcing graft wall, permit blood to flow through the expansion strands, and provide a space between strands so the mechanical device does not obstruct puncturing through the reinforcing graft wall. The reinforcing graft may alternatively incorporate support structures at spaced intervals to maintain graft flexibility yet provide radial support for puncturing through the reinforcing graft, as will be described later.
9. Dilate the puncture site and position the delivery sheath 62 through the abdominal aorta vessel wall 54 and the reinforcing graft wall.
10. Tie off or clamp the branching vessel 152. Cut the branching vessel and attach it to an end-side fitting 20, as shown in FIG. 29.
11. Advance the branching vessel and fitting combination through the delivery sheath 62, as shown in FIG. 29.
12. Secure the end-side fitting 20 to the reinforcing graft wall and the abdominal aorta vessel wall using a compression ring.
13. Steps ten through twelve may be modified by using an extension graft attached to the side of the reinforcing graft wall and the abdominal aorta vessel wall using an end-side fitting 20, as shown in FIG. 29. The extension graft is secured prior to cutting the branching vessel and attaching the branching vessel to the end-end fitting 20 of the extension graft. The end-end fitting 20 of the extension graft may alternatively be inserted into the branching vessel using a delivery system, and secured with a compression mechanism (e.g. retaining ring) without having to cut the branching vessel. With this process, the extension graft is secured to the reinforcing graft wall and abdominal aorta vessel wall prior to inserting and securing the extension graft to the branching vessel. Therefore blood continuously flows through the branching vessel before, during, and immediately after securing the extension graft to the branching vessel.

Figure 30:
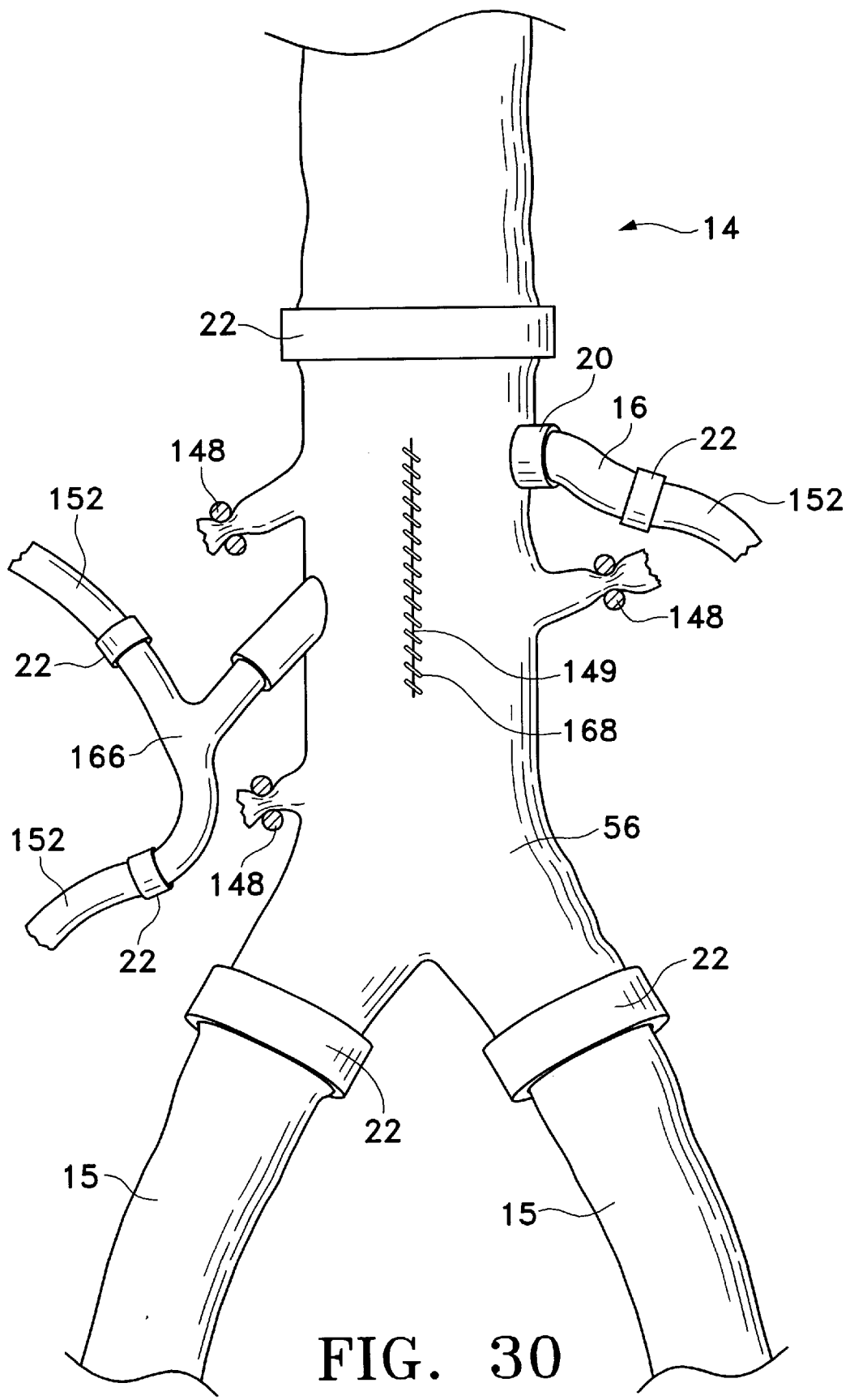
FIG. 30 shows a secured reinforcing graft isolating an aneurysm with branching vessels secured to the reinforcing graft.

14. Execute steps eight through thirteen for all remaining branching vessels. Bifurcating extension grafts 166 may be used to attach more than one branching vessel to the reinforcing graft wall and abdominal aortic aneurysm vessel wall using a single end-side fitting 20, as shown in FIG. 30. Each of the bifurcations of this extension graft 166 includes end-end fittings 20 against which the branching vessels may be compressed using a compression mechanisms 22.

15. Remove the vent from the incision as shown in FIG. 30.

16. Secure the proximal end-end fitting 20 of the reinforcing graft to the abdominal aorta using a compression mechanism 22 (e.g. retaining ring or suture), as shown in FIG. 30.

17. Remove the incision clamp 158 and inspect the space 150 between the reinforcing graft and the abdominal aorta for leaks. Adjust the end-end fittings 20 of the reinforcing graft 18 to correct for any detected leaks.

18. Stitch the incision closed with sutures 168.

The process described above may be modified to account for reinforcing grafts that may be compressed into a reduced diameter, inserted into the abdominal aorta, and positioned at the desired locations using a delivery system as opposed to requiring an incision. For this situation, blood flow through the host vessel would not need to be stopped at anytime during the procedure. Steps one through three would be substituted with the following: (1) insert a delivery sheath into the interior of the host vessel, (2) advance the reinforcing graft, compressed into a reduced diameter for insertion through the sheath, into the host vessel, and (3) position the end-end fittings at the desired host vessel locations using a steerable or preshaped insertion device. The vent tube, if necessary, would be inserted through the delivery sheath. After securing the reinforcing graft and reattaching the branching vessels, the vent tube would then be removed. After securing the proximal end-end fitting of the reinforcing graft, the opening defined by the delivery sheath would be stitched closed.

The delivery systems are capable of directly accessing the abdominal aorta, or percutaneously accessing the abdominal aorta from the femoral artery, popliteal artery, or the iliac artery. With direct access to the abdominal aorta, the delivery sheath may have a substantially larger diameter. This decreases the extent to which the end-end fittings of the reinforcing graft must be compressed into a reduced diameter. Therefore, end-end fittings capable of exerting substantial radial force may be used to adequately counteract the compression force exerted by the compression mechanism (retaining rings) when securing the host vessel wall between the end-end fitting and the compression mechanism. In addition, larger delivery systems facilitate positioning of the end-end fitting using an insertion tool because of the insertion tool has greater freedom of movement.

The process for positioning a reinforcing graft and re-establishing blood flow to branching vessels may modified for situations where the reinforcing graft 18 includes branches 36 which terminate into end-end fittings 20, as shown in FIG. 5. Branches 36 would be inserted into the branching vessels while positioning the reinforcing graft inside the abdominal aorta. As previously specified, this may be performed through an incision or through a delivery system. Insertion devices, described below, are used to position the branches. When inserting the ends of the reinforcing graft 18 and the branches 36 through a delivery system, the insertion device preferably incorporates a steering mechanism to remotely manipulate the end-end fitting to the appropriate vessel location. The orifices of the branches do not need to be located exactly at the orifices of the branching vessels. Instead, branches 36 run between the reinforcing graft 18 and the host vessel wall for a length before the branches extend into the lumen of the branching vessels; this accommodates the varying anatomy between patients. To ensure patency of the branches, especially where the branches are bent such that they extend parallel to the reinforcing graft for a length, the branches may incorporate a support structure, such as a helix or mesh of a metal alloy wire (e.g. nickel titanium). Once positioned inside the branching vessels, the end-end fittings 20 of the branches are secured to the branching vessels by producing end-end anastomoses as described below.

An alternative process for positioning and securing reinforcing grafts having branches 36 is to position the reinforcing graft into the abdominal aorta, as previously discussed, and fish the branches through the host vessel wall. Once the distal end-end fitting of the reinforcing graft is secured and the proximal end is positioned, the branches 36 may be fished through the abdominal aorta wall. To accomplish this, a small incision is created near the end-end fitting of the branch and a clamp is inserted through the incision to grab the end-end fitting and pull the branch through the host vessel wall. The location of the end-end fitting is determined from outside the host vessel wall by feeling for the more rigid end-end fitting.

An alternative method to fishing a branch 36 through the host vessel wall is to insert a wire having a hook through a small puncture in the host vessel wall and grab the branch with the inside surface of the wire-hook to pull the branch outside the host vessel wall. To prevent excess blood loss, the branches may be tied off until they are fished through the host vessel wall, at which time the ties may be removed. The branches incorporate end-end fittings to permit advancing the branching vessels, once cut, over the end-end fittings and securing with a compression mechanism (e.g. retaining ring or suture). Alternatively, the end-end fittings of the branches may be compressed into a reduced diameter for insertion into the intact branching vessels through a delivery system of the invention and secured to the branching vessels using compression mechanisms (e.g. retaining rings or suture).

The processes described above are for abdominal aortic aneurysms. However, the processes also apply to securing a reinforcing graft to the aorta and reattaching branching vessels for the treatment of thoracic aortic aneurysms, and thoracoabdominal aortic aneurysms. In addition, the processes apply aortic root replacements and subsequent reattaching of the left main artery and right coronary artery to the replacement graft.

Other Aneurysm Treatments

With slight modifications to the embodiments and processes described above, accounting for varying vessel diameters, other aneurysms may be treated. For example, extracranial carotid aneurysms requiring interposition grafts to reattach the internal carotid artery and the external carotid artery to the common carotid artery after removing the aneurysm may be treated with the embodiments and processes of the invention. An interposition graft consisting of a length of saphenous vein or synthetic graft may be configured to contain end-end fittings to facilitate attaching the interposition graft between the common carotid artery and either the internal or external carotid artery. As previously described, the interposition graft may be inserted through an incision in the host vessel wall or a delivery system accessing the interior of the host vessel through a puncture. Alternatively, the host vessels may be transected to remove the aneurysm tissue and attached to the end-end fittings of the interposition graft. The remaining one of the internal or external carotid artery is then attached to an end-side fitting, with or without an extension graft, to facilitate securing it to the interposition graft. The process and devices described herein for reattaching branching vessels are used to secure the remaining host vessel to the interposition graft. Alternatively, especially when using synthetic graft materials, the interposition graft may be fabricated with a bifurcation to facilitate attaching the common carotid artery to the internal carotid artery and the external carotid artery. The ends of the bifurcated interposition graft contain end-end fittings to facilitate attaching the host vessels.

The embodiments and processes of the invention may also be used to treat other types of aneurysms such as cerebral aneurysms, peripheral aneurysms including femoral and popliteal artery aneurysms, renal artery aneurysms, splanchnic artery aneurysms, hepatic artery aneurysms, celiac artery aneurysms, gastric and gastroepiploic artery aneurysms, pancreatic and pancreatoduodenal artery aneurysms, jejunal aneurysms, ileal and colic artery aneurysms, and mesenteric artery aneurysms, whether or not the treatment regimen requires reattaching branching vessels.

When treating aneurysms that do not require reattaching branching vessels, using the embodiments and processes of the invention, the reinforcing graft may be inserted through the host vessel wall using an incision or a delivery system of the invention. Once the end-end fittings of the reinforcing graft are positioned within the host vessel such that the graft envelops the aneurysm, the end-end fittings are secured with compression mechanisms (e.g. retaining rings) as described.

When aneurysms envelop branching vessels that feed organs susceptible to ischemic time, perfusion through the branching vessels and host vessel may be maintained while deploying the reinforcing graft, and reattaching branching vessels, as described for abdominal aortic aneurysm treatment above.

Briefly, the reinforcing graft may be inserted through an incision, which requires temporarily interrupting blood flow through the host vessel while positioning the end-end fittings. Alternatively, the reinforcing graft may be inserted through a delivery sheath, as described herein, which does not require stopping blood flow through the host vessel while deploying the reinforcing graft through the host vessel wall and positioning the end-end fittings.

The distal end-end fitting(s) of the reinforcing graft are then secured to the host vessel using compression mechanisms (e.g. retaining rings), as described. Blood is permitted to perfuse through the space between the proximal end-end fitting and the host vessel wall to the branching vessels enveloped by the reinforcing graft. A delivery sheath is then deployed through the host vessel wall and reinforcing graft, and the branching vessel is tied at the orifice, cut, attached to an end-side fitting, deployed through the delivery sheath, and secured to the reinforcing graft and host vessel using a compression ring.

As described for abdominal aortic aneurysm treatment, extension grafts may be used to lengthen the branching vessel (especially when part of the branching vessel is diseased and needs to be removed), enable reattaching the branching vessel without having to cut the branching vessel, or expedite reattaching the branching vessel.

After all branching vessels have been reattached, the proximal end-end fitting of the reinforcing graft is secured to the host vessel using a compression mechanism (e.g. retaining ring). Any incisions or punctures through the vessel wall would then be stitched closed.

We claim as our invention:

1. An aneurysm treatment system comprising:
    a reinforcing graft defining a first lumen, said graft having a first end to which a first inert fitting is affixed, said graft having a second end to which a second inert fitting is affixed,
    a first compression mechanism adapted to affix said first fitting to a vessel at a first vessel location distal to a vessel aneurysm, and
    a second compression mechanism adapted to affix said second fitting to the vessel at a second vessel location proximal to said aneurysm.

2. The aneurysm treatment system of claim 1 wherein one or both of the first or second compression mechanisms comprises a retaining ring.

3. The aneurysm treatment system of claim 1 wherein one or both of the first or second compression mechanisms comprises suture.

4. The aneurysm treatment system of claim 3 wherein each of said first and second inert fittings are comprised of a biologically inert material.

5. The aneurysm treatment system of claim 4 wherein said biologically inert material is selected from the group consisting of metals, alloys, thermoplastics, thermoset plastics, silicone, and combinations thereof.

6. The aneurysm treatment system of claim 4 wherein each of said first and second inert fittings are coated with a biologically inert material.

7. The aneurysm treatment system of claim 4 wherein each of said first and second inert fittings are coated with a biologically reative material for inhibiting troinbosis.

8. The aneurysm treatment system of claim 1 additionally comprising a vent.

9. The aneurysm treatment system of claim 1 additionally comprising an extension graft defining a second lumen, integrated to and extending from the reinforcing graft, and adapted to affix to at least one branching vessel such that a passage is created by said first lumen and said second lumen for fluid flow from the reinforcing graft through the extension graft to the at least one branching vessel.

10. The aneurysm treatment system of claim 1 additionally comprising a graft delivery system to access a lumen of the vessel and to permit insertion of the reinforcing graft therein and positioning of the first fitting.

11. The aneurysm treatment system of claim 10 wherein the graft delivery system comprises a puncture device, a dilator, and a sheath, wherein the puncture device is slidably engageable within a dilator, and wherein the sheath is slidably advanceable over the puncture device and dilator into the vessel lumen through an opening in the vessel created by the puncture device and expanded by the dilator.

12. The aneurysm treatment system of claim 11 wherein the graft delivery system additionally comprises a guidewire slidably advanceable through the puncture device to provide a path over which the dilator and sheath may advance.

13. The aneurysm treatment system of claim 10 wherein the graft delivery system comprises a needle, a guidewire, and a dilating sheath, wherein the guidewire is slidably advanceable through the needle to provide a path over which the dilating sheath may advance into the vessel lumen through an opening in the vessel created by the needle.

14. The aneurysm treatment system of claim 1 wherein the first and second compression mechanisms are adapted to affix said first and second fittings to the vessel, respectively, without any of the (a) first or second compression mechanisms or (b) first or second fittings penetrating a wall of the vessel.

15. The aneurysm treatment system of claim 1 additionally comprising an extension graft affixed at a proximal end to an opening in the reinforcing graft by a third fitting and affixed at a distal end to a branching vessel by a fourth fitting.

16. The aneurysm treatment system of claim 15 wherein the extension graft is a section of the branching vessel.

17. An aneurysm treatment system comprising:
   a reinforcing graft defining a first lumen, said graft having a first end to which a first inert fitting is affixed, said graft having a: second end to which a second inert fitting is affixed,
   a first compression mechanism adapted to affix said first fitting to a vessel at a first vessel location distal to a vessel aneurysm,
   a second compression mechanism adapted to affix said second fitting to the vessel at a second vessel location proximal to said aneurysm, and
   an extension graft defining a second lumen, integrated to and extending from the reinforcing graft, and adapted to affix to at least one branching vessel such that a passage is created by said first lumen and said second lumen for fluid flow from the reinforcing graft through the extension graft to the at least one branching vessel.

18. The aneurysm treatment system of claim 17 additionally comprising an extension graft fitting affixed to the extension graft and an extension graft compression mechanism adapted to secure the extension graft to the at least one branching vessel.

19. The aneurysm treatment system of claim 17 wherein one or both of the first or second compression mechanisms comprises a retaining ring.

20. The aneurysm treatment system of claim 17 wherein one or both of the first or second compression mechanisms comprises suture.

21. The aneurysm treatment system of claim 17 additionally comprising a graft delivery system to access a lumen of the vessel and to permit insertion of the reinforcing graft therein and positioning of the first fitting.

22. The aneurysm treatment system of claim 17 wherein each of said first and second inert fittings are comprised of a biologically inert material.

23. The aneurysm treatment system of claim 22 wherein said biologically inert material is selected from the group consisting of metals, alloys, thermoplastics, thermoset plastics, silicone, and combinations thereof.

24. The aneurysm treatment system of claim 22 wherein each of said first and second inert fittings are coated with a biologically inert material.

25. The aneurysm treatment system of claim 22 wherein each of said first and second inert fittings are coated with a biologically reactive material for inhibiting thrombosis.

26. A method for treating abdominal aortic aneurysms, comprising:
   (a) inserting a reinforcing graft having an inert fitting on each of a proximal and at least one distal reinforcing graft end into a lumen of an abdominal aorta,
   (b) positioning each reinforcing graft fitting in the lumen such that the reinforcing graft envelops an aneurysm in the abdominal aorta,
   (c) securing the at least one distal fitting to a vessel wall of the abdominal aorta,
   (d) creating openings in the abdominal aorta vessel wall and reinforcing graft wall near a branching vessel,
   (e) dilating the openings and positioning a delivery sheath through the abdominal aorta vessel wall and the reinforcing graft wall,
   (f) advancing an extension graft with an attached extension graft fitting through a delivery sheath,
   (g) securing the extension graft fitting to the reinforcing graft wall and the abdominal aorta vessel wall, and
   (h) securing the proximal reinforcing graft fitting to the abdominal aorta vessel wall.

27. The method of claim 25 wherein the extension graft is a portion of a branching.

28. The method of claim 25 wherein the extension graft is synthetic.

29. The method of claim 25 wherein steps (d)–(g) are repeated for each ranching vessel in the vicinity of the abdominal aorta.

30. The method of claim 25 comprising the additional step of inserting a vent reinforcing graft proximal fitting and the abdominal aorta wall after step (c) and vent before step (h).

31. The aneurysm treatment system of claim 1 additionally comprising an insertion tool configured to position each of the first and second fittings at said first and said second vessel locations.

* * * * *